US011926661B2

(12) United States Patent
Croll et al.

(10) Patent No.: US 11,926,661 B2
(45) Date of Patent: Mar. 12, 2024

(54) HUMAN ANTIBODIES TO ARTEMIN AND METHODS OF USE THEREOF

(71) Applicant: Regeneron Pharmaceuticals, Inc., Tarrytown, NY (US)

(72) Inventors: Susan D. Croll, New Paltz, NY (US); Lynn MacDonald, Harrison, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 4 days.

(21) Appl. No.: 17/724,381

(22) Filed: Apr. 19, 2022

(65) Prior Publication Data

US 2022/0340652 A1    Oct. 27, 2022

Related U.S. Application Data

(60) Provisional application No. 63/177,369, filed on Apr. 20, 2021.

(51) Int. Cl.
*C07K 16/22* (2006.01)
*A61K 39/395* (2006.01)
*A61P 29/02* (2006.01)

(52) U.S. Cl.
CPC .......... *C07K 16/22* (2013.01); *A61K 39/3955* (2013.01); *A61P 29/02* (2018.01); *C07K 2317/21* (2013.01); *C07K 2317/33* (2013.01); *C07K 2317/76* (2013.01); *C07K 2317/92* (2013.01)

(58) Field of Classification Search
CPC .......................... C07K 16/22; A61K 2039/505
See application file for complete search history.

(56) References Cited

U.S. PATENT DOCUMENTS

| | | |
|---|---|---|
| 6,284,540 B1 | 9/2001 | Milbrandt et al. |
| 7,582,298 B2 | 9/2009 | Stevens et al. |
| 8,697,940 B2 | 4/2014 | Macdonald et al. |
| 10,047,150 B2 | 8/2018 | Rossomando et al. |
| 10,130,081 B2 | 11/2018 | McWhirter et al. |
| 10,561,124 B2 | 2/2020 | Macdonald et al. |
| 10,640,800 B2 | 5/2020 | Murphy et al. |
| 2007/0280945 A1 | 12/2007 | Stevens et al. |
| 2017/0096488 A1 | 4/2017 | Croll et al. |
| 2017/0281756 A1 | 10/2017 | McKerny |

FOREIGN PATENT DOCUMENTS

| | | |
|---|---|---|
| WO | WO 2016077666 | 12/2007 |
| WO | WO 2014/031712 | 2/2014 |

OTHER PUBLICATIONS

Airaksinen, et al. (2002) "The GDNF Family: Signalling, Biological Functions and Therapeutic Value", Nature Reviews Neuroscience, Nature Publishing Group, 13(5):383-394.

(Continued)

*Primary Examiner* — Aurora M Fontainhas
*Assistant Examiner* — Jennifer A Benavides
(74) *Attorney, Agent, or Firm* — FisherBroyles, LLP; Cara L. Crowley-Weber; Lisa Dornbach Flanagan

(57) ABSTRACT

The present disclosure provides antibodies and antigen-binding fragments thereof that bind to human artemin. Methods for using anti-artemin antibodies and antigen-binding fragments are also provided.

27 Claims, 4 Drawing Sheets

Specification includes a Sequence Listing.

(56) References Cited

OTHER PUBLICATIONS

Sah, et al. (2005) "New Approaches for the Treatment of Pain: The GDNF Family of Neurotrophic Growth Factors", Current Topics in Medicinal Chemistry, 5(6): 577-583.
PCT International Search Report and Written Opinion for International Application No. PCT/US2022/025424 dated Sep. 12, 2022, 20 pages.
Airaksinen et al. (2002) "The GDNF Family: Signalling, Biological Functions and Therapeutic Value," Nature Reviews Neuroscience, 3:383-394.
Airaksinen et al. (2006) "Evolution of the GDNF Family Ligands and Receptors," Brain, Behavior and Evolution, 68:181-190.
Allen Jr (1999) "The Art, Science and Technology of Pharmaceutical Compounding," fifth edition, American Pharmacists Association, Washington, D.C., pp. 1-8.
Altschul et al. (1990) "Basic Local Alignment Search Tool," J. Mol. Biol. 215: 403-410.
Altschul et al. (1997) "Gapped BLAST and PSI-BLAST: a New Generation of Protein Database Search Programs," Nucleic Acids Res., 25(17):3389-3402.
Baloh et al. (1998) "Artemin, a Novel Member of the GDNF Ligand Family, Supports Peripheral and Central Neurons and Signals through the GFRα3-RET Receptor Complex," Neuron, 21(6):1291-1302.
Ehring (1999) "Hydrogen Exchange/Electrospray Ionization Mass Spectrometry Studies of Structural Features of Proteins and Protein/Protein Interactions," Analytical Biochemistry, 267(2):252-259.
Elitt et al. (2006) "Artemin Overexpression in Skin Enhances Expression of TRPV1 and TRPA1 in Cutaneous Sensory Neurons and Leads to Behavioral Sensitivity to Heat and Cold," J. Neuroscience, 26(33): 8578-8587.
Engen and Smith (2001) "Investigating Protein Structure and Dynamics by Hydrogen Exchange MS," Anal Chem, 73(9):256A-265A.
Gonnet et al. (1992) "Exhaustive Matching of the Entire Protein Sequence Database," Science 256:1443-1445.
Hargreaves et al. (1988) "A New and Sensitive Method for Measuring Thermal Nociception in Cutaneous Hyperalgesia" Pain 32(1):77-88.
Harlow and Lane (2014) "Antibodies," A Laboratory Manual, Second Edition (Cold Spring Harbor Press, Cold Spring Harbor, NY, pp. 1-22.
Honma et al. (2002) "Artemin Is a Vascular-Derived Neurotropic Factor for Developing Sympathetic Neurons," Neuron, 35:267-282.
Junghans et al. (1990) "Anti-Tac-H, a Humanized Antibody to the Interleukin 2 Receptor with New Features for Immunotherapy in Malignant and Immune Disorders," Cancer Res., 50:1495-1502.
Kazane et al. (2013) "Self-Assembled Antibody Multimers through Peptide Nucleic Acid Conjugation," J. Am. Chem. Soc., 135:340-346 [Epub: Dec. 4, 2012].
Klein et al. (2012) "Progress in Overcoming the Chain Association Issue in Bispecific Heterodimeric IgG Antibodies," mAbs 4(6):653-663.
Langer (1990) "New Methods of Drug Delivery," Science, 249:1527-1533.
Langer and Wise, (1984) "Medical Applications of Controlled Release", vol. II, CRC Pres., Boca Raton, Florida, pp. 115-138.
Malin et al. (2006) "Glial Cell Line-Derived Neurotrophic Factor Family Members Sensitize Nociceptors In Vitro and Produce Thermal Hyperalgesia In Vivo," J. Neuroscience, 26(33): 8588-8599.
Mordenti et al. (1991) "Interspecies Scaling of Clearance and Volume of Distribution Data for Five Therapeutic Proteins," Pharmaceut. Res. 8:1351-1359.
Nolan et al. (2020) "Pet Dogs with Subclinical Acute Radiodermatitis Experience Widespread Somatosensory Sensitization" Radiat Res 193(3):241-248.
Orozco et al. (2001) "Short Communication GFRalpha3 is Expressed Predominantly in Nociceptive Sensory Neurons," European J. Neuroscience, 13:2177-2182.
Pearson (2000) "Flexible Sequence Similarity Searching with the FASTA3 Program Package," Methods in Molecular Biology, 132:185-219.
Protein [Internet]. Bethesda (MD): National Library of Medicine (US), National Center for Biotechnology Information; [2022]—Accession No. NP_001487.2, "GDNF family receptor alpha-3 preproprotein [*Homo sapiens*]", cited on Feb. 16, 2021, [online], [retrieved on Jul. 8, 2022]. Retrieved from: https://www.ncbi.nlm.nihm.gov/protein/ NP_001487.2, 4 pages.
Protein [Internet]. Bethesda (MD): National Library of Medicine (US), National Center for Biotechnology Information; [2022]—Accession No. NP_065681.1, "proto-oncogene tyrosine-protein kinase receptor Ret isoform c precursor [*Homo sapiens*]", cited on Jun. 12, 2022, [online], [retrieved on Jul. 8, 2022]. Retrieved from: https://www.ncbi.nlm.nihm.gov/protein/NP_065681.1, 5 pages.
Protein [Internet]. Bethesda (MD): National Library of Medicine (US), National Center for Biotechnology Information; [2022]—Accession No. NP_476432.2, "Artemin Isoform 1 Preproprotein [*Homo sapiens*]", cited on May 31, 2022, [online], [retrieved on Jul. 8, 2022]. Retrieved from: https://www.ncbi.nlm.nihm.gov/protein/ NP_476432.2, 3 pages.
Reineke (2004) "Antibody Epitope Mapping Using Arrays of Synthetic Peptides," Methods Mol Biol, 248:443-463.
Sefton (1987) "Implantable Pumps," CRC Crit. Ref. Biomed. Eng. 14(3):201-240.
Shang et al. (2016) "Expression of Artemin and GFRα3 in an Animal Model of Migraine: Possible Role in the Pathogenesis of this Disorder," J Headache Pain, 17(1):81.
Shinoda et al. (2015) "Involvement of Peripheral Artemin Signaling in Tongue Pain: Possible Mechanism in Burning Mouth Syndrome" Pain 156(12):2528-2537.
Taylor et al. (1992) "A Transgenic Mouse that Expresses a Diversity of Human Sequence Heavy and Light Chain Immunoglobulins," Nucl. Acids Res. 20(23):6287-6295.
Tomer (2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis," Prot Sci, 9:487-496.
Wu et al. (1987) "Receptor-Mediated in Vitro Gene Transformation by a Soluble DNA Carrier System," J. Biol. Chem., 262(10):4429-4432.

FIG. 2

SEQUENCE LISTING

<160> NUMBER OF SEQ ID NOS: 85

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1
gaggtgcagc tggtggagag cggcggcgac ctggtgcagc ccggcggcag cctgaagctg      60
agctgcgccg ccagcggctt caccttcagc ggcagcgcca tgcactgggt gaggcaggcc     120
agcggcaagg gcctggagtg ggtgggcagg atcaggaaca aggtgcacag gtacgccacc     180
gagtacggcg ccagcgtgaa gggcaggttc accatcagca gggacgacag caagaacacc     240
gcctacctgc agatgaacag cctgaagatc gaggacaccg ccgtgtacta ctgcgtggtg     300
gtggtgcccg gcagcatcga ggccttcgac atctggggcc agggcaccat ggtgaccgtg     360
agcagc                                                                366

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Asn Lys Val His Arg Tyr Ala Thr Glu Tyr Gly Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Ile Glu Asp Thr Ala Val Tyr
                85                  90                  95

Tyr Cys Val Val Val Val Pro Gly Ser Ile Glu Ala Phe Asp Ile Trp
            100                 105                 110

Gly Gln Gly Thr Met Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggcttcacct tcagcggcag cgcc                                             24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Gly Ser Ala
1               5

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5
atcaggaaca aggtgcacag gtacgccacc                                      30

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Ile Arg Asn Lys Val His Arg Tyr Ala Thr
1               5                   10

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
gtggtggtgg tgcccggcag catcgaggcc ttcgacatc                             39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Val Val Val Val Pro Gly Ser Ile Glu Ala Phe Asp Ile
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gacatccaga tgacccagag ccccagcagc ctgagcgcca gcgtgggcga cagggtgacc      60
atcacctgca gggccagcca gagcatcagc acctacctga actggtacca gcagaagccc     120
ggcaaggccc ccaacctgct gatctacgcc gccagcaccc tggagagcgg cgtgcccagc     180
aggttcagcg gcagcggcag cggcaccgac ttcaccctga ccatcagcag cctgcagccc     240
gaggacttcg agatctacta ctgccagcag agctacaaca tcccctggac cttcggccag     300
ggcaccaagg tggagatcaa g                                              321

```
<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Asn Leu Leu Ile
        35                  40                  45

Tyr Ala Ala Ser Thr Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Glu Ile Tyr Tyr Cys Gln Gln Ser Tyr Asn Ile Pro Trp
                85                  90                  95

Thr Phe Gly Gln Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagcatca gcacctac                                                       18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Thr Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gccgccagc                                                                  9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
1
```

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcagagct acaacatccc ctggacc                                         27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Asn Ile Pro Trp Thr
1               5

<210> SEQ ID NO 17
<211> LENGTH: 1347
<212> TYPE: DNA
<213> ORGANISM: Artificial Sequence
<220> FEATURE:
<223> OTHER INFORMATION: Synthetic

<400> SEQUENCE: 17
gaggtgcagc tggtggagag cggcggcgac ctggtgcagc ccggcggcag cctgaagctg      60
agctgcgccg ccagcggctt caccttcagc ggcagcgcca tgcactgggt gaggcaggcc     120
agcggcaagg gcctggagtg ggtgggcagg atcaggaaca aggtgcacag gtacgccacc     180
gagtacggcg ccagcgtgaa gggcaggttc accatcagca gggacgacag caagaacacc     240
gcctacctgc agatgaacag cctgaagatc gaggacaccg ccgtgtacta ctgcgtggtg     300
gtggtgcccg gcagcatcga ggccttcgac atctggggcc agggcaccat ggtgaccgtg     360
agcagcgcca gcaccaaggg ccccagcgtg ttccccctgg cccccctgca gaggagcacc     420
agcgagagca ccgccgccct gggctgcctg gtgaaggact acttccccga gcccgtgacc     480
gtgagctgga acagcggcgc cctgaccagc ggcgtgcaca ccttccccgc cgtgctgcag     540
agcagcggcc tgtacagcct gagcagcgtg gtgaccgtgc cagcagcag cctgggcacc     600 aagacctaca cctgcaacgt ggaccacaag cccagcaaca ccaaggtgga caagagggtg     660
gagagcaagt acggcccccc ctgcccccc tgccccgccc ccgagttcct gggcggcccc     720
agcgtgttcc tgttcccccc caagcccaag gacaccctga tgatcagcag gacccccgag     780
gtgacctgcg tggtggtgga cgtgagccag gaggacccg aggtgcagtt caactggtac     840
gtggacggcg tggaggtgca caacgccaag accaagccca ggaggagca gttcaacagc     900 acctacaggg tggtgagcgt gctgaccgtg ctgcaccagg actggctgaa cggcaaggag     960
tacaagtgca aggtgagcaa caagggcctg cccagcagca tcgagaagac catcagcaag    1020
gccaagggcc agccccaggga gccccaggtg tacaccctgc cccccagcca ggaggagatg    1080
accaagaacc aggtgagcct gacctgcctg gtgaagggct ctacccccag cgacatcgcc    1140
gtggagtggg agagcaacgg ccagcccgag aacaactaca agaccacccc ccccgtgctg    1200
gacagcgacg gcagcttctt cctgtacagc aggctgaccg tggacaagag caggtggcag    1260
gagggcaacg tgttcagctg cagcgtgatg cacgaggccc tgcacaacca ctacacccag    1320
aagagcctga gcctgagcct gggcaag                                                    1347

<210> SEQ ID NO 18
<211> LENGTH: 449
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Asp Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Asn Lys Val His Arg Tyr Ala Thr Glu Tyr Gly Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Ile Glu Asp Thr Ala Val Tyr
                85                  90                  95

Tyr Cys Val Val Val Pro Gly Ser Ile Glu Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 19
<211> LENGTH: 642
<212> TYPE: DNA
<213> ORGANISM: Artificial Sequence
<220> FEATURE:
<223> OTHER INFORMATION: Synthetic

<400> SEQUENCE: 19
gacatccaga tgacccagag ccccagcagc ctgagcgcca gcgtgggcga cagggtgacc      60
atcacctgca gggccagcca gagcatcagc acctacctga actggtacca gcagaagccc     120
ggcaaggccc ccaacctgct gatctacgcc gccagcaccc tggagagcgg cgtgcccagc     180
aggttcagcg gcagcggcag cggcaccgac ttcaccctga ccatcagcag cctgcagccc     240
gaggacttcg agatctacta ctgccagcag agctacaaca tcccctggac cttcggccag     300
ggcaccaagg tggagatcaa gaggaccgtg gccgccccca gcgtgttcat cttccccccc     360
agcgacgagc agctgaagag cggcaccgcc agcgtggtgt gcctgctgaa caacttctac     420
cccagggagg ccaaggtgca gtggaaggtg gacaacgccc tgcagagcgg caacagccag     480
gagagcgtga ccgagcagga cagcaaggac agcacctaca gcctgagcag caccctgacc     540
ctgagcaagg ccgactacga gaagcacaag gtgtacgcct gcgaggtgac ccaccagggc     600
ctgagcagcc ccgtgaccaa gagcttcaac agggcgagt gc                         642

<210> SEQ ID NO 20
<211> LENGTH: 214
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Asn Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Glu Ile Tyr Tyr Cys Gln Gln Ser Tyr Asn Ile Pro Trp
                85                  90                  95

Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 21
<211> LENGTH: 360
<212> TYPE: DNA
<213> ORGANISM: Artificial Sequence
<220> FEATURE:
<223> OTHER INFORMATION: Synthetic

<400> SEQUENCE: 21
gaggtgcagc tggtggagag cggcggcggc ctggtgcagc ccggcggcag cctgaggctg     60
agctgcgccg ccagcggctt caccttcagc agctacgaca tgcactgggt gaggcaggcc    120
accggcaagg gcctggagtg ggtgagcacc atcgacaccg ccggcgacac ctactacccc    180
ggcagcgtga agggcaggtt caccatcagc agggagaacg ccaagaacag cctgtacctg    240
cagatgaaca gcctgagggc cggcgacacc gccgtgtact actgcgccag ggacggcgag    300
ctggagctgc agggctactt cgacctgtgg ggcaggggca ccctggtgac cgtgagcagc    360

<210> SEQ ID NO 22
<211> LENGTH: 120
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met His Trp Val Arg Gln Ala Thr Gly Lys Gly Leu Glu Trp Val
        35                  40                  45
Ser Thr Ile Asp Thr Ala Gly Asp Thr Tyr Tyr Pro Gly Ser Val Lys
    50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Ala
                85                  90                  95
Arg Asp Gly Glu Leu Glu Leu Gln Gly Tyr Phe Asp Leu Trp Gly Arg
            100                 105                 110
Gly Thr Leu Val Thr Val Ser Ser

-continued

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
ggcttcacct tcagcagcta cgac                                    24

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Gly Phe Thr Phe Ser Ser Tyr Asp
1               5

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
atcgacaccg ccggcgacac c                                       21

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Ile Asp Thr Ala Gly Asp Thr
1               5

<210> SEQ ID NO 27
<211> LENGTH: 42
<212> TYPE: DNA
<213> ORGANISM: Artificial Sequence
<220> FEATURE:
<223> OTHER INFORMATION: Synthetic

<400> SEQUENCE: 27
gccagggacg gcgagctgga gctgcagggc tacttcgacc tg                 42

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Ala Arg Asp Gly Glu Leu Glu Leu Gln Gly Tyr Phe Asp Leu
1               5                   10

<210> SEQ ID NO 29

<210> SEQ ID NO 29
<211> LENGTH: 321
<212> TYPE: DNA
<213> ORGANISM: Artificial Sequence
<220> FEATURE:
<223> OTHER INFORMATION: Synthetic

<400> SEQUENCE: 29

```
gacatccaga tgacccagag ccccagcagc ctgagcgcca gcgtgggcga cagggtgacc      60
atcacctgca gggccagcca gatcatcagc atctacctga actggtacca gcagaagccc     120
ggcaaggccc ccaagctgct gatctacgcc gccagcagcc tgcagagcgg cgtgcccagc     180
aggttcagcg gcagcggcag cggcaccgac ttcaccctga ccatcagcag cctgcagccc     240
gaggacttcg ccacctacta ctgccagcag agctacacca ccccccctgac cttcggcggc     300
ggcaccaagg tggagatcaa g                                               321
```

<210> SEQ ID NO 30
<211> LENGTH: 107
<212> TYPE: PRT
<213> ORGANISM: Artificial Sequence
<220> FEATURE:
<223> OTHER INFORMATION: Synthetic

<400> SEQUENCE: 30

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ile Ile Ser Ile Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Thr Thr Pro Leu
                85                  90                  95
Thr Phe Gly Gly Gly Thr Lys Val Glu Ile Lys
            100                 105

<210> SEQ ID NO 31
<211> LENGTH: 18
<212> TYPE: DNA
<213> ORGANISM: Artificial Sequence
<220> FEATURE:
<223> OTHER INFORMATION: Synthetic

<400> SEQUENCE: 31

```
cagatcatca gcatctac                                                   18
```

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Gln Ile Ile Ser Ile Tyr
1               5

<210> SEQ ID NO 33
<211> LENGTH: 9

```
<212> TYPE: DNA
<213> ORGANISM: Artificial Sequence
<220> FEATURE:
<223> OTHER INFORMATION: Synthetic

<400> SEQUENCE: 33 gccgccagc                                                                9

<210> SEQ ID NO 34
<211> LENGTH: 3
<212> TYPE: PRT
<213> ORGANISM: Artificial Sequence
<220> FEATURE:
<223> OTHER INFORMATION: Synthetic

<400> SEQUENCE: 34

Ala Ala Ser
1

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
cagcagagct acaccacccc cctgacc                                           27

<210> SEQ ID NO 36
<211> LENGTH: 9
<212> TYPE: PRT
<213> ORGANISM: Artificial Sequence
<220> FEATURE:
<223> OTHER INFORMATION: Synthetic

<400> SEQUENCE: 36

Gln Gln Ser Tyr Thr Thr Pro Leu Thr
1               5

<210> SEQ ID NO 37
<211> LENGTH: 1341
<212> TYPE: DNA
<213> ORGANISM: Artificial Sequence
<220> FEATURE:
<223> OTHER INFORMATION: Synthetic

<400> SEQUENCE: 37
gaggtgcagc tggtggagag cggcggcggc ctggtgcagc ccggcggcag cctgaggctg       60
agctgcgccg ccagcggctt caccttcagc agctacgaca tgcactgggt gaggcaggcc      120
accggcaagg gcctggagtg ggtgagcacc atcgacaccg ccggcgacac ctactacccc      180
ggcagcgtga agggcaggtt caccatcagc agggagaacg ccaagaacag cctgtacctg      240
cagatgaaca gcctgagggc cggcgacacc gccgtgtact actgcgccag ggacggcgag      300
ctggagctgc agggctactt cgacctgtgg ggcaggggca cctggtgac cgtgagcagc       360 gccagcacca agggcccag cgtgttcccc ctggcccct gcagcaggag caccagcgag        420
agcaccgccg ccctgggctg cctggtgaag gactacttcc ccgagcccgt gaccgtgagc      480
tggaacagcg gcgccctgac cagcggcgtg cacaccttcc ccgccgtgct gcagagcagc      540
ggcctgtaca gcctgagcag cgtggtgacc gtgcccagca gcagcctggg caccaagacc      600
tacacctgca acgtggacca caagcccagc aacaccaagg tggacaagag ggtggagagc      660
```

```
aagtacggcc cccctgccc ccctgcccc gcccccgagt tcctgggcgg ccccagcgtg    720
ttcctgttcc cccccaagcc caaggacacc ctgatgatca gcaggacccc cgaggtgacc    780
tgcgtggtgg tggacgtgag ccaggaggac cccgaggtgc agttcaactg gtacgtggac    840
ggcgtggagg tgcacaacgc caagaccaag cccagggagg agcagttcaa cagcacctac    900
agggtggtga gcgtgctgac cgtgctgcac caggactggc tgaacggcaa ggagtacaag    960
tgcaaggtga gcaacaaggg cctgcccagc agcatcgaga agaccatcag caaggccaag   1020
ggccagccca gggagcccca ggtgtacacc ctgcccccca gcaggagga gatgaccaag    1080 aaccaggtga gcctgacctg cctggtgaag ggcttctacc ccagcgacat cgccgtggag   1140
tgggagagca acggccagcc cgagaacaac tacaagacca ccccccccgt gctggacagc   1200
gacggcagct tcttcctgta cagcaggctg accgtggaca agagcaggtg gcaggagggc   1260
aacgtgttca gctgcagcgt gatgcacgag gccctgcaca accactacac ccagaagagc   1320
ctgagcctga gcctgggcaa g                                             1341
```

<210> SEQ ID NO 38
<211> LENGTH: 447
<212> TYPE: PRT
<213> ORGANISM: Artificial Sequence
<220> FEATURE:
<223> OTHER INFORMATION: Synthetic

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Thr Ile Asp Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Asp Gly Glu Leu Glu Leu Gln Gly Tyr Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 39
<211> LENGTH: 642
<212> TYPE: DNA
<213> ORGANISM: Artificial Sequence
<220> FEATURE:
<223> OTHER INFORMATION: Synthetic

<400> SEQUENCE: 39

```
gacatccaga tgacccagag ccccagcagc ctgagcgcca gcgtgggcga cagggtgacc        60
atcacctgca gggccagcca gatcatcagc atctacctga actggtacca gcagaagccc       120
ggcaaggccc ccaagctgct gatctacgcc gccagcagcc tgcagagcgg cgtgcccagc       180
aggttcagcg gcagcggcag cggcaccgac ttcaccctga ccatcagcag cctgcagccc       240
gaggacttcg ccacctacta ctgccagcag agctacacca ccccccctga cttcggcggc       300
ggcaccaagg tggagatcaa gaggaccgtg gccgccccca gcgtgttcat cttcccccc        360 agcgacgagc agctgaagag cggcaccgcc agcgtggtgt gcctgctgaa caacttctac       420
cccagggagg ccaaggtgca gtggaaggtg gacaacgccc tgcagagcgg caacagccag       480
gagagcgtga ccgagcagga cagcaaggac agcacctaca gcctgagcag cacccctgacc      540 ctgagcaagg ccgactacga gaagcacaag gtgtacgcct gcgaggtgac ccaccagggc       600
ctgagcagcc ccgtgaccaa gagcttcaac aggggcgagt gc                          642
```

<210> SEQ ID NO 40
<211> LENGTH: 214
<212> TYPE: PRT
<213> ORGANISM: Artificial Sequence
<220> FEATURE:
<223> OTHER INFORMATION: Synthetic

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Ile Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Thr Thr Pro Leu
            85                  90                  95

Thr Phe Gly Gly Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 41
<211> LENGTH: 372
<212> TYPE: DNA
<213> ORGANISM: Artificial Sequence
<220> FEATURE:
<223> OTHER INFORMATION: Synthetic

<400> SEQUENCE: 41
caggtgcagc tggtggagag cggcggcggc gtggtgcagc ccggcaggag cctgaggctg     60
agctgcgtgg ccagcggctt catcctgagc cactacggca tgcactgggt gaggcaggcc    120
cccggcaagg gcctggagtg ggtggccgtg atctggttcg acggcaccaa caagtactac    180
gccgacagcg tgaagggcag gttcaccgtg agcagggaca cagcaagaa caccctgtac     240 atgcagatga acagcctgag ggccgaggac accgccgtgt actactgcgc cagggacccc    300
ccccccgcca ggaggggcaa ctacaacggc atggacgtgt ggggccaggg caccaccgtg    360
accgtgagca gc                                                       372

<210> SEQ ID NO 42
<211> LENGTH: 124
<212> TYPE: PRT
<213> ORGANISM: Artificial Sequence
<220> FEATURE:
<223> OTHER INFORMATION: Synthetic

<400> SEQUENCE: 42

Gln Val Gln Leu Val Glu Ser Gly Gly Gly Val Val Gln Pro Gly Arg

```
            1               5                  10                  15
Ser Leu Arg Leu Ser Cys Val Ala Ser Gly Phe Ile Leu Ser His Tyr
                20                  25                  30
Gly Met His Trp Val Arg Gln Ala Pro Gly Lys Gly Leu Glu Trp Val
                35                  40                  45
Ala Val Ile Trp Phe Asp Gly Thr Asn Lys Tyr Tyr Ala Asp Ser Val
                50                  55                  60
Lys Gly Arg Phe Thr Val Ser Arg Asp Asn Ser Lys Asn Thr Leu Tyr
 65                  70                  75                  80
Met Gln Met Asn Ser Leu Arg Ala Glu Asp Thr Ala Val Tyr Tyr Cys
                85                  90                  95
Ala Arg Asp Pro Pro Ala Arg Arg Gly Asn Tyr Asn Gly Met Asp
                100                 105                 110
Val Trp Gly Gln Gly Thr Thr Val Thr Val Ser Ser
                115                 120

<210> SEQ ID NO 43
<211> LENGTH: 24
<212> TYPE: DNA
<213> ORGANISM: Artificial Sequence
<220> FEATURE:
<223> OTHER INFORMATION: Synthetic

<400> SEQUENCE: 43
ggcttcatcc tgagccacta cggc                                          24

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Gly Phe Ile Leu Ser His Tyr Gly
 1               5

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
atctggttcg acggcaccaa caag                                          24

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Ile Trp Phe Asp Gly Thr Asn Lys
 1               5

<210> SEQ ID NO 47
<211> LENGTH: 51
<212> TYPE: DNA
<213> ORGANISM: Artificial Sequence
<220> FEATURE:
```

<223> OTHER INFORMATION: Synthetic

<400> SEQUENCE: 47
gccagggacc cccccccgc caggaggggc aactacaacg gcatggacgt g        51

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Ala Arg Asp Pro Pro Ala Arg Arg Gly Asn Tyr Asn Gly Met Asp
1               5                   10                  15

Val

<210> SEQ ID NO 49
<211> LENGTH: 321
<212> TYPE: DNA
<213> ORGANISM: Artificial Sequence
<220> FEATURE:
<223> OTHER INFORMATION: Synthetic

<400> SEQUENCE: 49
gacatccaga tgacccagag ccccagcagc ctgagcgcca gcgtgggcga cagggtgacc    60
atcacctgca gggccagcca ggacatcagg aacgacctgg gctggtacca gcagaagccc   120
ggcaaggccc ccaagaggct gatcttcggc gccagcagcc tgcagagcgg cgtgcccctg   180
aggttcagcg gcagcggcag cggcaccgag ttcaccctga ccatcaacaa cctgcagccc   240
gaggacttcg ccaccttcta ctgcctgcag gacaacagct accccctgga cttcggccag   300
ggcaccaagg tggagatcaa g                                              321

<210> SEQ ID NO 50
<211> LENGTH: 107
<212> TYPE: PRT
<213> ORGANISM: Artificial Sequence
<220> FEATURE:
<223> OTHER INFORMATION: Synthetic

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
                20                  25                  30

Leu Gly Trp Tyr Gln Gln Lys Pro Gly Lys Ala Pro Lys Arg Leu Ile
            35                  40                  45

Phe Gly Ala Ser Ser Leu Gln Ser Gly Val Pro Leu Arg Phe Ser Gly
        50                  55                  60

Ser Gly Ser Gly Thr Glu Phe Thr Leu Thr Ile Asn Asn Leu Gln Pro
65                  70                  75                  80

Glu Asp Phe Ala Thr Phe Tyr Cys Leu Gln Asp Asn Ser Tyr Pro Trp
                85                  90                  95

Thr Phe Gly Gln Gly Thr Lys Val Glu Ile Lys
            100                 105

<210> SEQ ID NO 51
<211> LENGTH: 18
<212> TYPE: DNA
<213> ORGANISM: Artificial Sequence

```
<220> FEATURE:
<223> OTHER INFORMATION: Synthetic

<400> SEQUENCE: 51
caggacatca ggaacgac                                                      18

<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

Gln Asp Ile Arg Asn Asp
1               5

<210> SEQ ID NO 53
<211> LENGTH: 9
<212> TYPE: DNA
<213> ORGANISM: Artificial Sequence
<220> FEATURE:
<223> OTHER INFORMATION: Synthetic

<400> SEQUENCE: 53 ggcgccagc                                                                 9

<210> SEQ ID NO 54
<211> LENGTH: 3
<212> TYPE: PRT
<213> ORGANISM: Artificial Sequence
<220> FEATURE:
<223> OTHER INFORMATION: Synthetic

<400> SEQUENCE: 54

Gly Ala Ser
1

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
ctgcaggaca acagctaccc ctggacc                                            27

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Leu Gln Asp Asn Ser Tyr Pro Trp Thr
1               5

<210> SEQ ID NO 57
<211> LENGTH: 1353
<212> TYPE: DNA
<213> ORGANISM: Artificial Sequence
<220> FEATURE:
<223> OTHER INFORMATION: Synthetic

<400> SEQUENCE: 57
```

```
caggtgcagc tggtggagag cggcggcggc gtggtgcagc ccggcaggag cctgaggctg    60
agctgcgtgg ccagcggctt catcctgagc cactacggca tgcactgggt gaggcaggcc   120
cccggcaagg gcctggagtg ggtggccgtg atctggttcg acggcaccaa caagtactac   180
gccgacagcg tgaagggcag gttcaccgtg agcagggaca caagcaagaa caccctgtac   240
atgcagatga acagcctgag ggccgaggac accgccgtgt actactgcgc cagggacccc   300
ccccccgcca ggaggggcaa ctacaacggc atggacgtgt ggggccaggg caccaccgtg   360
accgtgagca gcgccagcac caagggcccc agcgtgttcc ccctggcccc ctgcagcagg   420
agcaccagcg agagcaccgc cgccctgggc tgcctggtga aggactactt ccccgagccc   480
gtgaccgtga gctggaacag cggcgccctg accagcggcg tgcacacctt ccccgccgtg   540
ctgcagagca gcggcctgta cagcctgagc agcgtggtga ccgtgcccag cagcagcctg   600
ggcaccaaga cctacacctg caacgtggac cacaagccca gcaacaccaa ggtggacaag   660
agggtggaga gcaagtacgg ccccccctgc ccccctgcc cgccccga gttcctgggc   720
ggccccagcg tgttcctgtt ccccccaag cccaaggaca ccctgatgat cagcaggacc   780
cccgaggtga cctgcgtggt ggtggacgtg agccaggagg accccgaggt gcagttcaac   840
tggtacgtgg acggcgtgga ggtgcacaac gccaagacca gcccaggga ggagcagttc   900
aacagcacct acagggtggt gagcgtgctg accgtgctgc accaggactg gctgaacggc   960
aaggagtaca agtgcaaggt gagcaacaag ggcctgccca gcagcatcga aaagaccatc  1020
agcaaggcca agggccagcc cagggagccc caggtgtaca ccctgccccc cagccaggag  1080
gagatgacca agaaccaggt gagcctgacc tgcctggtga agggcttcta ccccagcgac  1140
atcgccgtgg agtgggagag caacggccag cccgagaaca actacaagac cacccccccc  1200
gtgctggaca gcgacggcag cttcttcctg tacagcaggc tgaccgtgga caagagcagg  1260
tggcaggagg gcaacgtgtt cagctgcagc gtgatgcacg aggccctgca caaccactac  1320
acccagaaga gcctgagcct gagcctgggc aag                                1353
```

<210> SEQ ID NO 58
<211> LENGTH: 451
<212> TYPE: PRT
<213> ORGANISM: Artificial Sequence
<220> FEATURE:
<223> OTHER INFORMATION: Synthetic

<400> SEQUENCE: 58

```
Gln Val Gln Leu Val Glu Ser Gly Gly Gly Val Val Gln Pro Gly Arg
1               5                  10                  15

Ser Leu Arg Leu Ser Cys Val Ala Ser Gly Phe Ile Leu Ser His Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Met Gln Met Asn Ser Leu Arg Ala Glu Asp Thr Ala Val Tyr Tyr Cys
                85                  90                  95

Ala Arg Asp Pro Pro Ala Arg Arg Gly Asn Tyr Asn Gly Met Asp
            100                 105                 110

Val Trp Gly Gln Gly Thr Thr Val Thr Val Ser Ser Ala Ser Thr Lys
```

115                 120                 125
Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 59
<211> LENGTH: 642
<212> TYPE: DNA
<213> ORGANISM: Artificial Sequence
<220> FEATURE:
<223> OTHER INFORMATION: Synthetic

<400> SEQUENCE: 59
gacatccaga tgacccagag ccccagcagc ctgagcgcca gcgtgggcga cagggtgacc      60
atcacctgca gggccagcca ggacatcagg aacgacctgg gctggtacca gcagaagccc     120

```
ggcaaggccc ccaagaggct gatcttcggc gccagcagcc tgcagagcgg cgtgcccctg    180
aggttcagcg gcagcggcag cggcaccgag ttcaccctga ccatcaacaa cctgcagccc    240
gaggacttcg ccaccttcta ctgcctgcag gacaacagct accccctgga cttcggccag    300
ggcaccaagg tggagatcaa gaggaccgtg gccgccccca gcgtgttcat cttcccccccc  360 agcgacgagc agctgaagag cggcaccgcc agcgtggtgt gcctgctgaa caacttctac    420
cccagggagg ccaaggtgca gtggaaggtg gacaacgccc tgcagagcgg caacagccag    480
gagagcgtga ccgagcagga cagcaaggac agcacctaca gcctgagcag caccctgacc    540
ctgagcaagg ccgactacga gaagcacaag gtgtacgcct gcgaggtgac ccaccagggc    600
ctgagcagcc ccgtgaccaa gagcttcaac agggggcgagt gc                     642
```

<210> SEQ ID NO 60
<211> LENGTH: 214
<212> TYPE: PRT
<213> ORGANISM: Artificial Sequence
<220> FEATURE:
<223> OTHER INFORMATION: Synthetic

<400> SEQUENCE: 60

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Phe Gly Ala Ser Ser Leu Gln Ser Gly Val Pro Arg Phe Ser Gly
    50                  55                  60

Ser Gly Ser Gly Thr Glu Phe Thr Leu Thr Ile Asn Asn Leu Gln Pro
65                  70                  75                  80

Glu Asp Phe Ala Thr Phe Tyr Cys Leu Gln Asp Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 61
<211> LENGTH: 369
<212> TYPE: DNA
<213> ORGANISM: Artificial Sequence
<220> FEATURE:
<223> OTHER INFORMATION: Synthetic

<400> SEQUENCE: 61

```
caggtgcagc tggtggagag cggcggcggc gtggtgcagc ccggcaggag cctgaggctg    60
agctgcgagg ccagcggctt caccttcagc gactacgacc tgcactgggt gaggcaggcc   120
cccggcaagg gcctggagtg ggtggccttc atcagcaacg acggcagcaa cgagtactac   180
cccaagagcg tgaagggcag gttcagcatc agcagggaca cagcaagaa cacccctgtac   240 ctgcagatga acagcctgag ggccgaggac accgccgtgt accactgcac caaggagagg   300
gactactact acgacagcag cggcagcctg gactactggg gccagggcac cctggtgacc   360
gtgagcagc                                                          369
```

<210> SEQ ID NO 62
<211> LENGTH: 123
<212> TYPE: PRT
<213> ORGANISM: Artificial Sequence
<220> FEATURE:
<223> OTHER INFORMATION: Synthetic

<400> SEQUENCE: 62

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Asp Tyr
            20                  25                  30

Asp Leu His Trp Val Arg Gln Ala Pro Gly Lys Gly Leu Glu Trp Val
        35                  40                  45

Ala Phe Ile Ser Asn Asp Gly Ser Asn Glu Tyr Tyr Pro Lys Ser Val
    50                  55                  60

Lys Gly Arg Phe Ser Ile Ser Arg Asp Asn Lys Asn Thr Leu Tyr
65                  70                  75                  80

Leu Gln Met Asn Ser Leu Arg Ala Glu Asp Thr Ala Val Tyr His Cys
                85                  90                  95

Thr Lys Glu Arg Asp Tyr Tyr Tyr Asp Ser Ser Gly Ser Leu Asp Tyr
            100                 105                 110

Trp Gly Gln Gly Thr Leu Val Thr Val Ser Ser
        115                 120
```

<210> SEQ ID NO 63
<211> LENGTH: 24
<212> TYPE: DNA
<213> ORGANISM: Artificial Sequence
<220> FEATURE:
<223> OTHER INFORMATION: Synthetic

<400> SEQUENCE: 63

```
ggcttcacct tcagcgacta cgac                                          24
```

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64

```
Gly Phe Thr Phe Ser Asp Tyr Asp
1               5
```

<210> SEQ ID NO 65
<211> LENGTH: 24
<212> TYPE: DNA
<213> ORGANISM: Artificial Sequence

```
<220> FEATURE:
<223> OTHER INFORMATION: Synthetic

<400> SEQUENCE: 65
atcagcaacg acggcagcaa cgag                                              24

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Ile Ser Asn Asp Gly Ser Asn Glu
1               5

<210> SEQ ID NO 67
<211> LENGTH: 48
<212> TYPE: DNA
<213> ORGANISM: Artificial Sequence
<220> FEATURE:
<223> OTHER INFORMATION: Synthetic

<400> SEQUENCE: 67
accaaggaga gggactacta ctacgacagc agcggcagcc tggactac                    48

<210> SEQ ID NO 68
<211> LENGTH: 16
<212> TYPE: PRT
<213> ORGANISM: Artificial Sequence
<220> FEATURE:
<223> OTHER INFORMATION: Synthetic

<400> SEQUENCE: 68

Thr Lys Glu Arg Asp Tyr Tyr Tyr Asp Ser Ser Gly Ser Leu Asp Tyr
1               5                   10                  15

<210> SEQ ID NO 69
<211> LENGTH: 321
<212> TYPE: DNA
<213> ORGANISM: Artificial Sequence
<220> FEATURE:
<223> OTHER INFORMATION: Synthetic

<400> SEQUENCE: 69
gacatccaga tgacccagag ccccagcagc ctgagcgcca gcgtgggcga cagggtgacc        60
atcacctgca gggccagcca gaccatcaac aactacctga actggtacca gcagaagccc       120
ggcaaggccc ccaagctgct gatctacacc accagcggcc tgcagagcgg cgtgcccagc       180
aggttcagcg gcaggggcag cggcaccgac ttcaccctgg ccatcagcag cctgcagccc       240
gaggacttcg ccacctacta ctgccagcag agctaccaca gccccttcac cttcggcccc       300
ggcaccaagg tggacatcaa g                                                 321

<210> SEQ ID NO 70
<211> LENGTH: 107
<212> TYPE: PRT
<213> ORGANISM: Artificial Sequence
<220> FEATURE:
<223> OTHER INFORMATION: Synthetic

<400> SEQUENCE: 70

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Thr Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Thr Ser Gly Leu Gln Ser Gly Val Pro Ser Arg Phe Ser Gly
    50                  55                  60

Arg Gly Ser Gly Thr Asp Phe Thr Leu Ala Ile Ser Ser Leu Gln Pro
65                  70                  75                  80

Glu Asp Phe Ala Thr Tyr Tyr Cys Gln Gln Ser Tyr His Ser Pro Phe
                85                  90                  95

Thr Phe Gly Pro Gly Thr Lys Val Asp Ile Lys
            100                 105

<210> SEQ ID NO 71
<211> LENGTH: 18
<212> TYPE: DNA
<213> ORGANISM: Artificial Sequence
<220> FEATURE:
<223> OTHER INFORMATION: Synthetic

<400> SEQUENCE: 71
cagaccatca acaactac                                                 18

<210> SEQ ID NO 72
<211> LENGTH: 6
<212> TYPE: PRT
<213> ORGANISM: Artificial Sequence
<220> FEATURE:
<223> OTHER INFORMATION: Synthetic

<400> SEQUENCE: 72

Gln Thr Ile Asn Asn Tyr
1               5

<210> SEQ ID NO 73
<211> LENGTH: 9
<212> TYPE: DNA
<213> ORGANISM: Artificial Sequence
<220> FEATURE:
<223> OTHER INFORMATION: Synthetic

<400> SEQUENCE: 73 accaccagc                                                           9

<210> SEQ ID NO 74
<211> LENGTH: 3
<212> TYPE: PRT
<213> ORGANISM: Artificial Sequence
<220> FEATURE:
<223> OTHER INFORMATION: Synthetic

<400> SEQUENCE: 74

Thr Thr Ser
1

<210> SEQ ID NO 75
<211> LENGTH: 27
<212> TYPE: DNA
<213> ORGANISM: Artificial Sequence
<220> FEATURE:
<223> OTHER INFORMATION: Synthetic

<400> SEQUENCE: 75
cagcagagct accacagccc cttcacc        27

<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Gln Gln Ser Tyr His Ser Pro Phe Thr
1               5

<210> SEQ ID NO 77
<211> LENGTH: 1350
<212> TYPE: DNA
<213> ORGANISM: Artificial Sequence
<220> FEATURE:
<223> OTHER INFORMATION: Synthetic

<400> SEQUENCE: 77
caggtgcagc tggtggagag cggcggcggc gtggtgcagc ccggcaggag cctgaggctg        60
agctgcgagg ccagcggctt caccttcagc gactacgacc tgcactgggt gaggcaggcc       120
cccggcaagg gcctggagtg ggtggccttc atcagcaacg acggcagcaa cgagtactac       180
cccaagagcg tgaagggcag gttcagcatc agcagggaca cagcaagaa caccctgtac       240 ctgcagatga acagcctgag ggccgaggac accgccgtgt accactgcac caaggagagg       300
gactactact acgacagcag cggcagcctg gactactggg gccagggcac cctggtgacc       360
gtgagcagcg ccagcaccaa gggccccagc gtgttccccc tggcccctg cagcaggagc       420 accagcgaga gcaccgccgc cctgggctgc ctggtgaagg actacttccc cgagcccgtg       480
accgtgagct ggaacagcgg cgccctgacc agcggcgtgc acaccttccc cgccgtgctg       540
cagagcagcg gcctgtacag cctgagcagc gtggtgaccg tgcccagcag cagcctgggc       600
accaagacct acacctgcaa cgtggaccac aagcccagca caccaaggt ggacaagagg       660 gtggagagca gtacggccc cccctgcccc cctgccccg cccccgagtt cctgggcggc       720
cccagcgtgt tcctgttccc ccccaagccc aaggacaccc tgatgatcag caggaccccc       780
gaggtgacct gcgtggtggt ggacgtgagc caggaggacc ccgaggtgca gttcaactgg       840
tacgtggacg gcgtggaggt gcacaacgcc aagaccaagc caggaggga gcagttcaac       900 agcacctaca gggtggtgag cgtgctgacc gtgctgcacc aggactggct gaacggcaag       960
gagtacaagt gcaaggtgag caacaagggc ctgcccagca gcatcgagaa gaccatcagc      1020
aaggccaagg gccagcccag ggagccccag gtgtacaccc tgcccccag ccaggaggag      1080 atgaccaaga accaggtgag cctgacctgc ctggtgaagg gcttctaccc cagcgacatc      1140
gccgtggagt gggagagcaa cggccagccc gagaacaact acaagaccac cccccccgtg      1200
ctggacagcg acggcagctt cttcctgtac agcaggctga ccgtggacaa gagcaggtgg      1260
caggagggca acgtgttcag ctgcagcgtg atgcacgagg ccctgcacaa ccactacacc      1320
cagaagagcc tgagcctgag cctgggcaag                                      1350

<210> SEQ ID NO 78
<211> LENGTH: 450
<212> TYPE: PRT
<213> ORGANISM: Artificial Sequence
<220> FEATURE:
<223> OTHER INFORMATION: Synthetic

```
<400> SEQUENCE: 78

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Asp Tyr
            20                  25                  30

Asp Leu His Trp Val Arg Gln Ala Pro Gly Lys Gly Leu Glu Trp Val
        35                  40                  45

Ala Phe Ile Ser Asn Asp Gly Ser Asn Glu Tyr Tyr Pro Lys Ser Val
50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Thr Lys Glu Arg Asp Tyr Tyr Tyr Asp Ser Ser Gly Ser Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415
```

```
Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

```
<210> SEQ ID NO 79
<211> LENGTH: 642
<212> TYPE: DNA
<213> ORGANISM: Artificial Sequence
<220> FEATURE:
<223> OTHER INFORMATION: Synthetic

<400> SEQUENCE: 79
gacatccaga tgacccagag ccccagcagc ctgagcgcca gcgtgggcga cagggtgacc        60
atcacctgca gggccagcca gaccatcaac aactacctga actggtacca gcagaagccc       120
ggcaaggccc ccaagctgct gatctacacc accagcggcc tgcagagcgg cgtgcccagc       180
aggttcagcg gcaggggcag cggcaccgac ttcaccctgg ccatcagcag cctgcagccc       240
gaggacttcg ccacctacta ctgccagcag agctaccaca gccccttcac cttcggcccc       300
ggcaccaagg tggacatcaa gaggaccgtg gccgcccca gcgtgttcat cttcccccc        360 agcgacgagc agctgaagag cggcaccgcc agcgtggtgt gcctgctgaa caacttctac       420
cccagggagg ccaaggtgca gtggaaggtg acaacgccc tgcagagcgg caacagccag        480
gagagcgtga ccgagcagga cagcaaggac agcacctaca gcctgagcag cacctga         540 ctgagcaagg ccgactacga gaagcacaag gtgtacgcct gcgaggtgac ccaccaggc        600 ctgagcagcc ccgtgaccaa gagcttcaac agggcgagt gc                          642
```

```
<210> SEQ ID NO 80
<211> LENGTH: 214
<212> TYPE: PRT
<213> ORGANISM: Artificial Sequence
<220> FEATURE:
<223> OTHER INFORMATION: Synthetic

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Thr Ser Gly Leu Gln Ser Gly Val Pro Ser Arg Phe Ser Gly
    50                  55                  60

Arg Gly Ser Gly Thr Asp Phe Thr Leu Ala Ile Ser Ser Leu Gln Pro
65                  70                  75                  80

Glu Asp Phe Ala Thr Tyr Tyr Cys Gln Gln Ser Tyr His Ser Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 81
<211> LENGTH: 220
<212> TYPE: PRT
<213> ORGANISM: Artificial Sequence
<220> FEATURE:
<223> OTHER INFORMATION: Synthetic

<400> SEQUENCE: 81

Met Glu Leu Gly Leu Gly Gly Leu Ser Thr Leu Ser His Cys Pro Trp
1               5                   10                  15

Pro Arg Gln Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Pro Val Leu Ala Ser Pro Ala Gly His
    50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Pro Ala Pro Pro
                85                  90                  95

Ser Ala Leu Pro Arg Gly Gly Arg Ala Ala Arg Ala Gly Gly Pro Gly
            100                 105                 110

Ser Arg Ala Arg Ala Ala Gly Ala Arg Gly Cys Arg Leu Arg Ser Gln
        115                 120                 125

Leu Val Pro Val Arg Ala Leu Gly Leu Gly His Arg Ser Asp Glu Leu
    130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
        195                 200                 205

Asp Arg Leu Ser Ala Thr Ala Cys Gly Cys Leu Gly
    210                 215                 220

<210> SEQ ID NO 82
<211> LENGTH: 141
<212> TYPE: PRT
<213> ORGANISM: Artificial Sequence
<220> FEATURE:
<223> OTHER INFORMATION: Synthetic

<400> SEQUENCE: 82

Ala Gly Gly Pro Gly Ser Arg Ala Arg Ala Ala Gly Ala Arg Gly Cys
1               5                   10                  15

```
Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly Glu Gln Lys Leu Ile Ser Glu Glu Asp Leu Gly Gly Glu Gln Lys
        115                 120                 125

Leu Ile Ser Glu Glu Asp Leu His His His His His His
    130                 135                 140
```

```
<210> SEQ ID NO 83
<211> LENGTH: 141
<212> TYPE: PRT
<213> ORGANISM: Artificial Sequence
<220> FEATURE:
<223> OTHER INFORMATION: Synthetic

<400> SEQUENCE: 83

Ala Gly Gly Pro Gly Ser Arg Pro Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Pro Gly Ser Arg Pro Ile Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly Glu Gln Lys Leu Ile Ser Glu Glu Asp Leu Gly Gly Glu Gln Lys
        115                 120                 125

Leu Ile Ser Glu Glu Asp Leu His His His His His His
    130                 135                 140
```

```
<210> SEQ ID NO 84
<211> LENGTH: 141
<212> TYPE: PRT
<213> ORGANISM: Artificial Sequence
<220> FEATURE:
<223> OTHER INFORMATION: Synthetic

<400> SEQUENCE: 84

Ala Gly Thr Arg Ser Ser Arg Ala Arg Thr Thr Asp Ala Arg Gly Cys
1               5                   10                  15

Arg Leu Arg Ser Gln Leu Val Pro Val Ser Ala Leu Gly Leu Gly His
            20                  25                  30

Ser Ser Asp Glu Leu Ile Arg Phe Arg Phe Cys Ser Gly Ser Cys Arg
```

```
                 35                  40                  45
Arg Ala Arg Ser Gln His Asp Leu Ser Leu Ala Ser Leu Gly Ala
 50                  55                  60
Gly Ala Leu Arg Ser Pro Pro Gly Ser Arg Pro Ile Ser Gln Pro Cys
 65                  70                  75                  80
Cys Arg Pro Thr Arg Tyr Glu Ala Val Ser Phe Met Asp Val Asn Ser
                 85                  90                  95
Thr Trp Arg Thr Val Asp His Leu Ser Ala Thr Ala Cys Gly Cys Leu
                100                 105                 110
Gly Glu Gln Lys Leu Ile Ser Glu Glu Asp Leu Gly Gly Glu Gln Lys
                115                 120                 125
Leu Ile Ser Glu Glu Asp Leu His His His His His
130                 135                 140

<210> SEQ ID NO 85
<211> LENGTH: 578
<212> TYPE: PRT
<213> ORGANISM: Artificial Sequence
<220> FEATURE:
<223> OTHER INFORMATION: Synthetic

<400> SEQUENCE: 85

Asp Pro Leu Pro Thr Glu Ser Arg Leu Met Asn Ser Cys Leu Gln Ala
 1               5                  10                  15
Arg Arg Lys Cys Gln Ala Asp Pro Thr Cys Ser Ala Ala Tyr His His
                 20                  25                  30
Leu Asp Ser Cys Thr Ser Ser Ile Ser Thr Pro Leu Pro Ser Glu Glu
                 35                  40                  45
Pro Ser Val Pro Ala Asp Cys Leu Glu Ala Ala Gln Gln Leu Arg Asn
 50                  55                  60
Ser Ser Leu Ile Gly Cys Met Cys His Arg Arg Met Lys Asn Gln Val
 65                  70                  75                  80
Ala Cys Leu Asp Ile Tyr Trp Thr Val His Arg Ala Arg Ser Leu Gly
                 85                  90                  95
Asn Tyr Glu Leu Asp Val Ser Pro Tyr Glu Asp Thr Val Thr Ser Lys
                100                 105                 110
Pro Trp Lys Met Asn Leu Ser Lys Leu Asn Met Leu Lys Pro Asp Ser
                115                 120                 125
Asp Leu Cys Leu Lys Phe Ala Met Leu Cys Thr Leu Asn Asp Lys Cys
                130                 135                 140
Asp Arg Leu Arg Lys Ala Tyr Gly Glu Ala Cys Ser Gly Pro His Cys
145                 150                 155                 160
Gln Arg His Val Cys Leu Arg Gln Leu Leu Thr Phe Phe Glu Lys Ala
                165                 170                 175
Ala Glu Pro His Ala Gln Gly Leu Leu Leu Cys Pro Cys Ala Pro Asn
                180                 185                 190
Asp Arg Gly Cys Gly Glu Arg Arg Asn Thr Ile Ala Pro Asn Cys
                195                 200                 205
Ala Leu Pro Pro Val Ala Pro Asn Cys Leu Glu Leu Arg Arg Leu Cys
210                 215                 220
Phe Ser Asp Pro Leu Cys Arg Ser Arg Leu Val Asp Phe Gln Thr His
225                 230                 235                 240
Cys His Pro Met Asp Ile Leu Gly Thr Cys Ala Thr Glu Gln Ser Arg
                245                 250                 255
Cys Leu Arg Ala Tyr Leu Gly Leu Ile Gly Thr Ala Met Thr Pro Asn
```

-continued

```
                260                 265                 270
Phe Val Ser Asn Val Asn Thr Ser Val Ala Leu Ser Cys Thr Cys Arg
            275                 280                 285

Gly Ser Gly Asn Leu Gln Glu Glu Cys Glu Met Leu Glu Gly Phe Phe
            290                 295                 300

Ser His Asn Pro Cys Leu Thr Glu Ala Ile Ala Ala Lys Met Arg Phe
305                 310                 315                 320

His Ser Gln Leu Phe Ser Gln Asp Trp Pro His Pro Thr Phe Ala Val
                325                 330                 335

Met Ala His Gln Asn Glu Asn Pro Ala Val Arg Pro Gln Pro Trp Asp
            340                 345                 350

Lys Thr His Thr Cys Pro Pro Cys Pro Ala Pro Glu Leu Leu Gly Gly
            355                 360                 365

Pro Ser Val Phe Leu Phe Pro Pro Lys Pro Lys Asp Thr Leu Met Ile
        370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Asn Ser Thr Tyr Arg
            420                 425                 430

Val Val Ser Val Leu Thr Val Leu His Gln Asp Trp Leu Asn Gly Lys
            435                 440                 445

Glu Tyr Lys Cys Lys Val Ser Asn Lys Ala Leu Pro Ala Pro Ile Glu
        450                 455                 460

Lys Thr Ile Ser Lys Ala Lys Gly Gln Pro Arg Glu Pro Gln Val Tyr
465                 470                 475                 480

Thr Leu Pro Pro Ser Arg Asp Glu Leu Thr Lys Asn Gln Val Ser Leu
                485                 490                 495

Thr Cys Leu Val Lys Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
            515                 520                 525

Leu Asp Ser Asp Gly Ser Phe Phe Leu Tyr Ser Lys Leu Thr Val Asp
        530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly Lys
```

HUMAN ANTIBODIES TO ARTEMIN AND METHODS OF USE THEREOF

RELATED APPLICATIONS

This application claims priority under 35 U.S.C. 119(e) to U.S. Provisional Patent Application Ser. No. 63/177,369, entitled "HUMAN ANTIBODIES TO ARTEMIN AND METHODS OF USE THEREOF", filed Apr. 20, 2021, the disclosure of which is hereby incorporated by reference in its entirety.

FIELD OF THE INVENTION

The present disclosure relates to human antibodies and antigen-binding fragments of human antibodies that specifically bind to artemin, and methods of use thereof.

SEQUENCE LISTING

An official copy of the sequence listing is submitted concurrently with the specification electronically via EFS-Web as an ASCII formatted sequence listing with a file name of 10907US01_Sequence_Listing_ST25, a creation date of Apr. 19, 2022, and a size of about 69,632 bytes. The sequence listing contained in this ASCII formatted document is part of the specification and is herein incorporated by reference in its entirety.

BACKGROUND

Artemin (ARTN) is a neurotrophic factor that is a member of the glial cell line-derived neurotrophic factor (GDNF) family of ligands. Each GDNF family ligand binds to a glycosylphosphatidylinositol (GPI)-anchored receptor associated with the plasma membrane. This family of receptors is referred to as the GDNF-family receptor alpha (GFRα) family and is composed of four different receptors, GFRα1-4. ARTN binds preferentially to the receptor GFRα3 and is the only known ligand for GFRα3. ARTN and the other GDNF family ligands signal through the RET ("rearranged during transfection") receptor tyrosine kinase, which was first discovered as a proto-oncogene. RET is activated by GDNF family members only if the ligand is first bound to its GFRα receptor (Airaksinen et al, Nature Reviews Neuroscience (2002), 3:383-394).

Both ARTN and GFRα3 are highly expressed during development and are involved in sympathetic nervous system development. In adult mouse, ARTN is expressed in testis, uterus, thyroid, prostate, and epididymis, as well as in olfactory bulbs and arterioles in the intestine and mesentery (Airaksinen et al, Nature Reviews Neuroscience (2002), 3:383-394; Airaksinen et al, Brain, Behavior and Evolution, (2006), 68:181-190). GFRα3 expression in adults is largely restricted to the sensory neurons of the dorsal root ganglia (DRG) (Orozco et al, *European J. Neuroscience*, (2001), 13:2177-2182). Mice lacking ARTN or GFRα3 exhibit abnormalities in the migration and axonal projection pattern of the sympathetic nervous system, resulting in abnormal innervation of target tissues (Honma et al., *Neuron*, (2002), 35:267-282).

A potential role for ARTN and GFRα3 in pain and thermal perception has been shown in several studies. For example, it has been demonstrated that an injection of the artemin protein into the hindpaw of a rodent caused thermal hyperalgesia and this nociception was enhanced when artemin was co-injected with NGF (Malin et al, *J. Neuroscience*, (2006), 26(33): 8588-8599). Other studies showed that artemin mRNA expression was upregulated in a murine inflammatory model, and that artemin transgenic mice have elevated expression of TRPV1 and TRPA1 and increased behavioral sensitivity to heat and cold (Elitt et al, *J. Neuroscience*, (2006), 26(33): 8578-8587). Additionally, artemin and GFRα3 expression are increased in a rat model of migraine (Shang et al., *J Headache Pain*, (2016), 17(1): 81) and in dogs treated with radiotherapy (Nolan et al, *Radiat Res*, (2020), 193(3):241-248). Artemin expression is also increased in tongue mucosa of patients with burning mouth syndrome and in a mouse model of burning mouth syndrome (Shinoda et al., *PAIN*, (2015), 156(12):2528-2537).

SUMMARY OF THE INVENTION

In one aspect, isolated antibodies or antigen-binding fragment thereof that specifically bind to artemin are provided. In some embodiments, the antibody is a monoclonal antibody or an antigen-binding fragment thereof that binds to human artemin. In some embodiments, the antibody or antigen-binding fragment thereof binds to human artemin with a $K_D$ of less than 5 nM as measured by surface plasmon resonance at 25° C.

In some embodiments, the antibody or antigen-binding fragment thereof:

(a) blocks at least 65% of human artemin binding to a solid support coated with human GFRα3 as measured by ELISA;

(b) inhibits or reduces artemin-activated signaling through GFRα3 and RET receptor tyrosine kinase; and/or (c) inhibits or reduces artemin-induced thermal hyperalgesia in vivo.

In some embodiments, the antibody or antigen-binding fragment thereof cross-reacts with artemin from at least one non-human species. In some embodiments, the antibody or antigen-binding fragment thereof cross-reacts with monkey artemin. In some embodiments, the antibody or antigen-binding fragment thereof cross-reacts with mouse artemin.

In some embodiments, the antibody or antigen-binding fragment thereof comprises:

(a) a heavy chain complementarity determining region 1 (HCDR1) comprising an amino acid sequence selected from the group consisting of SEQ ID NOs:4, 24, 44, and 64;

(b) a heavy chain complementarity determining region 2 (HCDR2) comprising an amino acid sequence selected from the group consisting of SEQ ID NOs:6, 26, 46, and 66;

(c) a heavy chain complementarity determining region 3 (HCDR3) comprising an amino acid sequence selected from the group consisting of SEQ ID NOs:8, 28, 48, and 68;

(d) a light chain complementarity determining region 1 (LCDR1) comprising an amino acid sequence selected from the group consisting of SEQ ID NOs:12, 32, 52, and 72;

(e) a light chain complementarity determining region 2 (LCDR2) comprising an amino acid sequence selected from the group consisting of SEQ ID NOs:14, 34, 54, and 74; and (f) a light chain complementarity determining region 3 (LCDR3) comprising an amino acid sequence selected from the group consisting of SEQ ID NOs:16, 36, 56, and 76.

In some embodiments, the antibody or antigen-binding fragment thereof comprises:

(a) an HCDR1 comprising the amino acid sequence of SEQ ID NO:4, an HCDR2 comprising the amino acid sequence of SEQ ID NO:6, an HCDR3 comprising the amino acid sequence of SEQ ID NO:8, an LCDR1 comprising the amino acid sequence of SEQ ID NO:12, an LCDR2 comprising the amino acid sequence of SEQ ID NO:14, and an LCDR3 comprising the amino acid sequence of SEQ ID NO:16; or (b) an HCDR1 comprising the amino acid sequence of SEQ ID NO:24, an HCDR2 comprising the amino acid sequence of SEQ ID NO:26, an HCDR3 comprising the amino acid sequence of SEQ ID NO:28, an LCDR1 comprising the amino acid sequence of SEQ ID NO:32, an LCDR2 comprising the amino acid sequence of SEQ ID NO:34, and an LCDR3 comprising the amino acid sequence of SEQ ID NO:36; or (c) an HCDR1 comprising the amino acid sequence of SEQ ID NO:44, an HCDR2 comprising the amino acid sequence of SEQ ID NO:46, an HCDR3 comprising the amino acid sequence of SEQ ID NO:48, an LCDR1 comprising the amino acid sequence of SEQ ID NO:52, an LCDR2 comprising the amino acid sequence of SEQ ID NO:54, and an LCDR3 comprising the amino acid sequence of SEQ ID NO:56; or (d) an HCDR1 comprising the amino acid sequence of SEQ ID NO:64, an HCDR2 comprising the amino acid sequence of SEQ ID NO:66, an HCDR3 comprising the amino acid sequence of SEQ ID NO:68, an LCDR1 comprising the amino acid sequence of SEQ ID NO:72, an LCDR2 comprising the amino acid sequence of SEQ ID NO:74, and an LCDR3 comprising the amino acid sequence of SEQ ID NO:76.

In some embodiments, the antibody or antigen-binding fragment thereof comprises a heavy chain variable region (HCVR) comprising an amino acid sequence that has at least 85% sequence identity to an amino acid sequence selected from the group consisting of SEQ ID NOs:2, 22, 42, and 62.

In some embodiments, the antibody or antigen-binding fragment thereof comprises a light chain variable region (LCVR) comprising an amino acid sequence that has at least 85% sequence identity to an amino acid sequence selected from the group consisting of SEQ ID NOs:10, 30, 50, and 70.

In some embodiments, the antibody or antigen-binding fragment thereof comprises:

(a) an HCVR comprising the amino acid sequence of SEQ ID NO:2 and an LCVR comprising the amino acid sequence of SEQ ID NO:10; or (b) an HCVR comprising the amino acid sequence of SEQ ID NO:22 and an LCVR comprising the amino acid sequence of SEQ ID NO:30; or (c) an HCVR comprising the amino acid sequence of SEQ ID NO:42 and an LCVR comprising the amino acid sequence of SEQ ID NO:50; or (d) an HCVR comprising the amino acid sequence of SEQ ID NO:62 and an LCVR comprising the amino acid sequence of SEQ ID NO:70.

In some embodiments, the antibody or antigen-binding fragment thereof comprises:

(a) a heavy chain comprising an amino acid sequence having at least 85% sequence identity to the amino acid sequence of SEQ ID NO:18 and a light chain comprising an amino acid sequence having at least 85% sequence identity to the amino acid sequence of SEQ ID NO:20; or (b) a heavy chain comprising an amino acid sequence having at least 85% sequence identity to the amino acid sequence of SEQ ID NO:38 and a light chain comprising an amino acid sequence having at least 85% sequence identity to the amino acid sequence of SEQ ID NO:40; or (c) a heavy chain comprising an amino acid sequence having at least 85% sequence identity to the amino acid sequence of SEQ ID NO:58 and a light chain comprising an amino acid sequence having at least 85% sequence identity to the amino acid sequence of SEQ ID NO:60; or (d) a heavy chain comprising an amino acid sequence having at least 85% sequence identity to the amino acid sequence of SEQ ID NO:78 and a light chain comprising an amino acid sequence having at least 85% sequence identity to the amino acid sequence of SEQ ID NO:80.

In some embodiments, the antibody or antigen-binding fragment thereof comprises heavy chain comprising the amino acid sequence of SEQ ID NO:18 and a light chain comprising the amino acid sequence of SEQ ID NO:20. In some embodiments, the antibody or antigen-binding fragment thereof comprises a heavy chain comprising the amino acid sequence of SEQ ID NO:38 and a light chain comprising the amino acid sequence of SEQ ID NO:40. In some embodiments, the antibody or antigen-binding fragment thereof comprises a heavy chain comprising the amino acid sequence of SEQ ID NO:58 and a light chain comprising the amino acid sequence of SEQ ID NO:60. In some embodiments, the antibody or antigen-binding fragment thereof comprises a heavy chain comprising the amino acid sequence of SEQ ID NO:78 and a light chain comprising the amino acid sequence of SEQ ID NO:80.

In some embodiments, the antibody or antigen-binding fragment thereof is fully human.

In another aspect, pharmaceutical compositions comprising the antibody or antigen-binding fragment thereof and a pharmaceutically acceptable carrier are provided.

In another aspect, nucleic acid molecules comprising a nucleotide sequence encoding the antibody or antigen-binding fragment thereof are provided. In some embodiments, the nucleic acid molecule comprises one or more nucleotide sequences set forth in Table 9.

In yet another aspect, expression vectors and host cells comprising a nucleic acid molecule as disclosed herein are provided, as are methods of producing anti-artemin antibodies using the nucleic acid molecules, expression vectors, and host cells disclosed herein.

In another aspect, methods of inhibiting artemin-activated signaling in a cell are provided. In some embodiments, the method comprises contacting the cell with an antibody or antigen-binding fragment or pharmaceutical composition as disclosed herein, thereby inhibiting artemin-activated signaling in the cell. In some embodiments, the cell is within a subject. In some embodiments, the cell is in vitro or ex vivo.

In another aspect, methods of treating a disease, disorder, or condition associated with artemin expression or activity are provided. In some embodiments, the method comprises administering an antibody or antigen-binding fragment thereof or pharmaceutical composition as disclosed herein to a subject in need thereof (e.g., a subject having the disease, disorder, or condition associated with artemin expression or activity). In some embodiments, the antibody or antigen-binding fragment thereof or pharmaceutical composition is administered to the subject in combination with a second therapeutic agent.

In another aspect, an anti-artemin antibody or antigen-binding fragment thereof, or a pharmaceutical composition comprising an anti-artemin antibody or antigen-binding fragment thereof, is provided for use in a method of treating a disease, disorder, or condition associated with artemin expression or activity. In some embodiments, the method comprises administering an antibody or antigen-binding fragment thereof or pharmaceutical composition as disclosed herein to a subject in need thereof (e.g., a subject having the disease, disorder, or condition associated with artemin expression or activity). In some aspects, the antibody or antigen-binding fragment thereof or pharmaceutical composition is therapeutically combined with a second therapeutic agent. In some aspects, the antibody or antigen-binding fragment thereof or pharmaceutical composition is combined with a second therapeutic agent.

In another aspect, the use of an anti-artemin antibody or antigen-binding fragment thereof, or a pharmaceutical composition comprising an anti-artemin antibody or antigen-binding fragment thereof, in the manufacture of a medicament for use in a method of treating a disease, disorder, or condition associated with artemin expression or activity is provided. In some embodiments, the method comprises administering an antibody or antigen-binding fragment thereof or pharmaceutical composition as disclosed herein to a subject in need thereof (e.g., a subject having the disease, disorder, or condition associated with artemin expression or activity). In some aspects, the antibody or antigen-binding fragment thereof or pharmaceutical composition is therapeutically combined with a second therapeutic agent. In some aspects, the antibody or antigen-binding fragment thereof or pharmaceutical composition is combined with a second therapeutic agent.

In some embodiments, the disease, disorder, or condition is acute pain, chronic pain, neuropathic pain, inflammatory pain, trigeminal neuralgia, postherpetic neuralgia, general neuralgia, visceral pain, osteoarthritis pain, gout, radicular pain, sciatica, back pain, head or neck pain, breakthrough pain, post-surgical pain, chemotherapy induced neuropathic pain, radiotherapy-induced neuropathic pain, radiation-associated pain, or cancer pain. In some embodiments, the disease, disorder, or condition is migraine, cluster headache, chronic headache, or tension headache.

Other embodiments will be apparent from a review of the ensuing detailed description.

BRIEF DESCRIPTION OF THE FIGURES

FIG. 2. Binding of different concentrations of MfArtemin-MMH (cyno Artemin) to Artemin mAb-captured Octet biosensor surface.

DETAILED DESCRIPTION

Definitions

Figure 1:
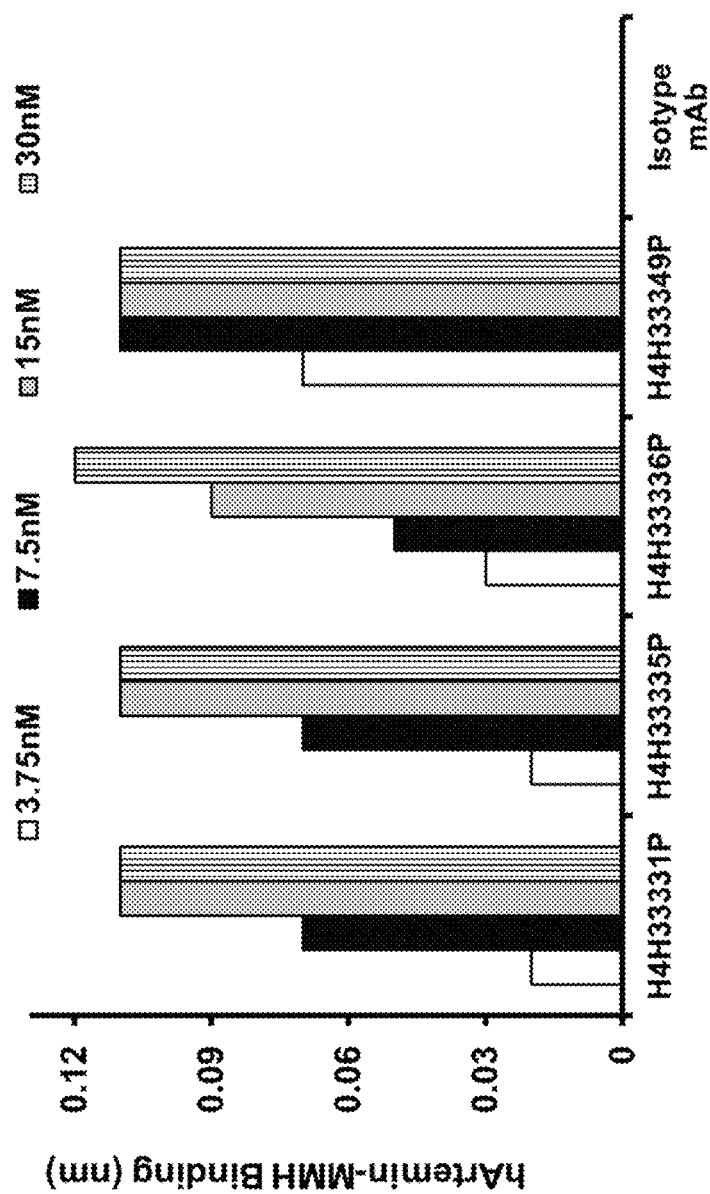
FIG. 1. Binding of different concentrations of hArtemin-MMH (human Artemin) to Artemin mAb-captured Octet biosensor surface.

Before the present invention is described, it is to be understood that the invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

The term "artemin" or "ARTN," as used herein, refers to a glial cell line-derived neurotrophic factor (GDNF) family ligand. See, Baloh et al., Neuron, (1998), 21(6):1291-1302. As used herein, the term "artemin" may refer to a precursor form or a mature (i.e., processed form) such as the full-length processed form or a fragment thereof. In some embodiments, the term "artemin" refers to a human artemin protein or fragment thereof. In some embodiments, the artemin protein comprises the amino acid sequence of human artemin set forth in NCBI Accession No. NP_476432.2, or a fragment thereof (e.g., a proteolytically processed portion). In some embodiments, the artemin protein comprises the amino acid sequence of human artemin set forth in Uniprot Accession No. Q5T4W7, or a fragment thereof (e.g., a proteolytically processed portion), or an isoform thereof. In some embodiments, the artemin protein comprises the amino acid sequence of an artemin protein or fragment set forth in U.S. Pat. No. 6,284,540.

The term "an antibody that binds artemin" or an "anti-artemin antibody" includes antibodies and antigen-binding fragments thereof that specifically recognize a monomeric artemin, as well as antibodies and antigen-binding fragments thereof that specifically recognize a dimeric artemin.

The term "antibody," as used herein, refers to an antigen-binding molecule or molecular complex comprising a set of complementarity determining regions (CDRs) that specifically bind to or interact with a particular antigen (e.g., ARTN). The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In some embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, "antigen-binding domain," and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present disclosure using routine techniques available in the art. For example, the present disclosure includes methods comprising the use of bispecific antibodies wherein one arm of an immunoglobulin is specific for ARTN or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The term "human antibody," as used herein, is intended to include antibodies having variable and constant regions derived from human germline immunoglobulin sequences. The human antibodies of the disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "recombinant antibody," as used herein, is intended to include all antibodies that are prepared, expressed, created or isolated by recombinant means. The term includes, but is not limited to, antibodies expressed using a recombinant expression vector transfected into a host cell (e.g., Chinese hamster ovary (CHO) cell, NS0 cell, BHK cell, or HEK293 cell) or cellular expression system, antibodies isolated from a recombinant, combinatorial human antibody library, and antibodies isolated from a non-human animal (e.g., a mouse, such as a mouse that is transgenic for human immunoglobulin genes (see e.g., Taylor et al. (1992) Nucl. Acids Res. 20:6287-6295). In some embodiments, the recombinant antibody is a recombinant human antibody. In some embodiments, recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

An "isolated antibody" refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less, e.g., $10^{-7}$ M, $10^{-8}$ M, $10^{-9}$ M, $10^{-10}$ M, $10^{-11}$ M, or $10^{-12}$ M (a smaller $K_D$ denotes a tighter binding). Methods for determining whether an antibody specifically binds to an antigen are known in the art and include, for example, equilibrium dialysis, surface plasmon resonance (e.g., BIA-CORE™), bio-layer interferometry assay (e.g., Octet® HTX biosensor), solution-affinity ELISA, and the like. In some embodiments, specific binding is measured in a surface plasmon resonance assay, e.g., at 25° C. or 37° C. An antibody or antigen-binding fragment that specifically binds an antigen from one species may or may not have cross-reactivity to other antigens, such as an orthologous antigen from another species.

The term "$K_D$," as used herein, refers to the equilibrium dissociation constant of a particular antibody-antigen interaction.

The term "surface plasmon resonance," as used herein, refers to an optical phenomenon that allows for the analysis of real-time biomolecular interactions by detection of alterations in protein concentrations within a biosensor matrix, for example using the BIACORE™ system (Cytiva, Marlborough, Mass.).

The term "bio-layer interferometry" or "BLI," as used herein, refers to an optical technique for measuring real-time biomolecular interactions by analyzing interference patterns caused by the binding of one biomolecule dispensed in the sample plate to a second biomolecule immobilized on a biosensor plate, for example using the Octet® system (Sartorius AG, Göttingen, Germany).

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be either linear or discontinuous (e.g., conformational). A linear epitope is one produced by adjacent amino acid residues in a polypeptide chain. A conformational epitope is produced by spatially juxtaposed amino acids from different segments of the linear polypeptide chain. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes may also be defined as structural or functional. Functional epitopes are generally a subset of the structural epitopes and have those residues that directly contribute to the affinity of the interaction. An epitope typically includes at least 3, and more usually, at least 5 or at least 8-10 amino acids in a unique spatial conformation.

Methods for determining the epitope of an antigen-binding protein, e.g., an antibody or antigen-binding fragment, include alanine scanning mutational analysis, peptide blot analysis (Reineke, *Methods Mol Biol* 2004, 248:443-463), peptide cleavage analysis, crystallographic studies, and NMR analysis. In addition, methods such as epitope exclusion, epitope extraction, and chemical modification of antigens can be employed (Tomer, *Prot Sci* 2000, 9:487-496). Another method that can be used to identify the amino acids within a polypeptide with which an antigen-binding protein (e.g., an antibody or antigen-binding fragment) interacts is hydrogen/deuterium exchange detected by mass spectrometry (HDX). See, e.g., Ehring, *Analytical Biochemistry* 1999, 267:252-259; Engen and Smith, *Anal Chem* 2001, 73:256A-265A.

The terms "substantial identity" and "substantially identical," as used with reference to a nucleic acid or fragment thereof, indicates that, when optimally aligned with appropriate nucleotide insertions or deletions with another nucleic acid (or its complementary strand), there is nucleotide sequence identity in at least about 85%, e.g., at least 90%, 91%, 92%, 93%, 94%, 95%, 96%, 97%, 98% or 99%, of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the terms "substantial identity" and "substantially identical" mean that two peptide sequences, when optimally aligned, share at least about 85% sequence identity, e.g., at least 90%, 91%, 92%, 93%, 94%, 95%, 96%, 97%, 98% or 99% sequence identity. In some embodiments, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson, 2000 supra). Another preferred algorithm when comparing a sequence of the disclosure to a database containing a large number of sequences from different organisms is the computer program BLAST, especially BLASTP or TBLASTN, using default parameters. (See, e.g., Altschul et al., 1990, *J. Mol. Biol.* 215: 403-410 and 1997 *Nucleic Acids Res.* 25:3389-3402).

A "variant" of a polypeptide, such an immunoglobulin, VH, VL, heavy chain, light chain, or CDR comprising an amino acid sequence specifically set forth herein, refers to a polypeptide comprising an amino acid sequence that is at least about 70%-99.9% (e.g., at least 70, 75, 80, 85, 90, 91, 92, 93, 94, 95, 96, 97, 98, 99, 99.5, or 99.9%) identical to the reference polypeptide sequence (e.g., as set forth in the sequence listing below), when the comparison is performed by a BLAST algorithm wherein the parameters of the algorithm are selected to give the largest match between the respective sequences over the entire length of the respective reference sequences. In some embodiments, a variant of a polypeptide includes a polypeptide having the amino acid sequence of a reference polypeptide sequence (e.g., as set forth in the sequence listing below) but for one or more (e.g., 1 to 10, or less than 20, or less than 10) missense mutations (e.g., conservative substitutions), nonsense mutations, deletions, or insertions.

The term "therapeutically effective amount" refers to an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

Anti-Artemin Antibodies and Antigen-Binding Fragments Thereof

In one aspect, the present disclosure relates to antibodies and antigen-binding fragments thereof that bind to artemin. Artemin can exist in a precursor form (e.g., a pre-proprotein) or in a proteolytically processed form, for example as described in U.S. Pat. No. 6,284,540, incorporated by reference herein. In some embodiments, the antibody or antigen-binding fragment thereof binds a precursor form of artemin or a fragment thereof. In some embodiments, the antibody or antigen-binding fragment thereof binds a proteolytically processed form of artemin or a fragment thereof.

In some embodiments, the antibody or antigen-binding fragment thereof specifically binds to human artemin (e.g., a human proprotein or a proteolytically processed form). In some embodiments, the antibody or antigen-binding fragment thereof specifically binds to human artemin and cross-reacts with artemin from one or more other non-human species, such as but not limited to mouse, rat, guinea pig, hamster, gerbil, pig, cat, dog, rabbit, goat, sheep, cow, horse, camel, cynomolgus, marmoset, rhesus or chimpanzee artemin. In some embodiments, the antibody or antigen-binding fragment thereof specifically binds to human artemin and cross-reacts with at least some (e.g., some but not all) non-human forms of artemin (e.g., mouse, rat, guinea pig, hamster, gerbil, pig, cat, dog, rabbit, goat, sheep, cow, horse, camel, cynomolgus, marmoset, rhesus or chimpanzee artemin). In some embodiments, the antibody or antigen-binding fragment thereof does not cross-react with artemin from a non-human species.

In some embodiments, the anti-artemin antibody or antigen-binding fragment thereof comprises:
(a) a heavy chain complementarity determining region 1 (HCDR1) comprising an amino acid sequence selected from the group consisting of SEQ ID NOs:4, 24, 44, and 64;
(b) a heavy chain complementarity determining region 2 (HCDR2) comprising an amino acid sequence selected from the group consisting of SEQ ID NOs:6, 26, 46, and 66;
(c) a heavy chain complementarity determining region 3 (HCDR3) comprising an amino acid sequence selected from the group consisting of SEQ ID NOs:8, 28, 48, and 68;
(d) a light chain complementarity determining region 1 (LCDR1) comprising an amino acid sequence selected from the group consisting of SEQ ID NOs:12, 32, 52, and 72;
(e) a light chain complementarity determining region 2 (LCDR2) comprising an amino acid sequence selected from the group consisting of SEQ ID NOs:14, 34, 54, and 74; and
(f) a light chain complementarity determining region 3 (LCDR3) comprising an amino acid sequence selected from the group consisting of SEQ ID NOs:16, 36, 56, and 76.

In some embodiments, the anti-artemin antibody comprises a heavy chain variable region (HCVR) comprising an amino acid sequence that has at least 85%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs:2, 22, 42, and 62. In some embodiments, the anti-artemin antibody comprises an HCVR comprising an amino acid sequence selected from the group consisting of SEQ ID NOs: 2, 22, 42, and 62.

In some embodiments, the anti-artemin antibody comprises a light chain variable region (LCVR) comprising an amino acid sequence that has at least 85%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs:10, 30, 50, and 70. In some embodiments, the anti-artemin antibody comprises an LCVR comprising an amino acid sequence selected from the group consisting of SEQ ID NOs:10, 30, 50, and 70.

In some embodiments, the anti-artemin antibody or antigen-binding fragment thereof comprises:
(a) an HCDR1 comprising the amino acid sequence of SEQ ID NO:4, an HCDR2 comprising the amino acid sequence of SEQ ID NO:6, and an HCDR3 comprising the amino acid sequence of SEQ ID NO:8; or
(b) an HCDR1 comprising the amino acid sequence of SEQ ID NO:24, an HCDR2 comprising the amino acid sequence of SEQ ID NO:26, and an HCDR3 comprising the amino acid sequence of SEQ ID NO:28; or
(c) an HCDR1 comprising the amino acid sequence of SEQ ID NO:44, an HCDR2 comprising the amino acid sequence of SEQ ID NO:46, and an HCDR3 comprising the amino acid sequence of SEQ ID NO:48; or
(d) an HCDR1 comprising the amino acid sequence of SEQ ID NO:64, an HCDR2 comprising the amino acid sequence of SEQ ID NO:66, and an HCDR3 comprising the amino acid sequence of SEQ ID NO:68.

In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:2. In some embodiments, the anti-artemin antibody comprises an HCVR comprising the amino acid sequence of SEQ ID NO:2. In some embodiments, the anti-artemin antibody comprises an HCVR comprising an HCDR1 comprising the amino acid sequence of SEQ ID NO:4, an HCDR2 comprising the amino acid sequence of SEQ ID NO:6, and an HCDR3 comprising the amino acid sequence of SEQ ID NO:8, wherein the HCVR has at least 85%, at least 90%, at least 91%, at least 92%, at least 93%, at least 94%, at least 95%, at least 96%, at least 97%, at least 98%, or at least 99% sequence identity to SEQ ID NO:2. In some embodiments, the anti-artemin antibody comprises a heavy chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:18. In some embodiments, the anti-artemin antibody comprises a heavy chain comprising the amino acid sequence of SEQ ID NO:18.

In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:22. In some embodiments, the anti-artemin antibody comprises an HCVR comprising the amino acid sequence of SEQ ID NO:22. In some embodiments, the anti-artemin antibody comprises an HCVR comprising an HCDR1 comprising the amino acid sequence of SEQ ID NO:24, an HCDR2 comprising the amino acid sequence of SEQ ID NO:26, and an HCDR3 comprising the amino acid sequence of SEQ ID NO:28, wherein the HCVR has at least 85%, at least 90%, at least 91%, at least 92%, at least 93%, at least 94%, at least 95%, at least 96%, at least 97%, at least 98%, or at least 99% sequence identity to SEQ ID NO:22. In some embodiments, the anti-artemin antibody comprises a heavy chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:38. In some embodiments, the anti-artemin antibody comprises a heavy chain comprising the amino acid sequence of SEQ ID NO:38.

In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:42. In some embodiments, the anti-artemin antibody comprises an HCVR comprising the amino acid sequence of SEQ ID NO:42. In some embodiments, the anti-artemin antibody comprises an HCVR comprising an HCDR1 comprising the amino acid sequence of SEQ ID NO:44, an HCDR2 comprising the amino acid sequence of SEQ ID NO:46, and an HCDR3 comprising the amino acid sequence of SEQ ID NO:48, wherein the HCVR has at least 85%, at least 90%, at least 91%, at least 92%, at least 93%, at least 94%, at least 95%, at least 96%, at least 97%, at least 98%, or at least 99% sequence identity to SEQ ID NO:42. In some embodiments, the anti-artemin antibody comprises a heavy chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:58. In some embodiments, the anti-artemin antibody comprises a heavy chain comprising the amino acid sequence of SEQ ID NO:58.

In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:62. In some embodiments, the anti-artemin antibody comprises an HCVR comprising the amino acid sequence of SEQ ID NO:62. In some embodiments, the anti-artemin antibody comprises an HCVR comprising an HCDR1 comprising the amino acid sequence of SEQ ID NO:64, an HCDR2 comprising the amino acid sequence of SEQ ID NO:66, and an HCDR3 comprising the amino acid sequence of SEQ ID NO:68, wherein the HCVR has at least 85%, at least 90%, at least 91%, at least 92%, at least 93%, at least 94%, at least 95%, at least 96%, at least 97%, at least 98%, or at least 99% sequence identity to SEQ ID NO:62. In some embodiments, the anti-artemin antibody comprises a heavy chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:78. In some embodiments, the anti-artemin antibody comprises a heavy chain comprising the amino acid sequence of SEQ ID NO:78.

In some embodiments, the anti-artemin antibody or antigen-binding fragment thereof comprises:

(a) an LCDR1 comprising the amino acid sequence of SEQ ID NO:12, an LCDR2 comprising the amino acid sequence of SEQ ID NO:14, and an LCDR3 comprising the amino acid sequence of SEQ ID NO:16; or (b) an LCDR1 comprising the amino acid sequence of SEQ ID NO:32, an LCDR2 comprising the amino acid sequence of SEQ ID NO:34, and an LCDR3 comprising the amino acid sequence of SEQ ID NO:36; or (c) an LCDR1 comprising the amino acid sequence of SEQ ID NO:52, an LCDR2 comprising the amino acid sequence of SEQ ID NO:54, and an LCDR3 comprising the amino acid sequence of SEQ ID NO:56; or (d) an LCDR1 comprising the amino acid sequence of SEQ ID NO:72, an LCDR2 comprising the amino acid sequence of SEQ ID NO:74, and an LCDR3 comprising the amino acid sequence of SEQ ID NO:76.

In some embodiments, the anti-artemin antibody comprises an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:10. In some embodiments, the anti-artemin antibody comprises an LCVR comprising the amino acid sequence of SEQ ID NO:10. In some embodiments, the anti-artemin antibody comprises an LCVR comprising an LCDR1 comprising the amino acid sequence of SEQ ID NO:12, an LCDR2 comprising the amino acid sequence of SEQ ID NO:14, and an LCDR3 comprising the amino acid sequence of SEQ ID NO:16, wherein the LCVR has at least 85%, at least 90%, at least 91%, at least 92%, at least 93%, at least 94%, at least 95%, at least 96%, at least 97%, at least 98%, or at least 99% sequence identity to SEQ ID NO:10. In some embodiments, the anti-artemin antibody comprises a light chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:20. In some embodiments, the anti-artemin antibody comprises a light chain comprising the amino acid sequence of SEQ ID NO:20.

In some embodiments, the anti-artemin antibody comprises an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:30. In some embodiments, the anti-artemin antibody comprises an LCVR comprising the amino acid sequence of SEQ ID NO:30. In some embodiments, the anti-artemin antibody comprises an LCVR comprising an LCDR1 comprising the amino acid sequence of SEQ ID NO:32, an LCDR2 comprising the amino acid sequence of SEQ ID NO:34, and an LCDR3 comprising the amino acid sequence of SEQ ID NO:36, wherein the LCVR has at least 85%, at least 90%, at least 91%, at least 92%, at least 93%, at least 94%, at least 95%, at least 96%, at least 97%, at least 98%, or at least 99% sequence identity to SEQ ID NO:30. In some embodiments, the anti-artemin antibody comprises a light chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:40. In some embodiments, the anti-artemin antibody comprises a light chain comprising the amino acid sequence of SEQ ID NO:40.

In some embodiments, the anti-artemin antibody comprises an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:50. In some embodiments, the anti-artemin antibody comprises an LCVR comprising the amino acid sequence of SEQ ID NO:50. In some embodiments, the anti-artemin antibody comprises an LCVR comprising an LCDR1 comprising the amino acid sequence of SEQ ID NO:52, an LCDR2 comprising the amino acid sequence of SEQ ID NO:54, and an LCDR3 comprising the amino acid sequence of SEQ ID NO:56, wherein the LCVR has at least 85%, at least 90%, at least 91%, at least 92%, at least 93%, at least 94%, at least 95%, at least 96%, at least 97%, at least 98%, or at least 99% sequence identity to SEQ ID NO:50. In some embodiments, the anti-artemin antibody comprises a light chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:60. In some embodiments, the anti-artemin antibody comprises a light chain comprising the amino acid sequence of SEQ ID NO:60.

In some embodiments, the anti-artemin antibody comprises an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:70. In some embodiments, the anti-artemin antibody comprises an LCVR comprising the amino acid sequence of SEQ ID NO:70. In some embodiments, the anti-artemin antibody comprises an LCVR comprising an LCDR1 comprising the amino acid sequence of SEQ ID NO:72, an LCDR2 comprising the amino acid sequence of SEQ ID NO:74, and an LCDR3 comprising the amino acid sequence of SEQ ID NO:76, wherein the LCVR has at least 85%, at least 90%, at least 91%, at least 92%, at least 93%, at least 94%, at least 95%, at least 96%, at least 97%, at least 98%, or at least 99% sequence identity to SEQ ID NO:70. In some embodiments, the anti-artemin antibody comprises a light chain comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:80. In some embodiments, the anti-artemin antibody comprises a light chain comprising the amino acid sequence of SEQ ID NO:80.

In some embodiments, the anti-artemin antibody comprises an HCDR1 comprising the amino acid sequence of SEQ ID NO:4, an HCDR2 comprising the amino acid sequence of SEQ ID NO:6, an HCDR3 comprising the amino acid sequence of SEQ ID NO:8, an LCDR1 comprising the amino acid sequence of SEQ ID NO:12, an LCDR2 comprising the amino acid sequence of SEQ ID NO:14, and an LCDR3 comprising the amino acid sequence of SEQ ID NO:16. In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:2 and an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:10. In some embodiments, the anti-artemin antibody comprises an HCVR comprising the amino acid sequence of SEQ ID NO:2 and an LCVR comprising the amino acid sequence of SEQ ID NO:10. In some embodiments, the anti-artemin antibody comprises a heavy chain comprising the amino acid sequence of SEQ ID NO:18 and a light chain comprising the amino acid sequence of SEQ ID NO:20.

In some embodiments, the anti-artemin antibody comprises an HCDR1 comprising the amino acid sequence of SEQ ID NO:24, an HCDR2 comprising the amino acid sequence of SEQ ID NO:26, an HCDR3 comprising the amino acid sequence of SEQ ID NO:28, an LCDR1 comprising the amino acid sequence of SEQ ID NO:32, an LCDR2 comprising the amino acid sequence of SEQ ID NO:34, and an LCDR3 comprising the amino acid sequence of SEQ ID NO:36. In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:22 and an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:30. In some embodiments, the anti-artemin antibody comprises an HCVR comprising the amino acid sequence of SEQ ID NO:22 and an LCVR comprising the amino acid sequence of SEQ ID NO:30. In some embodiments, the anti-artemin antibody comprises a heavy chain comprising the amino acid sequence of SEQ ID NO:38 and a light chain comprising the amino acid sequence of SEQ ID NO:40.

In some embodiments, the anti-artemin antibody comprises an HCDR1 comprising the amino acid sequence of SEQ ID NO:44, an HCDR2 comprising the amino acid sequence of SEQ ID NO:46, an HCDR3 comprising the amino acid sequence of SEQ ID NO:48, an LCDR1 comprising the amino acid sequence of SEQ ID NO:52, an LCDR2 comprising the amino acid sequence of SEQ ID NO:54, and an LCDR3 comprising the amino acid sequence of SEQ ID NO:56. In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:42 and an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:50. In some embodiments, the anti-artemin antibody comprises an HCVR comprising the amino acid sequence of SEQ ID NO:42 and an LCVR comprising the amino acid sequence of SEQ ID NO:50. In some embodiments, the anti-artemin antibody comprises a heavy chain comprising the amino acid sequence of SEQ ID NO:58 and a light chain comprising the amino acid sequence of SEQ ID NO:60.

In some embodiments, the anti-artemin antibody comprises an HCDR1 comprising the amino acid sequence of SEQ ID NO:64, an HCDR2 comprising the amino acid sequence of SEQ ID NO:66, an HCDR3 comprising the amino acid sequence of SEQ ID NO:68, an LCDR1 comprising the amino acid sequence of SEQ ID NO:72, an LCDR2 comprising the amino acid sequence of SEQ ID NO:74, and an LCDR3 comprising the amino acid sequence of SEQ ID NO:76. In some embodiments, the anti-artemin antibody comprises an HCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:62 and an LCVR comprising an amino acid sequence that has at least 85%, at least 90%, at least 91%, at least 92%, at least 93%, at least 94%, at least 95%, at least 96%, at least 97%, at least 98%, or at least 99% sequence identity to SEQ ID NO:70. In some embodiments, the anti-artemin antibody comprises an HCVR comprising the amino acid sequence of SEQ ID NO:62 and an LCVR comprising the amino acid sequence of SEQ ID NO:70. In some embodiments, the anti-artemin antibody comprises a heavy chain comprising the amino acid sequence of SEQ ID NO:78 and a light chain comprising the amino acid sequence of SEQ ID NO:80.

In some embodiments, the antibody or antigen-binding fragment thereof binds to a monomeric form of artemin. In some embodiments, the antibody or antigen-binding fragment thereof binds to a dimeric form of artemin. In some embodiments, the antibody or antigen-binding fragment thereof binds to a mature form of the artemin protein (e.g., amino acids 108-220 of SEQ ID NO:81).

In some embodiments, the anti-artemin antibodies or antigen-binding fragments of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second binding specificity.

Sequence Variants

The antibodies or antigen-binding fragments of the present disclosure may comprise one or more amino acid substitutions, insertions, and/or deletions in the framework and/or CDR regions of the heavy and/or light chain variable domains as compared to the corresponding germline sequences from which the individual antibodies were derived. Such mutations can be readily ascertained by comparing the amino acid sequences disclosed herein to germ line sequences available from, for example, public antibody sequence databases. The antibodies of the present disclosure may comprise antigen binding fragments which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germ line sequence from which the antibody was originally derived). Furthermore, the antibodies or antigen-binding fragments may contain any combination of two or more germline mutations within the framework and/or CDR regions, e.g., wherein certain individual residues are mutated to the corresponding residue of a particular germ line sequence while certain other residues that differ from the original germ line sequence are maintained or are mutated to the corresponding residue of a different germline sequence. Once obtained, antibodies or antigen-binding fragments that contain one or more germline mutations can be easily tested for one or more desired property such as, improved binding specificity, increased binding affinity, improved or enhanced antagonistic or agonistic biological properties, reduced immunogenicity, etc. Antibodies and antigen-binding fragments obtained in this general manner are encompassed within the present disclosure.

The present disclosure also includes antibodies or antigen-binding fragments that comprise variants of any of the HCVR, LCVR, and/or CDR amino acid sequences disclosed herein having one or more conservative substitutions. For example, the present disclosure includes antibodies or antigen-binding fragments comprising HCVR, LCVR, and/or CDR amino acid sequences with, e.g., 10 or fewer, 9 or fewer, 8 or fewer, 7 or fewer, 6 or fewer, 5 or fewer, 4 or fewer, 3 or fewer, 2 or fewer, or 1 conservative amino acid substitution(s) relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

The present disclosure also includes antibodies or antigen-binding fragments comprising an HCVR, LCVR, and/or CDR amino acid sequence that is substantially identical to any of the HCVR, LCVR, and/or CDR amino acid sequences disclosed herein. In some embodiments, an antigen-binding molecule comprises HCVR, LCVR, and/or CDR amino acid sequence having at least 85% sequence identity, e.g., at least 90%, at least 91%, at least 92%, at least 93%, at least 94%, at least 95%, at least 96%, at least 97%, at least 98% or at least 99% sequence identity, to a sequence disclosed in Table 1, Table 2, or Table 9. In some embodiments, an antigen-binding molecule comprises HCVR, LCVR, and/or CDR amino acid sequence having at least 85% sequence identity, e.g., at least 90%, at least 91%, at least 92%, at least 93%, at least 94%, at least 95%, at least 96%, at least 97%, at least 98% or at least 99% sequence identity, to a sequence disclosed in Table 1, Table 2, or Table 9, wherein the differences in the amino acid residue(s) relative to the sequence disclosed in Table 1, Table 2, or Table 9 are conservative substitutions or moderately conservative substitutions.

In some embodiments, the antibody or antigen-binding fragment thereof is chimeric, humanized, or fully human. In some embodiments, the antibody or antigen-binding fragment thereof is humanized. In some embodiments, the antibody or antigen-binding fragment thereof is fully human.

Antibodies Comprising Fc Variants

In some embodiments, anti-artemin antibodies or antigen-binding fragments thereof are provided which comprise an Fc domain comprising one or more mutations that enhance or diminish antibody binding to the FcRn receptor, e.g., at acidic pH as compared to neutral pH. For example, the present disclosure includes antibodies or antigen-binding fragments comprising one or more mutations in the CH2 and/or CH3 region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

As a non-limiting example, the present disclosure includes anti-artemin antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Polynucleotides, Vectors, and Host Cells

In another aspect, the present disclosure provides nucleic acid molecules comprising one or more polynucleotide sequences encoding the antibodies or antigen-binding fragments disclosed herein, as well as vectors (e.g., expression vectors) encoding such polynucleotide sequences and host cells into which such vectors have been introduced.

In some embodiments, the nucleic acid molecule comprises one or more polynucleotide sequences encoding an antibody or antigen-binding fragment disclosed in Table 1 or Table 9. In some embodiments, the nucleic acid molecule comprises one or more polynucleotide sequences set forth in Table 2 or Table 9.

In some embodiments, the nucleic acid molecule comprises a polynucleotide sequence that encodes an HCVR comprising the HCDR1, HCDR2, and HCDR3 of SEQ ID NOs:4, 6, and 8, respectively. In some embodiments, the nucleic acid molecule comprises a polynucleotide sequence that encodes an HCVR comprising the sequence of SEQ ID NO:2. In some embodiments, the nucleic acid molecule comprises the polynucleotide sequences of SEQ ID NOs:3, 5, and 7. In some embodiments, the nucleic acid molecule comprises the polynucleotide sequence of SEQ ID NO:1 or has at least 90% sequence identity (e.g., at least 91%, at least 92%, at least 93%, at least 94%, at least 95%, at least 96%, at least 97%, at least 98%, or at least 99% sequence identity) to SEQ ID NO:1. In some embodiments, the nucleic acid molecule comprises the polynucleotide sequence of SEQ ID NO:17 or has at least 90% sequence identity (e.g., at least 91%, at least 92%, at least 93%, at least 94%, at least 95%, at least 96%, at least 97%, at least 98%, or at least 99% sequence identity) to SEQ ID NO:17.

In some embodiments, the nucleic acid molecule comprises a polynucleotide sequence that encodes an HCVR comprising the HCDR1, HCDR2, and HCDR3 of SEQ ID NOs:24, 26, and 28, respectively. In some embodiments, the nucleic acid molecule comprises a polynucleotide sequence that encodes an HCVR comprising the sequence of SEQ ID NO:22. In some embodiments, the nucleic acid molecule comprises the polynucleotide sequences of SEQ ID NOs:23, 25, and 27. In some embodiments, the nucleic acid molecule comprises the polynucleotide sequence of SEQ ID NO:21 or has at least 90% sequence identity (e.g., at least 91%, at least 92%, at least 93%, at least 94%, at least 95%, at least 96%, at least 97%, at least 98%, or at least 99% sequence identity) to SEQ ID NO:21. In some embodiments, the nucleic acid molecule comprises the polynucleotide sequence of SEQ ID NO:37 or has at least 90% sequence identity (e.g., at least 91%, at least 92%, at least 93%, at least 94%, at least 95%, at least 96%, at least 97%, at least 98%, or at least 99% sequence identity) to SEQ ID NO:37.

In some embodiments, the nucleic acid molecule comprises a polynucleotide sequence that encodes an HCVR comprising the HCDR1, HCDR2, and HCDR3 of SEQ ID NOs:44, 46, and 48, respectively. In some embodiments, the nucleic acid molecule comprises a polynucleotide sequence that encodes an HCVR comprising the sequence of SEQ ID NO:42. In some embodiments, the nucleic acid molecule comprises the polynucleotide sequences of SEQ ID NOs:43, 45, and 47. In some embodiments, the nucleic acid molecule comprises the polynucleotide sequence of SEQ ID NO:41 or has at least 90% sequence identity (e.g., at least 91%, at least 92%, at least 93%, at least 94%, at least 95%, at least 96%, at least 97%, at least 98%, or at least 99% sequence identity) to SEQ ID NO:41. In some embodiments, the nucleic acid molecule comprises the polynucleotide sequence of SEQ ID NO:57 or has at least 90% sequence identity (e.g., at least 91%, at least 92%, at least 93%, at least 94%, at least 95%, at least 96%, at least 97%, at least 98%, or at least 99% sequence identity) to SEQ ID NO:57.

In some embodiments, the nucleic acid molecule comprises a polynucleotide sequence that encodes an HCVR comprising the HCDR1, HCDR2, and HCDR3 of SEQ ID NOs:64, 66, and 68, respectively. In some embodiments, the nucleic acid molecule comprises a polynucleotide sequence that encodes an HCVR comprising the sequence of SEQ ID NO:62. In some embodiments, the nucleic acid molecule comprises the polynucleotide sequences of SEQ ID NOs:63, 65, and 67. In some embodiments, the nucleic acid molecule comprises the polynucleotide sequence of SEQ ID NO:61 or has at least 90% sequence identity (e.g., at least 91%, at least 92%, at least 93%, at least 94%, at least 95%, at least 96%, at least 97%, at least 98%, or at least 99% sequence identity) to SEQ ID NO:61. In some embodiments, the nucleic acid molecule comprises the polynucleotide sequence of SEQ ID NO:77 or has at least 90% sequence identity (e.g., at least 91%, at least 92%, at least 93%, at least 94%, at least 95%, at least 96%, at least 97%, at least 98%, or at least 99% sequence identity) to SEQ ID NO:77.

In some embodiments, the nucleic acid molecule comprises a polynucleotide sequence that encodes an LCVR comprising the LCDR1, LCDR2, and LCDR3 of SEQ ID NOs:12, 14, and 16, respectively. In some embodiments, the nucleic acid molecule comprises a polynucleotide sequence that encodes an LCVR comprising the sequence of SEQ ID NO:10. In some embodiments, the nucleic acid molecule comprises the polynucleotide sequences of SEQ ID NOs:11, 13, and 15. In some embodiments, the nucleic acid molecule comprises the polynucleotide sequence of SEQ ID NO:9 or has at least 90% sequence identity (e.g., at least 91%, at least 92%, at least 93%, at least 94%, at least 95%, at least 96%, at least 97%, at least 98%, or at least 99% sequence identity) to SEQ ID NO:9. In some embodiments, the nucleic acid molecule comprises the polynucleotide sequence of SEQ ID NO:19 or has at least 90% sequence identity (e.g., at least 91%, at least 92%, at least 93%, at least 94%, at least 95%, at least 96%, at least 97%, at least 98%, or at least 99% sequence identity) to SEQ ID NO:19.

In some embodiments, the nucleic acid molecule comprises a polynucleotide sequence that encodes an LCVR comprising the LCDR1, LCDR2, and LCDR3 of SEQ ID NOs:32, 34, and 36, respectively. In some embodiments, the nucleic acid molecule comprises a polynucleotide sequence that encodes an LCVR comprising the sequence of SEQ ID NO:30. In some embodiments, the nucleic acid molecule comprises the polynucleotide sequences of SEQ ID NOs:31, 33, and 35. In some embodiments, the nucleic acid molecule comprises the polynucleotide sequence of SEQ ID NO:29 or has at least 90% sequence identity (e.g., at least 91%, at least 92%, at least 93%, at least 94%, at least 95%, at least 96%, at least 97%, at least 98%, or at least 99% sequence identity) to SEQ ID NO:29. In some embodiments, the nucleic acid molecule comprises the polynucleotide sequence of SEQ ID NO:39 or has at least 90% sequence identity (e.g., at least 91%, at least 92%, at least 93%, at least 94%, at least 95%, at least 96%, at least 97%, at least 98%, or at least 99% sequence identity) to SEQ ID NO:39.

In some embodiments, the nucleic acid molecule comprises a polynucleotide sequence that encodes an LCVR comprising the LCDR1, LCDR2, and LCDR3 of SEQ ID NOs:52, 54, and 56, respectively. In some embodiments, the nucleic acid molecule comprises a polynucleotide sequence that encodes an LCVR comprising the sequence of SEQ ID NO:50. In some embodiments, the nucleic acid molecule comprises the polynucleotide sequences of SEQ ID NOs:51, 53, and 55. In some embodiments, the nucleic acid molecule comprises the polynucleotide sequence of SEQ ID NO:49 or has at least 90% sequence identity (e.g., at least 91%, at least 92%, at least 93%, at least 94%, at least 95%, at least 96%, at least 97%, at least 98%, or at least 99% sequence identity) to SEQ ID NO:49. In some embodiments, the nucleic acid molecule comprises the polynucleotide sequence of SEQ ID NO:59 or has at least 90% sequence identity (e.g., at least 91%, at least 92%, at least 93%, at least 94%, at least 95%, at least 96%, at least 97%, at least 98%, or at least 99% sequence identity) to SEQ ID NO:59.

In some embodiments, the nucleic acid molecule comprises a polynucleotide sequence that encodes an LCVR comprising the LCDR1, LCDR2, and LCDR3 of SEQ ID NOs:72, 74, and 76, respectively. In some embodiments, the nucleic acid molecule comprises a polynucleotide sequence that encodes an LCVR comprising the sequence of SEQ ID NO:70. In some embodiments, the nucleic acid molecule comprises the polynucleotide sequences of SEQ ID NOs:71, 73, and 75. In some embodiments, the nucleic acid molecule comprises the polynucleotide sequence of SEQ ID NO:69 or has at least 90% sequence identity (e.g., at least 91%, at least 92%, at least 93%, at least 94%, at least 95%, at least 96%, at least 97%, at least 98%, or at least 99% sequence identity) to SEQ ID NO:69. In some embodiments, the nucleic acid molecule comprises the polynucleotide sequence of SEQ ID NO:79 or has at least 90% sequence identity (e.g., at least 91%, at least 92%, at least 93%, at least 94%, at least 95%, at least 96%, at least 97%, at least 98%, or at least 99% sequence identity) to SEQ ID NO:79.

In some embodiments, compositions are provided comprising one or more nucleic acid molecules as disclosed herein (e.g., a first nucleic acid molecule comprising a polynucleotide sequence encoding an HCVR of an anti-artemin antibody, and a second nucleic acid molecule comprising a polynucleotide sequence encoding an LCVR of an anti-artemin antibody).

The present disclosure also provides recombinant expression vectors carrying one or more nucleic acid molecules as disclosed herein, as well as host cells into which such vectors have been introduced. In some embodiments, two or more expression vectors are provided (e.g., a first expression vector comprising a first nucleic acid molecule comprising a polynucleotide sequence encoding an HCVR of an anti-artemin antibody, and a second expression vector comprising a second nucleic acid molecule comprising a polynucleotide sequence encoding an LCVR of an anti-artemin antibody). In some embodiments, an expression vector comprises two or more nucleic acid molecules (e.g., an expression vector comprising (i) a first nucleic acid molecule comprising a polynucleotide sequence encoding an HCVR of an anti-artemin antibody and (ii) a second nucleic acid molecule comprising a polynucleotide sequence encoding an LCVR of an anti-artemin antibody). Also provided herein are methods of producing anti-artemin antibodies or antigen-binding fragments using the nucleic acid sequences and/or vectors as described herein. In some embodiments, the method of producing the antibody or antigen-binding fragment thereof comprises culturing a host cell comprising one or more nucleic acid sequences and/or expression vectors as described herein under conditions permitting production of the antibodies or antigen-binding fragments, and recovering the antibodies or antigen-binding fragments so produced.

In some embodiments, a host cell comprising one or more nucleic acid sequences and/or vectors as described herein is a prokaryotic cell (e.g., *E. coli*). In some embodiments, the host cell is a eukaryotic cell, such as a non-human mammalian cell (e.g., a Chinese Hamster Ovary (CHO) cell, NS0 cell, BHK cell, or HEK293 cell). Also provided herein are methods of producing anti-artemin antibodies or antigen-binding fragments by culturing the host cells under conditions permitting production of the antibodies or antigen-binding fragments, and recovering the antibodies or antigen-binding fragments so produced.

Characterization of Anti-Artemin Antibodies

The present disclosure includes antibodies and antigen-binding fragments thereof that bind to human artemin with high affinity. In some embodiments, the present disclosure includes antibodies and antigen-binding fragments thereof that bind human ARTN (e.g., at 25° C.) with a $K_D$ of less than about 5 nM as measured by surface plasmon resonance or bio-layer interferometry, e.g., using an assay format as defined in Example 2 herein. In some embodiments, the human ARTN is a mature form of ARTN, e.g., amino acids 108-220 of the human ARTN protein sequence set forth in SEQ ID NO:81. In certain embodiments, the antibodies or antigen-binding fragments of the present disclosure bind human ARTN with a $K_D$ of less than about 5 nM, less than about 1 nM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured by surface plasmon resonance e.g., using an assay format as defined in Example 2 herein, or a substantially similar assay.

In some embodiments, the present disclosure includes antibodies and antigen-binding fragments thereof that bind human ARTN with a dissociative half-life (t½) of greater than about 30 minutes as measured by surface plasmon resonance or bio-layer interferometry at 25° C., e.g., using an assay format as defined in Example 2 herein, or a substantially similar assay. In certain embodiments, the antibodies or antigen-binding fragments of the present disclosure bind human ARTN with a t½ of greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 150 minutes, greater than about 200 minutes, greater than about 250 minutes, or greater than about 300 minutes, as measured by surface plasmon resonance at 25° C., e.g., using an assay format as defined in Example 2 herein, or a substantially similar assay.

In some embodiments, the present disclosure includes antibodies and antigen-binding fragments thereof that block ARTN protein from binding to GFRα3. In some embodiments, the present disclosure includes antibodies and antigen-binding fragments thereof that block monomeric ARTN (e.g., human, cynomolgus monkey, and/or mouse ARTN) protein binding to human GFRα3, as measured by a blocking ELISA assay, e.g., using an assay format as defined in Example 2 herein, or a substantially similar assay. In certain embodiments, the antibodies or antigen-binding fragments of the present disclosure block at least 50%, at least 60%, at least 70%, at least 75%, at least 80%, at least 85%, or at least 90% of human ARTN binding to human GFRα3 as measured by blocking ELISA, e.g., using an assay format as defined in Example 3 herein, or a substantially similar assay.

In some embodiments, the present disclosure includes antibodies and antigen-binding fragments thereof that inhibit artemin-mediated cell signaling. In some embodiments, the present disclosure includes antibodies and antigen-binding fragments thereof that inhibit artemin-mediated cell signaling as measured using a bioassay in a cell line expressing human GFRα3 and human RET, e.g., as set forth in Example 4 or a substantially similar assay.

Epitope Mapping and Related Technologies

In some embodiments, the epitope on ARTN to which the antibodies of the present disclosure bind may consist of a single contiguous sequence of 3 or more (e.g., 3, 4, 5, 6, 7, 8, 9, 10, 11, 12, 13, 14, 15, 16, 17, 18, 19, 20 or more) amino acids of a ARTN protein. Alternatively, the epitope may consist of a plurality of non-contiguous amino acids (or amino acid sequences) of ARTN. In some embodiments, the antibodies of the disclosure may interact with amino acids contained within an ARTN monomer, or may interact with amino acids on two different chains of an ARTN dimer. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antibody "interacts with one or more amino acids" within a polypeptide or protein. Exemplary techniques that can be used to determine an epitope or binding domain of a particular antibody include, e.g., routine crossblocking assay such as that described in Antibodies, Harlow and Lane (Cold Spring Harbor Press, Cold Spring Harbor, N.Y.), point mutagenesis (e.g., alanine scanning mutagenesis, arginine scanning mutagenesis, etc.), peptide blots analysis (Reineke, 2004, *Methods Mol Biol* 248:443-463), protease protection, and peptide cleavage analysis. In addition, methods such as epitope excision, epitope extraction and chemical modification of antigens can be employed (Tomer, 2000, *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystal structure analysis can also be used to identify the amino acids within a polypeptide with which an antibody interacts.

In some embodiments, the present disclosure provides anti-artemin antibodies that bind to the same epitope as any of the specific exemplary antibodies described herein (e.g., antibodies comprising any of the amino acid sequences set forth in Table 1 or Table 9 below).

In some embodiments, the present disclosure provides anti-artemin antibodies that compete for binding to ARTN with any of the specific exemplary anti-artemin antibodies described herein.

One skilled in the art can determine whether a particular antibody thereof binds to the same epitope as, or competes for binding with, a reference antibody of the present disclosure by using routine methods known in the art. For example, to determine if a test antibody binds to the same epitope on ARTN as a reference antibody of the present disclosure, the reference antibody is first allowed to bind to an ARTN protein. Next, the ability of a test antibody to bind to the ARTN protein is assessed. If the test antibody is able to bind to ARTN following saturation binding with the reference antibody, it can be concluded that the test antibody binds to a different epitope of ARTN than the reference antibody. On the other hand, if the test antibody is not able to bind to ARTN following saturation binding with the reference antibody, then the test antibody may bind to the same epitope of ARTN as the epitope bound by the reference antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 2-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if a test antibody or antigen-binding fragment thereof competes for binding with a reference antibody, the above-described binding methodology is performed in two orientations: In a first orientation, the reference antibody is allowed to bind to an ARTN protein under saturating conditions followed by assessment of binding of the test antibody to the ARTN protein. In a second orientation, the test antibody is allowed to bind to an ARTN protein under saturating conditions followed by assessment of binding of the reference antibody to the ARTN protein. If, in both orientations, only the first (saturating) antibody is capable of binding to ARTN, then it is concluded that the test antibody and the reference antibody compete for binding to ARTN. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Antibodies

Antibodies as disclosed herein can be prepared by any antibody generating technology known in the art. In certain embodiments, one or more of the individual components (e.g., heavy and light chains) of the antibodies are derived from chimeric, humanized or fully human antibodies. Methods for making such antibodies are well known in the art. For example, one or more of the heavy and/or light chains of the antibodies of the present disclosure can be prepared using VELOCIMMUNE™ technology. Using VELOCIMMUNE™ technology (or any other human antibody generating technology), high affinity chimeric antibodies to a particular antigen (e.g., ARTN) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the antibodies.

In some embodiments, antibodies can be generated by administering to a mouse an immunogen (e.g., a peptide as shown in SEQ ID NO:82, optionally conjugated to a carrier), optionally in combination with an adjuvant. Following immunization, splenocytes are harvested and fused with mouse myeloma cells to preserve their viability and form hybridoma cell lines. The hybridoma cell lines are screened and selected to identify cell lines that produce artemin-specific antibodies. Alternatively, DNA encoding antigen-specific chimeric antibodies or the variable domains of the light and heavy chains can be isolated directly from antigen-positive B cells without fusion to myeloma cells, as described in U.S. 2007/0280945 or WO2016077666, each of which is incorporated by reference in its entirety.

In some embodiments, genetically engineered animals may be used to make human antibodies. Non-limiting exemplary genetically modified mice, and methods of generating antibodies from genetically modified mice, are described in U.S. Pat. Nos. 8,697,940, 10,130,081, 10,561,124, and 10,640,800, the entire contents of each of which are incorporated by reference herein. As used herein, "fully human" refers to an antigen-binding molecule, e.g., an antibody, or antigen-binding fragment or immunoglobulin domain thereof, comprising an amino acid sequence encoded by a DNA derived from a human sequence over the entire length of each polypeptide of the antigen-binding molecule, antibody, antigen-binding fragment, or immunoglobulin domain thereof. In some instances, the fully human sequence is derived from a protein endogenous to a human. In other instances, the fully human protein or protein sequence comprises a chimeric sequence wherein each component sequence is derived from human sequence. While not being bound by any one theory, chimeric proteins or chimeric sequences are generally designed to minimize the creation of immunogenic epitopes in the junctions of component sequences, e.g., compared to any wild-type human immunoglobulin regions or domains.

Bioequivalents

The present disclosure encompasses antibodies having amino acid sequences that vary from those of the described antibodies but that retain the ability to bind ARTN. Such variant molecules comprise one or more additions, deletions, or substitutions of amino acids when compared to a parent sequence, but exhibit biological activity that is essentially equivalent to that of the described antibodies. Likewise, the nucleic acid sequences encoding the antibodies of the present disclosure encompass sequences that comprise one or more additions, deletions, or substitutions of nucleotides when compared to the disclosed sequence, but that encode an antibody that is essentially bioequivalent to the antibodies disclosed herein.

The present disclosure includes antibodies that are bioequivalent to any of the exemplary antibodies set forth herein. Two antibodies are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antibodies are bioequivalent if there are no clinically meaningful differences in their safety, purity, and potency.

In one embodiment, two antibodies are bioequivalent if a patient can be switched one or more times between the first antibody (e.g., reference product) and the second antibody (e.g., biological product) without an expected increase in the risk of adverse effects, including a clinically significant change in immunogenicity, or diminished effectiveness, as compared to continued therapy without such switching.

In one embodiment, two antibodies are bioequivalent if they both act by a common mechanism or mechanisms of action for the condition or conditions of use, to the extent that such mechanisms are known.

Bioequivalence may be demonstrated by in vivo and in vitro methods. Non-limiting examples of bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the exemplary antibodies set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other embodiments, bioequivalent antibodies may include the exemplary antibodies set forth herein comprising amino acid changes which modify the glycosylation characteristics of the antibodies, e.g., mutations which eliminate or remove glycosylation.

Pharmaceutical Compositions

In another aspect, the present disclosure provides pharmaceutical compositions comprising the anti-artemin antibodies and antigen-binding fragments disclosed herein. The pharmaceutical compositions are formulated with one or more pharmaceutically acceptable vehicle, carriers, and/or excipients. Various pharmaceutically acceptable carriers and excipients are well-known in the art. See, e.g., Remington's Pharmaceutical Sciences, Mack Publishing Company, Easton, Pa. In some embodiments, the carrier is suitable for intravenous, intramuscular, oral, intraperitoneal, intrathecal, transdermal, topical, or subcutaneous administration.

In some embodiments, the pharmaceutical composition comprises an injectable preparation, such as a dosage form for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

The dose of antibody administered to a patient according to the present disclosure may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions as disclosed herein may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. In some embodiments, a pharmaceutical composition as disclosed herein is administered intravenously. In some embodiments, a pharmaceutical composition as disclosed herein is administered subcutaneously.

In some embodiments, an antibody or a pharmaceutical composition comprising an antibody as disclosed herein is contained within a container. Thus, in another aspect, containers comprising an antibody or pharmaceutical composition as disclosed herein are provided. For example, in some embodiments, an antibody or pharmaceutical composition is contained within a container selected from the group consisting of a glass vial, a syringe, a pen delivery device, and an autoinjector.

In some embodiments, an antibody or pharmaceutical composition of the present disclosure is delivered, e.g., subcutaneously or intravenously, with a standard needle and syringe. In some embodiments, the syringe is a pre-filled syringe. In some embodiments, a pen delivery device or autoinjector is used to deliver an antibody or pharmaceutical composition of the present disclosure (e.g., for subcutaneous delivery). A pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Examples of suitable pen and autoinjector delivery devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™ OPTIPEN STARLET™, and OPTICLIK™ (sanofi-aventis, Frankfurt, Germany). Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUM IRA™ Pen (Abbott Labs, Abbott Park Ill.).

In some embodiments, the antibody or pharmaceutical composition is delivered using a controlled release system. In one embodiment, a pump may be used (see Langer, supra; Sefton, 1987, *CRC Crit. Ref. Biomed. Eng.* 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

In some embodiments, pharmaceutical compositions for use as described herein are prepared into dosage forms in a unit dose suited to fit a dose of the active ingredients. Such dosage forms in a unit dose include, for example, tablets, pills, capsules, injections (ampoules), suppositories, etc. In some embodiments, the amount of the antigen-binding molecule contained in the dosage form is about 5 to about 500 mg, e.g., from about 5 to about 100 mg or from about 10 to about 250 mg.

Therapeutic Uses

In another aspect, the present disclosure provides for methods of using the anti-artemin antibodies and antigen-binding fragments disclosed herein. In some embodiments, the anti-artemin antibodies and antigen-binding fragments disclosed herein are useful for the treatment, prevention and/or amelioration of any disease, disorder, or condition associated with artemin expression (e.g., overexpression) or activity. In some embodiments, the disease, disorder, or condition is pain, e.g., acute pain, chronic pain, neuropathic pain, inflammatory pain, neuralgia (e.g., trigeminal neuralgia, postherpetic neuralgia, or general neuralgia), visceral pain, osteoarthritis pain, gout, radicular pain, sciatica, back pain, head or neck pain, breakthrough pain, post-surgical pain, chemotherapy induced neuropathic pain, radiotherapy-induced neuropathic pain, radiation-associated pain, or cancer pain (e.g., pain associated with bone cancer or pancreatic cancer).

In some embodiments, anti-artemin antibodies and antigen-binding fragments disclosed herein are useful for the treatment, prevention and/or amelioration of headache or pain associated with headache (e.g., for migraine, cluster headache, chronic headache, or tension headache).

In some embodiments, the antibodies or antigen-binding fragments thereof disclosed herein may also be used to treat any of the following conditions: non-malignant acute, chronic, or fracture bone pain; pain associated with arthritis (e.g., osteoarthritis or rheumatoid arthritis); spinal stenosis; neuropathic low back pain; myofascial pain syndrome; fibromyalgia; temporomandibular joint pain; visceral pain; chronic headache pain; tension headache, including cluster headaches; migraine; diabetic neuropathy; HIV-associated neuropathy; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome (CRPS); phantom pain; intractable pain; musculoskeletal pain; joint pain; acute gout pain; pruritus; mechanical low back pain; neck pain; tendonitis; injury/exercise pain; abdominal pain; chest pain, including cardiac pain; pelvic pain; renal colic pain; acute obstetric pain, including labor pain; cesarean section pain; burn and trauma pain; endometriosis; herpes zoster pain; breakthrough pain; orofacial pain including sinusitis pain or dental pain; multiple sclerosis pain; leprosy pain; Guillain-Barre pain; and Burning Mouth Syndrome.

Dosage and Administration Regimens

In some embodiments, an amount of an anti-artemin antibody or antigen-binding fragment that is administered to a subject according to the methods disclosed herein is a therapeutically effective amount. As used herein, the phrase "therapeutically effective amount" means an amount that produces the desired effect for which it is administered.

In some embodiments, the antibody is administered to a subject as a weight-based dose. A "weight-based dose" (e.g., a dose in mg/kg) is a dose of the antibody that will change depending on the subject's weight.

In other embodiments, the antibody is administered as a fixed dose. A "fixed dose" (e.g., a dose in mg) means that one dose of the antibody is used for all subjects regardless of any specific subject-related factors, such as weight. In one particular embodiment, a fixed dose of an antibody is based on a predetermined weight or age.

Typically, a suitable dose of the antibody can be in the range of about 0.001 to about 200.0 milligram per kilogram body weight of the recipient, generally in the range of about 1 to 50 mg per kilogram body weight. For example, the antibody can be administered at about 0.1 mg/kg, about 0.2 mg/kg, about 0.5 mg/kg, about 1 mg/kg, about 1.5 mg/kg, about 2 mg/kg, about 3 mg/kg, about 5 mg/kg, about 10 mg/kg, about 15 mg/kg, about 20 mg/kg, about 25 mg/kg, about 30 mg/kg, about 40 mg/kg, or about 50 mg/kg per single dose. Values and ranges intermediate to the recited values are also intended to be part of this disclosure.

In some embodiments, the antibody is administered as a fixed dose of between about 5 mg to about 2500 mg. In some embodiments, the antibody is administered as a fixed dose of about 5 mg, about 10 mg, about 15 mg, about 20 mg, about 25 mg, about 30 mg, about 50 mg, about 75 mg, about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, or about 2500 mg. Values and ranges intermediate to the recited values are also intended to be part of this disclosure.

In some embodiments, the antibody is administered to a subject at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved.

In some embodiments, multiple doses of an antibody as disclosed herein are administered to a subject over a defined time course. In some embodiments, the methods of the present disclosure comprise sequentially administering to a subject multiple doses of the antibody. As used herein, "sequentially administering" means that each dose of the antibody is administered to the subject at a different point in time, e.g., on different days separated by a predetermined interval (e.g., hours, days, weeks or months). In some embodiments, the methods of the disclosure comprise sequentially administering to the patient a single initial dose of the antibody, followed by one or more secondary doses of the antibody, and optionally followed by one or more tertiary doses of the antibody.

The terms "initial dose," "secondary dose(s)," and "tertiary dose(s)" refer to the temporal sequence of administration of the antibody. Thus, the "initial dose" is the dose which is administered at the beginning of the treatment regimen (also referred to as the "loading dose"); the "secondary doses" are the doses which are administered after the initial dose; and the "tertiary doses" are the doses which are administered after the secondary doses. In some embodiments, the initial, secondary, and tertiary doses may all contain the same amount of the antibody, but may differ from one another in terms of frequency of administration. In some embodiments, the amount of the antibody contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). In some embodiments, the initial dose and the one or more secondary doses each contain the same amount of the antibody. In other embodiments, the initial dose comprises a first amount of the antibody, and the one or more secondary doses each comprise a second amount of the antibody. For example, the first amount of the antibody can be 1.5×, 2×, 2.5×, 3×, 3.5×, 4× or 5× or more than the second amount of the antibody.

In some embodiments, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of the antibody that is administered to a patient prior to the administration of the very next dose in the sequence with no intervening doses.

The methods of the disclosure may comprise administering to a patient any number of secondary and/or tertiary doses of an antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In some embodiments involving multiple secondary doses, each secondary dose is administered at the same frequency as the other secondary doses. For example, each secondary dose may be administered to the patient 1, 2, 3, or 4 weeks after the immediately preceding dose. Similarly, in some embodiments involving multiple tertiary doses, each tertiary dose is administered at the same frequency as the other tertiary doses. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Combination Therapies

In some embodiments, an antibody or antigen-binding fragment of the disclosure can be used in combination with one more other therapeutic agents. In some embodiments, the additional therapeutic agent(s) is an antibody, small molecule, inhibitory nucleic acid (e.g., RNAi), antibody drug conjugate, bispecific antibody, or a combination thereof.

In some embodiments, an anti-artemin antibody of the disclosure can be administered in combination with another artemin inhibitor, an inhibitor of GFRα3 (e.g., an antibody disclosed in WO 2014/031712, incorporated by reference herein), an inhibitor of another GDNF family ligand or receptor, e.g. an inhibitor of GDNF, neurturin (NRTN), persephin (PSPN), GFRα1, GFRα2, or GFRα4, or a RET inhibitor.

In some embodiments, the anti-artemin antibody is administered in combination with an additional therapeutic agent that reduces, relieves, or ameliorates pain. Exemplary additional therapeutic agents include, but are not limited to: a COX-2 inhibitor; a local anesthetic; an NMDA modulator; a cannabinoid receptor agonist; a P2X family modulator; a VR1 antagonist; a substance P antagonist; an inhibitor of a voltage-gated sodium channel (Nav), for example, a Nav1.7 antagonist, Nav1.8 antagonist, or Nav1.9 antagonist (e.g., an antibody, small molecule inhibitor, or inhibitory nucleic acid against Nav1.7, Nav1.8, or Nav1.9); a calcium channel inhibitor; a potassium channel inhibitor; a cytokine inhibitor or cytokine receptor antagonist (e.g., an interleukin-1 (IL-1) inhibitor (such as rilonacept ("IL-1 trap"; Regeneron) or an interleukin-1 receptor (IL-1R) inhibitor, an IL-18 inhibitor, an IL-6 or IL-6R inhibitor, an IL-17 inhibitor, a tumor necrosis factor (TNF) or TNF receptor inhibitor (e.g., adalimumab), or an inhibitor of TWEAK (TNF-related WEAK inducer of apoptosis)); a growth factor inhibitor (e.g., nerve growth factor (NGF) inhibitor such as a small molecule NGF antagonist or an anti-NGF antibody); a neurotrophic factor inhibitor (e.g., an inhibitor of BDNF, TrkA, TrkB or p75, or another inhibitor of a GDNF family ligand or receptor); an antiepileptic/anti-convulsant drug (e.g., gabapentin, pregabalin); an opioid; morphine; low dose colchicine; aspirin or another NSAID; steroids (e.g., prednisone, methotrexate, etc.); low dose cyclosporine A; a selective serotonin reuptake inhibitor (SSRI); a serotonin norepinephrine reuptake inhibitor (SNRI); a tricyclic; an inhibitor of an acid sensing ion channel (e.g. ASIC1 or ASIC3); uric acid synthesis inhibitors (e.g., allopurinol); uric acid excretion promoters (e.g., probenecid, sulfinpyrazone, benzbromarone, etc.); and/or corticosteroids.

The additional therapeutically active component(s) may be administered just prior to, concurrent with, or shortly after the administration of an antibody of the present disclosure. For the purposes of the present disclosure, such administration regimens are considered the administration of an antibody "in combination with" an additional therapeutically active component.

The present disclosure includes pharmaceutical compositions in which an antibody of the present disclosure is co-formulated with one or more of the additional therapeutically active component(s) as described elsewhere herein.

EXAMPLES

The following examples are put forth so as to provide those of ordinary skill in the art with a complete disclosure and description of how to make and use the methods and compositions of the disclosure, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Human Antibodies to Human Artemin

Antibodies against human artemin were obtained by immunizing a VELOCIMMUNE® mouse (i.e., an engineered mouse comprising DNA encoding human Immunoglobulin heavy and kappa chain variable regions) with a human artemin antigen (hARTN(A108-G220) with a C-terminal mmH tag; SEQ ID NO:82), followed by a booster with the same immunogen.

Following immunization, antibodies were isolated directly from antigen-positive mouse B cells, e.g., as described in U.S. Pat. No. 7,582,298, incorporated by reference herein. Using this method, fully human anti-hARTN antibodies (i.e., antibodies possessing human variable domains and human constant domains) were obtained. Anti-ARTN antibodies generated using this method were designated H4H33331P, H4H33335P, H4H33336P, and H4H33349P. Certain biological properties of the exemplary anti-ARTN antibodies generated in accordance with the methods of this Example are described in detail in the Examples set forth below.

TABLE 1

Amino Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | HC | LCVR | LCDR1 | LCDR2 | LCDR3 | LC |
| H4H33331P | 2 | 4 | 6 | 8 | 18 | 10 | 12 | 14 | 16 | 20 |
| H4H33335P | 22 | 24 | 26 | 28 | 38 | 30 | 32 | 34 | 36 | 40 |
| H4H33336P | 42 | 44 | 46 | 48 | 58 | 50 | 52 | 54 | 56 | 60 |
| H4H33349P | 62 | 64 | 66 | 68 | 78 | 70 | 72 | 74 | 76 | 80 |

TABLE 2

Nucleic Acid Sequence Identifiers

| Antibody Designation | SEQ ID NOs: | | | | | | | | | |
|---|---|---|---|---|---|---|---|---|---|---|
| | HCVR | HCDR1 | HCDR2 | HCDR3 | HC | LCVR | LCDR1 | LCDR2 | LCDR3 | LC |
| H4H33331P | 1 | 3 | 5 | 7 | 17 | 9 | 11 | 13 | 15 | 19 |
| H4H33335P | 21 | 23 | 25 | 27 | 37 | 29 | 31 | 33 | 35 | 39 |
| H4H33336P | 41 | 43 | 45 | 47 | 57 | 49 | 51 | 53 | 55 | 59 |
| H4H33349P | 61 | 63 | 65 | 67 | 77 | 69 | 71 | 73 | 75 | 79 |

Example 2: Binding Characterization for Artemin Antibodies

Octet Binding of Artemin Monoclonal Antibodies

The binding of Artemin to each of Artemin monoclonal antibodies (mAbs) H4H33331 P, H4H33335P, H4H33336P, and H4H33349P was determined using a real time, label-free bio-layer interferometry (BLI) assay on the Octet HTX biosensor platform (Pall ForteBio Corp.). Tagged Artemin proteins were generated comprising the mature region of the human (hArtemin, Uniprot Q5T4W7-1, amino acids A108-G220), cynomolgus monkey (*Macaca fascicularis*, MfArtemin, XP_015292608.1, amino acids A108-G220; X110G, X111 P, X112G, X113S, X114R, X115P, X116R; X denotes human sequences at those specific positions) or mouse (mArtemin, Uniprot Q9Z0L2-1, amino acids A112-G224) protein fused to an epitope tag, myc-myc-6xHis, at the c-terminus). The sequence of tagged human Artemin, referred to as "hArtemin-MMH", is set forth at SEQ ID NO:82; the sequence of tagged monkey Artemin, referred to as "MfArtemin-MMH", is set forth at SEQ ID NO:83; and the sequence of tagged mouse Artemin, referred to as "mArtemin-MMH" or "msArtemin-MMH", is set forth at SEQ ID NO:84.

The entire experiment was performed at 25° C. in 10 mM HEPES, 150 mM NaCl, 3 mM EDTA, 0.02% NaN3 and 0.05% v/v Surfactant Tween-20, 1 mg/mL BSA, pH7.4 (HBS-EBT) buffer with the plate shaking at a speed of 1000 rpm. Different Artemin mAbs were first captured onto anti-human antibody (AHC) coated Octet biosensor tips (Fortebio Inc, #18-5064) by submerging the biosensor tips for 40 seconds in wells containing 2 pg/mL of Artemin mAb. The Artemin mAb-captured biosensor tips were later dipped in wells containing different concentrations (30-3.75 nM, 2-fold serial dilution) of tagged human, monkey, or mouse Artemin protein for 3 minutes and their dissociation in HBS-EBT buffer was monitored for 20 minutes. All the Artemin and Artemin mAb samples were prepared in HBS-EBT buffer. The real-time binding response was monitored during the entire course of the experiment and the binding response at the end of every step was recorded.

Figure 2:
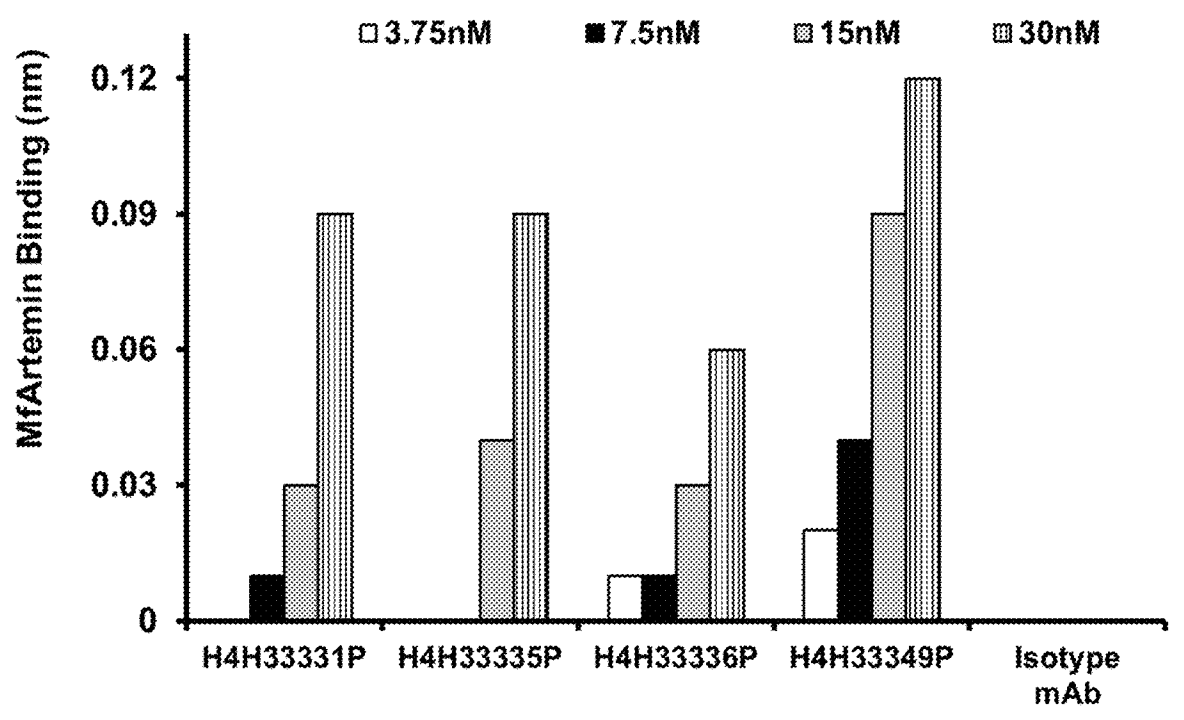
Figure 3:
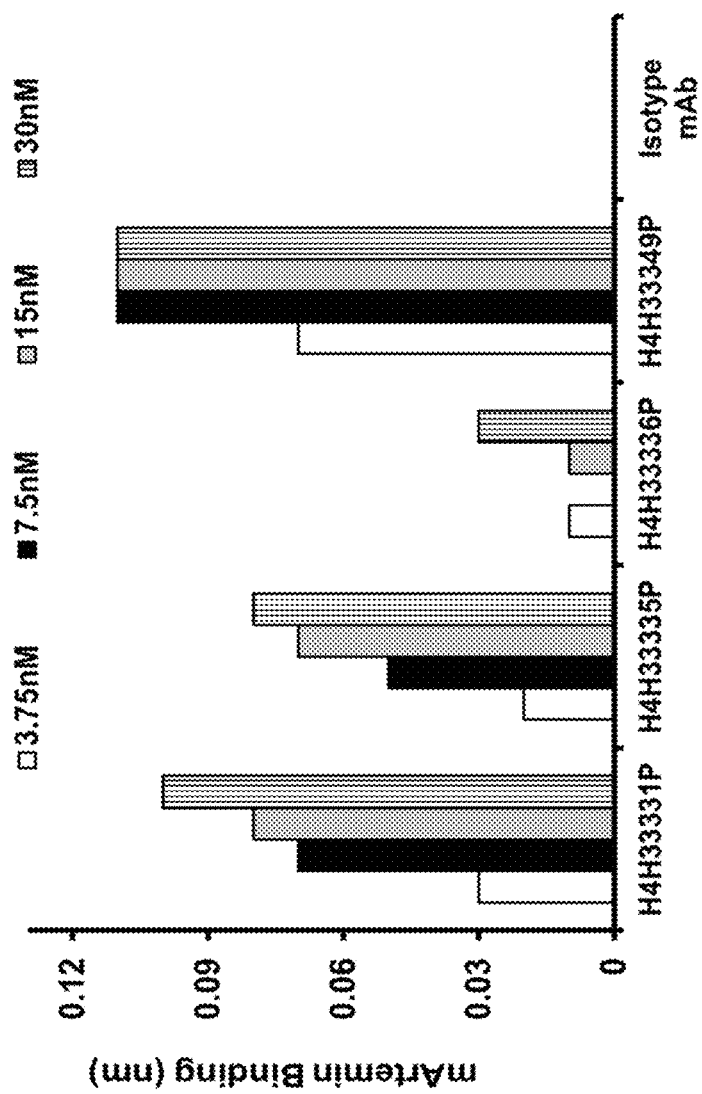
FIG. 3. Binding of different concentrations of mArtemin-MMH (mouse Artemin) to Artemin mAb-captured Octet biosensor surface.

The binding of various Artemin reagents to the different Artemin mAbs are reported in Table 3 and the concentration dependent binding data are also provided in FIGS. 1 to 3.

As shown in Table 3 and FIG. 1, all four Artemin mAbs bound to hArtemin-MMH at 25° C.

As shown in Table 3 and FIG. 2, all four Artemin mAbs bound to MfArtemin-MMH at 25° C.

As shown in Table 3 and FIG. 3, all four Artemin mAbs bound to mArtemin-MMH at 25° C.

v/v Surfactant Tween-20, pH 7.4 (HBS-ET) running buffer at 25° C. The Biacore CM4 sensor chip surface was first derivatized by amine coupling with anti-myc mAb to capture hArtemin-MMH, MfArtemin-MMH, or mArtemin-MMH. Different concentrations of Artemin mAbs (60-2.2 nM, 3-fold serial dilution) prepared in HBS-EP running buffer were injected over the Artemin-captured surfaces for 3 min at a flow rate of 50 μL/min and their dissociation in HBS-ET running buffer was monitored for 5 minutes. At the end of each cycle, the Artemin-captured surfaces were regenerated using a 6 sec injection of 20 mM phosphoric acid.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as: $K_D(M)=k_d/k_a$, and $t_{1/2}$ (min)=[ln2/(60*$k_d$)].

Binding kinetics parameters for Artemin binding to different Artemin mAbs of the invention at 25° C. are shown in Tables 4-6.

As shown in Table 4, all four Artemin mAbs bound to hArtemin-MMH at 25° C. with $K_D$ values ranging from 119 pM to 2.91 nM.

As shown in Table 5, three out of four Artemin mAbs (H4H33331P, H4H33335P, and H4H33349P) bound to MfArtemin-MMH at 25° C. with $K_D$ values ranging from 111 pM to 1.51 nM. Specific binding was also observed for the mAb H4H33335P, but binding kinetic parameters could not be determined under the current experimental conditions.

TABLE 3

Binding of Various Artemin Reagents to Different Artemin mAbs

| mAb Captured | Artemin Binding Tested | mAb Capture Level (nm) | Artemin Binding Response (nm) | | | |
|---|---|---|---|---|---|---|
| | | | 3.75 nM | 7.5 nM | 15 nM | 30 nM |
| H4H33331P | hArtemin-MMH | 0.34 ± 0.01 | 0.02 | 0.07 | 0.11 | 0.11 |
| | MfArtemin-MMH | 0.35 ± 0.01 | 0.00 | 0.01 | 0.03 | 0.09 |
| | mArtemin-MMH | 0.35 ± 0.01 | 0.03 | 0.07 | 0.08 | 0.10 |
| H4H33335P | hArtemin-MMH | 0.32 ± 0.01 | 0.02 | 0.07 | 0.11 | 0.11 |
| | MfArtemin-MMH | 0.33 ± 0.01 | 0.00 | 0.00 | 0.04 | 0.09 |
| | mArtemin-MMH | 0.33 ± 0.01 | 0.02 | 0.05 | 0.07 | 0.08 |
| H4H33336P | hArtemin-MMH | 0.37 ± 0.01 | 0.03 | 0.05 | 0.09 | 0.12 |
| | MfArtemin-MMH | 0.38 ± 0.01 | 0.01 | 0.01 | 0.03 | 0.06 |
| | mArtemin-MMH | 0.37 ± 0.01 | 0.01 | 0.00 | 0.01 | 0.03 |
| H4H33349P | hArtemin-MMH | 0.36 ± 0.01 | 0.07 | 0.11 | 0.11 | 0.11 |
| | MfArtemin-MMH | 0.38 ± 0.01 | 0.02 | 0.04 | 0.09 | 0.12 |
| | mArtemin-MMH | 0.36 ± 0.01 | 0.07 | 0.11 | 0.11 | 0.11 |
| Isotype mAb | hArtemin-MMH | 0.34 | NT$ | NT | NT | 0.00 |
| | MfArtemin-MMH | 0.35 | NT | NT | NT | 0.00 |
| | mArtemin-MMH | 0.35 | NT | NT | NT | 0.00 |

$indicates that the binding of Artemin to isotype mAb-captured surface was not tested at the indicated concentrations.

Biacore Binding Kinetics of Artemin Monoclonal Antibodies

The equilibrium dissociation constant ($K_D$) for Artemin binding to each of Artemin monoclonal antibodies (mAbs) H4H33331 P, H4H33335P, H4H33336P, and H4H33349P was determined using a real-time surface plasmon resonance Biacore T200 biosensor. All binding studies were performed in 10 mM HEPES, 150 mM NaCl, 3 mM EDTA, and 0.05%

As shown in Table 6, two out of four Artemin mAbs (H4H33331 P and H4H33349P) bound to mArtemin-MMH at 25° C. with $K_D$ values of 113 pM and 346 pM, respectively. Specific binding was also observed for the mAbs H4H33335P and H4H33336P, but binding kinetic parameters could not be determined under the current experimental conditions.

TABLE 4

Binding Kinetics Parameters of Different Artemin Monoclonal Antibodies Binding to hArtemin-MMH at 25° C.

| mAb Tested | hArtemin-MMH Capture Level (RU) | 60 nM Artemin mAb Bound (RU) | $k_a$ (1/Ms) | $k_d$ (1/s) | $K_D$ (M) | $t\frac{1}{2}$ (min) |
|---|---|---|---|---|---|---|
| H4H33331P | 3.5 ± 0.1 | 7 | 1.26E+05 | 3.66E−04 | 2.91E−09 | 32 |
| H4H33335P | 3.5 ± 0.1 | 4 | 8.53E+04 | 1.90E−04 | 2.22E−09 | 61 |
| H4H33336P | 3.6 ± 0.1 | 15 | 2.49E+05 | 3.75E−05 | 1.50E−10 | 308 |
| H4H33349P | 3.6 ± 0.1 | 18 | 4.97E+05 | 5.90E−05 | 1.19E−10 | 196 |
| Isotype Control mAb | 3.6 ± 0.1 | 0 | NB* | NB* | NB* | NB* |

*indicates that no binding (NB) was observed under the current experimental conditions.

TABLE 5

Binding Kinetics Parameters of Different Artemin Monoclonal Antibodies Binding to MfArtemin-MMH at 25° C.

| mAb Tested | MfArtemin-MMH Capture Level (RU) | 60 nM Artemin mAb Bound (RU) | $k_a$ (1/Ms) | $k_d$ (1/s) | $K_D$ (M) | $t\frac{1}{2}$ (min) |
|---|---|---|---|---|---|---|
| H4H33331P | 4.8 ± 0.1 | 5 | 1.31E+05 | 1.99E−04 | 1.51E−09 | 58 |
| H4H33335P | 4.8 ± 0.1 | 3 | NA# | NA# | NA# | NA# |
| H4H33336P | 4.6 ± 0.1 | 11 | 2.07E+05 | 2.30E−05 | 1.11E−10 | 502 |
| H4H33349P | 4.7 ± 0.1 | 14 | 4.57E+05 | 9.60E−05 | 2.10E−10 | 120 |
| Isotype Control mAb | 4.8 ± 0.1 | 0 | NB* | NB* | NB* | NB* |

*indicates that no binding (NB) was observed under the current experimental conditions.
indicates that specific binding was observed, but binding kinetic parameters could not be determined under the current experimental conditions and therefore not available (NA).

TABLE 6

Binding Kinetics Parameters of Different Artemin Monoclonal Antibodies Binding to mArtemin-MMH at 25° C.

| mAb Tested | mArtemin-MMH Capture Level (RU) | 60 nM Artemin mAb Bound (RU) | $k_a$ (1/Ms) | $k_d$ (1/s) | $K_D$ (M) | $t\frac{1}{2}$ (min) |
|---|---|---|---|---|---|---|
| H4H33331P | 2.6 ± 0.1 | 7 | 1.56E+05 | 5.40E−05 | 3.46E−10 | 214 |
| H4H33335P | 2.7 ± 0.1 | 3 | NA# | NA# | NA# | NA# |
| H4H33336P | 2.8 ± 0.1 | 3 | NA# | NA# | NA# | NA# |
| H4H33349P | 2.9 ± 0.1 | 20 | 5.21E+05 | 5.91E−05 | 1.13E−10 | 195 |
| Isotype Control mAb | 3.0 ± 0.1 | 0 | NB* | NB* | NB* | NB* |

*indicates that no binding (NB) was observed under the current experimental conditions.
indicates that specific binding was observed, but binding kinetic parameters could not be determined under the current experimental conditions and therefore not available (NA).

Example 3: Anti-ARTN Antibody Blocking of ARTN Binding to GFRα3

Multiple artemin blocking assays were developed using an ELISA-based format to determine the ability of anti-artemin (ARTN) antibodies to block monomeric human, monkey (*Macaca fascicularis*) and mouse ARTN proteins binding to human GFRα3 (glial cell line derived neurotrophic factor (GDNF) family receptor alpha 3).

The artemin proteins used in the experiments were hArtemin-MMH, MfArtemin-MMH, or mArtemin-MMH, disclosed in Example 2 above. The human GFRα3 used in the experiments was comprised of UniProtKB Accession No. O60609, amino acids D32-W382, with the Fc portion of the human IgG1 at the c-terminus, and is referred to as "hGFRα3.hFc" (SEQ ID NO:85).

Experiments were carried out using the following procedures. Plates were coated with hGFRα3.hFc at 2 µg/ml in PBS on a 96-well microtiter plate at 4° C. overnight for all three assays. After overnight coating, nonspecific binding sites were subsequently blocked using a 0.5% (w/v) BSA in PBS for one hour at room temperature. In other microtiter plates, a constant amount of either 75 pM hARTN.mmh, 400 pM mfARTN.mmh, or 150 pM msARTN.mmh were separately bound with anti-ARTN antibodies and an irrelevant IgG4 antibody control at a serial dilution series from 0.0017 nM to 100 nM in PBS+0.5% BSA. After a one-hour incubation, the mixture solutions were transferred to microtiter plates coated with hGFRα3.hFc. After one hour of incubation at RT, the wells were washed with PBST, and plate-bound ARTN was detected with an anti-penta-His antibody conjugated with horseradish peroxidase (HRP) (Qiagen). The plates were then developed using TMB substrate solution (BD Biosciences, #555214) according to manufacturer's recommendation and absorbance at 450 nm was measured on a Victor X5 plate reader.

Binding data were analyzed using a sigmoidal dose-response model within Prism™ software (GraphPad). The calculated IC50 value, defined as the concentration of antibody required to block 50% of ARTN.mmh binding to plate-coated hGFRα3.hFc, was used as an indicator of blocking potency. The lower limit of the assay (LLOA) for the IC50 of hARTN.mmh, mfARTN.mmh, and mARTN.mmh were 18.8 pM, 100 pM, and 37.5 pM respectively, based on the binding stoichiometry of two artemin to one antibody. If the calculated IC50 value was below the LLOA, less than LLOA was reported. Percent blocking at 100 nM antibody was calculated based on the background-corrected binding signal observed at the highest antibody concentration tested using the formula listed below and reported for all tested antibodies:

$$\% \text{Blocking} = 100 - 100 \times \left( \frac{[\text{Experimental Signal}_{(highest\ Ab\ conc)} - \text{Background Signal}_{(buffer)}]}{[\text{Maximum Signal}_{(ARTN.mmh\ alone)} - \text{Background Signal}_{(buffer)}]} \right)$$

Results

The ability of anti-ARTN antibodies to block human, monkey and mouse artemin binding to human GFRα3 was assessed using multiple blocking ELISA formats. In these assays 75 pM hARTN.mmh, 400 pM mfARTN.mmh or 150 pM msARTN.mmh were titrated with a wide range of concentrations of anti-ARTN antibodies and the binding of the three species of artemin to hGFRα3.hFc in the presence of antibodies were evaluated. The plate bound ARTN.mmh was detected with an HRP conjugated anti-penta-His antibody.

The four test antibodies potently blocked human, monkey, and mouse artemin binding to plate-bound human GFRα3, with IC50s below 1 nM and greater than 50% blocking at the highest concentration of antibody tested. The blocking IC50s and percent blocking at the highest tested concentrations of the anti-ARTN antibodies are summarized in Table 7. The irrelevant isotype control antibody showed no blocking activity.

TABLE 7

Potency of Antibodies Blocking Human, Monkey, and Mouse Artemin Binding to Human GFRα3

| Ab | Human ARTN | | Monkey ARTN | | Mouse ARTN | |
|---|---|---|---|---|---|---|
| | IC50 (M) | % Blocking with 100 nM Ab | IC50 (M) | % Blocking with 100 nM Ab | IC50 (M) | % Blocking with 100 nM Ab |
| H4H33331P | 3.80E−10 | 88 | 1.05E−10 | 90 | 1.36E−11* | 83 |
| H4H33335P | 5.05E−10 | 65 | 2.33E−10 | 71 | 8.76E−11 | 63 |
| H4H33336P | 1.61E−10 | 93 | 7.50E−11* | 86 | 4.10E−10 | 81 |
| H4H33349P | 1.28E−10 | 95 | 3.02E−11* | 88 | 7.65E−12* | 88 |
| hIgG4 isotype control | — | −3 | — | −28 | — | −31 |
| LLOA | 1.88E−11 | | 1.00E−10 | | 3.75E−11 | |

*below lower limit of assay

Example 4: Inhibition of Artemin-Mediated Cell Signaling by Artemin Monoclonal Antibodies To assess anti-Artemin antibody inhibition of Artemin-mediated cell signaling, a bioassay was established in HEK293 cells (human embryonic kidney, ATCC, #CRL-1573). HEK293 cells were transduced with a serum response element luciferase reporter (SRE-Luc, SA Biosciences) and engineered to stably express full-length human GFRα3 (amino acids M1 to W400 of Genbank Accession No. NP_001487.2) and full-length human RET isoform c (amino acids M1 to F1073 of Genbank Accession No. NP 065681.1 with two amino acid substitutions at G691S and R982C). An optimal cell clone was isolated and the resulting cell line was named HEK293/SRELuc/hRET/hGFRα3 cl.A3. Artemin proteins hArtemin-MMH, MfArtemin-MMH, or mArtemin-MMH are disclosed in Example 2 above.

For the bioassay, cells were seeded into 96-well plates at $2.5 \times 10^4$ cells/well using assay buffer (0.1% FBS in Opti-MEM medium) and cultured overnight (37° C., 5% $CO_2$). The following day, antibodies of the invention or an isotype control antibody were serially diluted (1:3) in assay media to final concentrations ranging from 100 nM to 1.7 pM (with an additional well for assay media alone without test molecule) and added to cells with a fixed concentration of Artemin (500 pM hArtemin, 3 nM of mfArtemin, or 1 nM of mArtemin) at 37° C. in 5% $CO_2$. To assess the extent of signaling activation, Artemin (h, mf, or m) was serially diluted (1:3) to final concentrations of 100 nM to 1.7 pM (with an additional well for assay media alone) and added to cells. After a 5-hour incubation, luciferase activity was evaluated by the addition of OneGlo™ luciferase assay system reagent (Promega E6130) and Relative Luminescence Units (RLU) were measured using an Envision multilabel plate reader (Perkin Elmer). Results were analyzed using a nonlinear regression (4-parameter logistic) in Prism® 8 to obtain EC50 and IC50 values. The percentage of inhibition was calculated using the following equation:

$$\% \text{ Inhibition} = 100 \times [(RLU_{Artemin} - RLU_{inhibition}) / (RLU_{Artemin} - RLU_{Baseline})]$$

In this equation "$RLU_{Artemin}$" refers to the RLU value from cells treated with constant Artemin without antibodies. "$RLU_{inhibition}$" refers to the RLU value measured at the maximum concentration of the antibody with constant Artemin. "$RLU_{Baseline}$" refers to RLU value of the cells measured in the absence of ligand or antibodies.

As shown in Table 8, anti-Artemin antibodies H4H33331 P, H4H33335P, H4H33336P, and H4H33349P were tested on HEK293/SRELuc/hRET/hGFRα3 cl.A3 cells with 500 pM hArtemin, 3 nM of mfArtemin, or 1 nM of mArtemin. Human, cyno monkey and mouse Artemin activated signaling through human GFRα3 and Ret receptors with EC50 values of 813 pM, 2.26 nM and 620 pM, respectively.

Acclimation and Baselining

In the week prior to intra-plantar injection, mice were handled and placed in the Hargreaves behavioral testing apparatus for at least two hours per day to acclimate them to the room and equipment. Animals were additionally acclimated for at least one hour before every testing session. Baseline nociceptive responses were taken at the end of the week.

Induction of Growth Factor-Induced Plantar Thermal Hyperalgesia

Baseline thermal hyperalgesia was evaluated using the Hargreaves Test (described below) before subcutaneous (s.c.) injections of artemin antibodies at 10 mg/kg were administered. PBS (one group) or recombinant mouse artemin from R&D Systems in 20 µl saline (five groups) was injected into the hindpaw three days later by placing mice into a clear plastic restrainer with their hind limbs exposed. The left hind limb was extended to inject 0.5 µg of artemin into the plantar surface of the paw. Thermal hyperalgesia was re-evaluated 4 days later. Using pilot results from artemin injections at a power level of 0.80 and alpha of 0.05, it was calculated that an n of 7-8 animals was needed to detect a return to baseline latencies to withdraw with antibody treatment. A sample size of 7 animals was chosen for the experiments because full blockade of the growth factor response was expected, and thus animal use could be minimized by selecting the smallest recommended sample size from the power analysis.

Thermal hyperalgesia: Animals were tested for heat sensitivity using the Hargreaves Test (Hargreaves et al, Pain, 1988, 32:77-88). Mice were placed on a 30° C.-heated glass (IITC model 390G with model 400 heated base) in individual chambers and acclimated before the reading session. The apparatus was set at a laser intensity of 15% and testing was performed using repeated measures (three measures per foot) on the plantar surface of the ipsilateral hind paw. Mean latency to withdraw was recorded, with a maximum beam

TABLE 8

Inhibition of Human, Cyno Monkey, and Mouse Artemin by Anti-Artemin Antibodies in HEK293/SRELuc/hRET/hGFRa3 cl.A3 Cells

| | 500 pM hArtemin | | 3 nM mfArtemin | | 1 nM mArtemin | |
|---|---|---|---|---|---|---|
| Antibody | IC50 | Max inhibition (%) | IC50 | Max inhibition (%) | IC50 | Max inhibition (%) |
| H4H33331P | 7.06E−11 | 100 | 3.06E−10 | 100 | 1.72E−10 | 100 |
| H4H33335P | 1.13E−10 | 100 | 3.86E−10 | 100 | 1.42E−09 | 95 |
| H4H33336P | 4.96E−11 | 100 | 2.33E−10 | 100 | 8.35E−10 | 100 |
| H4H33349P | 2.60E−11 | 100 | 1.45E−10 | 100 | 9.65E−11 | 100 |
| Isotype Control | No Inhibition | 9 | No Inhibition | 10 | No Inhibition | 1 |

Example 5: Inhibition of Intra-Plantar Artemin-Induced Thermal Hyperalgesia by Artemin Monoclonal Antibodies Animal Subjects 10-16 week old adult C57BL/6 male mice (Jackson Laboratories) were used for the experiment. Animals were housed in groups of up to five in a temperature-controlled environment on a 12-hour light/dark cycle with water and standard laboratory chow available ad libitum. All experimental procedures were approved by Regeneron's Animal Care and Use Committee and were performed by an experimenter blind to the group assignments of the animals.

exposure of 20 sec allowed to avoid tissue damage. Latency to withdraw was statistically analyzed using a one way independent groups ANOVA to compare treatment groups, with a set at 0.05. The significant main effect of treatment was probed using Tukey post hoc tests.

Results

Figure 4:
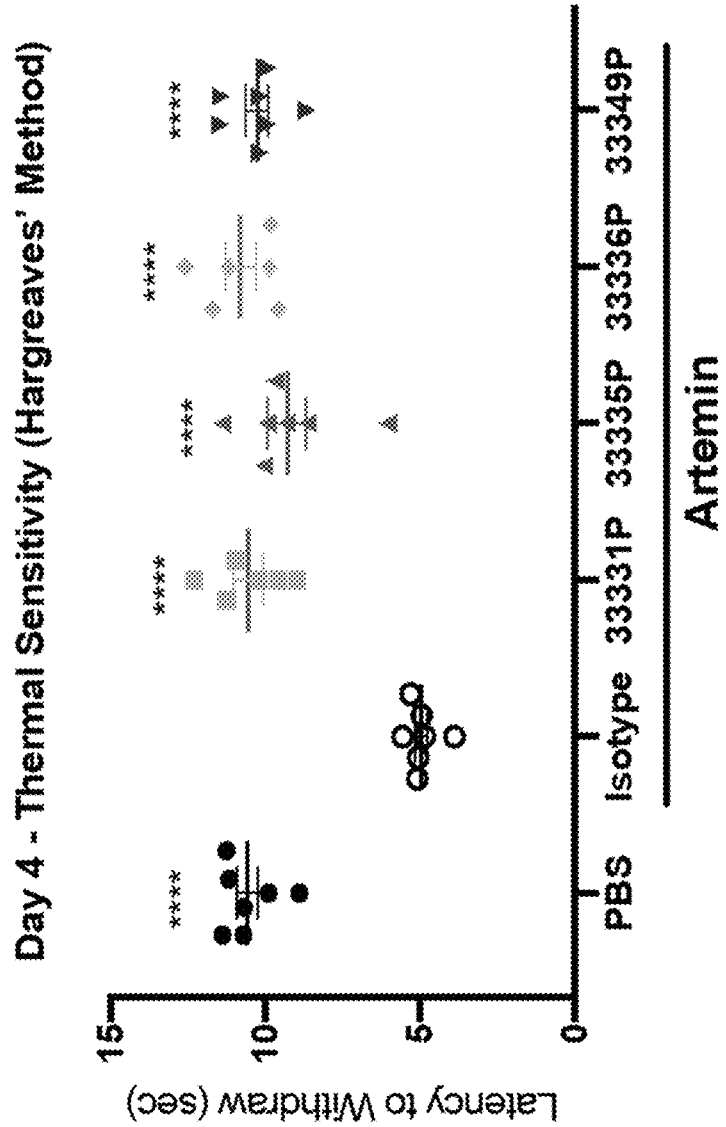
FIG. 4. Inhibition of artemin-induced plantar thermal hyperalgesia in animals administered an anti-artemin antibody (H4H33331 P, H4H33335P, H4H33336P, or H4H33349P) or isotype control antibody (negative control) at 10 mg/kg.

The four selected human anti-artemin antibodies (H4H33331P, H4H33335P, H4H33336P, and H4H33349P) were evaluated in the intraplantar growth factor-induced hyperalgesia model. As shown in FIG. 4, all four were shown to completely block thermal hyperalgesia induced by artemin in the Hargreaves Test at 10 mg/kg s.c. such that withdrawal latencies were similar to the group treated with intra-plantar PBS. The withdrawal thresholds of the animals receiving the anti-artemin antibodies were significantly different than those of the animals receiving the isotype control antibody, suggesting that all four artemin antibodies were effective at inhibiting artemin-induced hyperalgesia.

TABLE 9

Informal Sequence Listing

| SEQ ID NO | Sequence | Description |
|---|---|---|
| 1 | GAGGTGCAGCTGGTGGAGAGCGGCGGCGACCTGGTGCAGCCCGGCGGCAGCC TGAAGCTGAGCTGCGCCGCCAGCGGCTTCACCTTCAGCGGCAGCGCCATGCA CTGGGTGAGGCAGGCCAGCGGCAAGGGCCTGGAGTGGGTGGGCAGGATCAGG AACAAGGTGCACAGGTACGCCACCGAGTACGGCGCCAGCGTGAAGGGCAGGT TCACCATCAGCAGGGACGACAGCAAGAACACCGCCTACCTGCAGATGAACAG CCTGAAGATCGAGGACACCGCCGTGTACTACTGCGTGGTGGTGGTGCCCGGC AGCATCGAGGCCTTCGACATCTGGGGCCAGGGCACCATGGTGACCGTGAGCA GC | H4H33331P HCVR nucleotide sequence |
| 2 | EVQLVESGGDLVQPGGSLKLSCAASGFTFSGSAMHWVRQASGKGLEWVGRIR NKVHRYATEYGASVKGRFTISRDDSKNTAYLQMNSLKIEDTAVYYCVVVVPG SIEAFDIWGQGTMVTVSS | H4H33331P HCVR amino acid sequence |
| 3 | GGCTTCACCTTCAGCGGCAGCGCC | H4H33331P HCDR1 nucleotide sequence |
| 4 | GFTFSGSA | H4H33331P HCDR1 amino acid sequence |
| 5 | ATCAGGAACAAGGTGCACAGGTACGCCACC | H4H33331P HCDR2 nucleotide sequence |
| 6 | IRNKVHRYAT | H4H33331P HCDR2 amino acid sequence |
| 7 | GTGGTGGTGGTGCCCGGCAGCATCGAGGCCTTCGACATC | H4H33331P HCDR3 nucleotide sequence |
| 8 | VVVVPGSIEAFDI | H4H33331P HCDR3 amino acid sequence |
| 9 | GACATCCAGATGACCCAGAGCCCCAGCAGCCTGAGCGCCAGCGTGGGCGACA GGGTGACCATCACCTGCAGGGCCAGCCAGAGCATCAGCACCTACCTGAACTG GTACCAGCAGAAGCCCGGCAAGGCCCCCAACCTGCTGATCTACGCCGCCAGC ACCCTGGAGAGCGGCGTGCCCAGCAGGTTCAGCGGCAGCGGCAGCGGCACCG ACTTCACCCTGACCATCAGCAGCCTGCAGCCCGAGGACTTCGAGATCTACTA CTGCCAGCAGAGCTACAACATCCCCTGGACCTTCGGCCAGGGCACCAAGGTG GAGATCAAG | H4H33331P LCVR nucleotide sequence |
| 10 | DIQMTQSPSSLSASVGDRVTITCRASQSISTYLNWYQQKPGKAPNLLIYAAS TLESGVPSRFSGSGSGTDFTLTISSLQPEDFEIYYCQQSYNIPWTFGQGTKV EIK | H4H33331P LCVR amino acid sequence |
| 11 | CAGAGCATCAGCACCTAC | H4H33331P LCDR1 nucleotide sequence |
| 12 | QSISTY | H4H33331P LCDR1 amino acid sequence |
| 13 | GCCGCCAGC | H4H33331P LCDR2 nucleotide sequence |
| 14 | AAS | H4H33331P LCDR2 amino acid sequence |
| 15 | CAGCAGAGCTACAACATCCCCTGGACC | H4H33331P LCDR3 nucleotide sequence |
| 16 | QQSYNIPWT | H4H33331P LCDR3 amino acid sequence |
| 17 | GAGGTGCAGCTGGTGGAGAGCGGCGGCGACCTGGTGCAGCCCGGCGGCAGCC TGAAGCTGAGCTGCGCCGCCAGCGGCTTCACCTTCAGCGGCAGCGCCATGCA CTGGGTGAGGCAGGCCAGCGGCAAGGGCCTGGAGTGGGTGGGCAGGATCAGG AACAAGGTGCACAGGTACGCCACCGAGTACGGCGCCAGCGTGAAGGGCAGGT TCACCATCAGCAGGGACGACAGCAAGAACACCGCCTACCTGCAGATGAACAG CCTGAAGATCGAGGACACCGCCGTGTACTACTGCGTGGTGGTGGTGCCCGGC AGCATCGAGGCCTTCGACATCTGGGGCCAGGGCACCATGGTGACCGTGAGCA GCGCCAGCACCAAGGGCCCCAGCGTGTTCCCCCTGGCCCCCTGCAGCAGGAG CACCAGCGAGAGCACCGCCGCCCTGGGCTGCCTGGTGAAGGACTACTTCCCC GAGCCCGTGACCGTGAGCTGGAACAGCGGCGCCCTGACCAGCGGCGTGCACA CCTTCCCCGCCGTGCTGCAGAGCAGCGGCCTGTACAGCCTGAGCAGCGTGGT | H4H33331P heavy chain nucleotide sequence |

TABLE 9-continued

Informal Sequence Listing

| SEQ ID NO | Sequence | Description |
|---|---|---|
|  | GACCGTGCCCAGCAGCAGCCTGGGCACCAAGACCTACACCTGCAACGTGGAC CACAAGCCCAGCAACACCAAGGTGGACAAGAGGGTGGAGAGCAAGTACGGCC CCCCCTGCCCCCCCTGCCCCGCCCCCGAGTTCCTGGGCGGCCCCAGCGTGTT CCTGTTCCCCCCCAAGCCCAAGGACACCCTGATGATCAGCAGGACCCCCGAG GTGACCTGCGTGGTGGTGGACGTGAGCCAGGAGGACCCCGAGGTGCAGTTCA ACTGGTACGTGGACGGCGTGGAGGTGCACAACGCCAAGACCAAGCCCAGGGA GGAGCAGTTCAACAGCACCTACAGGGTGGTGAGCGTGCTGACCGTGCTGCAC CAGGACTGGCTGAACGGCAAGGAGTACAAGTGCAAGGTGAGCAACAAGGGCC TGCCCAGCAGCATCGAGAAGACCATCAGCAAGGCCAAGGGCCAGCCCAGGGA GCCCCAGGTGTACACCCTGCCCCCCAGCCAGGAGGAGATGACCAAGAACCAG GTGAGCCTGACCTGCCTGGTGAAGGGCTTCTACCCCAGCGACATCGCCGTGG AGTGGGAGAGCAACGGCCAGCCCGAGAACAACTACAAGACCACCCCCCCCGT GCTGGACAGCGACGGCAGCTTCTTCCTGTACAGCAGGCTGACCGTGGACAAG AGCAGGTGGCAGGAGGGCAACGTGTTCAGCTGCAGCGTGATGCACGAGGCCC TGCACAACCACTACACCCAGAAGAGCCTGAGCCTGAGCCTGGGCAAG |  |
| 18 | EVQLVESGGDLVQPGGSLKLSCAASGFTFSGSAMHWVRQASGKGLEWVGRIR NKVHRYATEYGASVKGRFTISRDDSKNTAYLQMNSLKIEDTAVYYCVVVPG SIEAFDIWGQGTMVIVSSASTKGPSVFPLAPCSRSTSESTAALGCLVKDYFP EPVTVSWNSGALTSGVHTFPAVLQSSGLYSLSSVVTVPSSSLGTKTYTCNVD HKPSNTKVDKRVESKYGPPCPPCPAPEFLGGPSVFLFPPKPKDTLMISRTPE VTCVVVDVSQEDPEVQFNWYVDGVEVHNAKTKPREEQFNSTYRVVSVLTVLH QDWLNGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSRLTVDK SRWQEGNVFSCSVMHEALHNHYTQKSLSLSLGK | H4H33331P heavy chain amino acid sequence |
| 19 | GACATCCAGATGACCCAGAGCCCCAGCAGCCTGAGCGCCAGCGTGGGCGACA GGGTGACCATCACCTGCAGGGCCAGCCAGAGCATCAGCACCTACCTGAACTG GTACCAGCAGAAGCCCGGCAAGGCCCCCAACCTGCTGATCTACGCCGCCAGC ACCCTGGAGAGCGGCGTGCCCAGCAGGTTCAGCGGCAGCGGCAGCGGCACCG ACTTCACCCTGACCATCAGCAGCCTGCAGCCCGAGGACTTCGAGATCTACTA CTGCCAGCAGAGCTACAACATCCCCTGGACCTTCGGCCAGGGCACCAAGGTG GAGATCAAGAGGACCGTGGCCGCCCCCAGCGTGTTCATCTTCCCCCCCAGCG ACGAGCAGCTGAAGAGCGGCACCGCCAGCGTGGTGTGCCTGCTGAACAACTT CTACCCCAGGGAGGCCAAGGTGCAGTGGAAGGTGGACAACGCCCTGCAGAGC GGCAACAGCCAGGAGAGCGTGACCGAGCAGGACAGCAAGGACAGCACCTACA GCCTGAGCAGCACCCTGACCCTGAGCAAGGCCGACTACGAGAAGCACAAGGT GTACGCCTGCGAGGTGACCCACCAGGGCCTGAGCAGCCCCGTGACCAAGAGC TTCAACAGGGGCGAGTGC | H4H33331P light chain nucleotide sequence |
| 20 | DIQMTQSPSSLSASVGDRVTITCRASQSISTYLNWYQQKPGKAPNLLIYAAS TLESGVPSRFSGSGSGTDFTLTISSLQPEDFEIYYCQQSYNIPWTFGQGTKV EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC | H4H33331P light chain amino acid sequence |
| 21 | GAGGTGCAGCTGGTGGAGAGCGGCGGCGGCCTGGTGCAGCCCGGCGGCAGCC TGAGGCTGAGCTGCGCCGCCAGCGGCTTCACCTTCAGCAGCTACGACATGCA CTGGGTGAGGCAGGCCACCGGCAAGGGCCTGGAGTGGGTGAGCACCATCGAC ACCGCCGGCGACACCTACTACCCCGGCAGCGTGAAGGGCAGGTTCACCATCA GCAGGGAGAACGCCAAGAACAGCCTGTACCTGCAGATGAACAGCCTGAGGGC CGGCGACACCGCCGTGTACTACTGCGCCAGGGACGGCGAGCTGGAGCTGCAG GGCTACTTCGACCTGTGGGGCAGGGGCACCCTGGTGACCGTGAGCAGC | H4H33335P HCVR nucleotide sequence |
| 22 | EVQLVESGGGLVQPGGSLRLSCAASGFTFSSYDMHWVRQATGKGLEWVSTID TAGDTYYPGSVKGRFTISRENAKNSLYLQMNSLRAGDTAVYYCARDGELELQ GYFDLWGRGTLVTVSS | H4H33335P HCVR amino acid sequence |
| 23 | GGCTTCACCTTCAGCAGCTACGAC | H4H33335P HCDR1 nucleotide sequence |
| 24 | GFTFSSYD | H4H33335P HCDR1 amino acid sequence |
| 25 | ATCGACACCGCCGGCGACACC | H4H33335P HCDR2 nucleotide sequence |
| 26 | IDTAGDT | H4H33335P HCDR2 amino acid sequence |
| 27 | GCCAGGGACGGCGAGCTGGAGCTGCAGGGCTACTTCGACCTG | H4H33335P HCDR3 nucleotide sequence |
| 28 | ARDGELELQGYFDL | H4H33335P HCDR3 amino acid sequence |

TABLE 9-continued

Informal Sequence Listing

| SEQ ID NO | Sequence | Description |
|---|---|---|
| 29 | GACATCCAGATGACCCAGAGCCCCAGCAGCCTGAGCGCCAGCGTGGGCGACA GGGTGACCATCACCTGCAGGGCCAGCCAGATCATCAGCATCTACCTGAACTG GTACCAGCAGAAGCCCGGCAAGGCCCCCAAGCTGCTGATCTACGCCGCCAGC AGCCTGCAGAGCGGCGTGCCCAGCAGGTTCAGCGGCAGCGGCAGCGGCACCG ACTTCACCCTGACCATCAGCAGCCTGCAGCCCGAGGACTTCGCCACCTACTA CTGCCAGCAGAGCTACACCACCCCCCTGACCTTCGGCGGCGGCACCAAGGTG GAGATCAAG | H4H33335P LCVR nucleotide sequence |
| 30 | DIQMTQSPSSLSASVGDRVTITCRASQIISIYLNWYQQKPGKAPKLLIYAAS SLQSGVPSRFSGSGSGTDFTLTISSLQPEDFATYYCQQSYTTPLTFGGGTKV EIK | H4H33335P LCVR amino acid sequence |
| 31 | CAGATCATCAGCATCTAC | H4H33335P LCDR1 nucleotide sequence |
| 32 | QIISIY | H4H33335P LCDR1 amino acid sequence |
| 33 | GCCGCCAGC | H4H33335P LCDR2 nucleotide sequence |
| 34 | AAS | H4H33335P LCDR2 amino acid sequence |
| 35 | CAGCAGAGCTACACCACCCCCCTGACC | H4H33335P LCDR3 nucleotide sequence |
| 36 | QQSYTTPLT | H4H33335P LCDR3 amino acid sequence |
| 37 | GAGGTGCAGCTGGTGGAGAGCGGCGGCGGCCTGGTGCAGCCCGGCGGCAGCC TGAGGCTGAGCTGCGCCGCCAGCGGCTTCACCTTCAGCAGCTACGACATGCA CTGGGTGAGGCAGGCCACCGGCAAGGGCCTGGAGTGGGTGAGCACCATCGAC ACCGCCGGCGACACCTACTACCCCGGCAGCGTGAAGGGCAGGTTCACCATCA GCAGGGAGAACGCCAAGAACAGCCTGTACCTGCAGATGAACAGCCTGAGGGC CGGCGACACCGCCGTGTACTACTGCGCCAGGGACGGCGAGCTGGAGCTGCAG GGCTACTTCGACCTGTGGGGCAGGGGCACCCTGGTGACCGTGAGCAGCGCCA GCACCAAGGGCCCCAGCGTGTTCCCCCTGGCCCCCTGCAGCAGGAGCACCAG CGAGAGCACCGCCGCCCTGGGCTGCCTGGTGAAGGACTACTTCCCCGAGCCC GTGACCGTGAGCTGGAACAGCGGCGCCCTGACCAGCGGCGTGCACACCTTCC CCGCCGTGCTGCAGAGCAGCGGCCTGTACAGCCTGAGCAGCGTGGTGACCGT GCCCAGCAGCAGCCTGGGCACCAAGACCTACACCTGCAACGTGGACCACAAG CCCAGCAACACCAAGGTGGACAAGAGGGTGGAGAGCAAGTACGGCCCCCCCT GCCCCCCCTGCCCCGCCCCCGAGTTCCTGGGCGGCCCCAGCGTGTTCCTGTT CCCCCCCAAGCCCAAGGACACCCTGATGATCAGCAGGACCCCCGAGGTGACC TGCGTGGTGGTGGACGTGAGCCAGGAGGACCCCGAGGTGCAGTTCAACTGGT ACGTGGACGGCGTGGAGGTGCACAACGCCAAGACCAAGCCCAGGGAGGAGCA GTTCAACAGCACCTACAGGGTGGTGAGCGTGCTGACCGTGCTGCACCAGGAC TGGCTGAACGGCAAGGAGTACAAGTGCAAGGTGAGCAACAAGGGCCTGCCCA GCAGCATCGAGAAGACCATCAGCAAGGCCAAGGGCCAGCCCAGGGAGCCCCA GGTGTACACCCTGCCCCCCAGCCAGGAGGAGATGACCAAGAACCAGGTGAGC CTGACCTGCCTGGTGAAGGGCTTCTACCCCAGCGACATCGCCGTGGAGTGGG AGAGCAACGGCCAGCCCGAGAACAACTACAAGACCACCCCCCCCGTGCTGGA CAGCGACGGCAGCTTCTTCCTGTACAGCAGGCTGACCGTGGACAAGAGCAGG TGGCAGGAGGGCAACGTGTTCAGCTGCAGCGTGATGCACGAGGCCCTGCACA ACCACTACACCCAGAAGAGCCTGAGCCTGAGCCTGGGCAAG | H4H33335P heavy chain nucleotide sequence |
| 38 | EVQLVESGGGLVQPGGSLRLSCAASGFTFSSYDMHWVRQATGKGLEWVSTID TAGDTYYPGSVKGRFTISRENAKNSLYLQMNSLRAGDTAVYYCARDGELELQ GYFDLWGRGTLVTVSSASTKGPSVFPLAPCSRSTSESTAALGCLVKDYFPEP VTVSWNSGALTSGVHTFPAVLQSSGLYSLSSVVTVPSSSLGTKTYTCNVDHK PSNTKVDKRVESKYGPPCPPCPAPEFLGGPSVFLFPPKPKDTLMISRTPEVT CVVVDVSQEDPEVQFNWYVDGVEVHNAKTKPREEQFNSTYRVVSVLTVLHQD WLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSR WQEGNVFSCSVMHEALHNHYTQKSLSLSLGK | H4H33335P heavy chain amino acid sequence |
| 39 | GACATCCAGATGACCCAGAGCCCCAGCAGCCTGAGCGCCAGCGTGGGCGACA GGGTGACCATCACCTGCAGGGCCAGCCAGATCATCAGCATCTACCTGAACTG GTACCAGCAGAAGCCCGGCAAGGCCCCCAAGCTGCTGATCTACGCCGCCAGC AGCCTGCAGAGCGGCGTGCCCAGCAGGTTCAGCGGCAGCGGCAGCGGCACCG ACTTCACCCTGACCATCAGCAGCCTGCAGCCCGAGGACTTCGCCACCTACTA CTGCCAGCAGAGCTACACCACCCCCCTGACCTTCGGCGGCGGCACCAAGGTG GAGATCAAGAGGACCGTGGCCGCCCCCAGCGTGTTCATCTTCCCCCCCAGCG | H4H33335P light chain nucleotide sequence |

TABLE 9-continued

Informal Sequence Listing

| SEQ ID NO | Sequence | Description |
|---|---|---|
| | ACGAGCAGCTGAAGAGCGGCACCGCCAGCGTGGTGTGCCTGCTGAACAACTT CTACCCCAGGGAGGCCAAGGTGCAGTGGAAGGTGGACAACGCCCTGCAGAGC GGCAACAGCCAGGAGAGCGTGACCGAGCAGGACAGCAAGGACAGCACCTACA GCCTGAGCAGCACCCTGACCCTGAGCAAGGCCGACTACGAGAAGCACAAGGT GTACGCCTGCGAGGTGACCCACCAGGGCCTGAGCAGCCCCGTGACCAAGAGC TTCAACAGGGGCGAGTGC | |
| 40 | DIQMTQSPSSLSASVGDRVTITCRASQIISIYLNWYQQKPGKAPKLLIYAAS SLQSGVPSRFSGSGSGTDFTLTISSLQPEDFATYYCQQSYTTPLTFGGGTKV EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC | H4H33335P light chain amino acid sequence |
| 41 | CAGGTGCAGCTGGTGGAGAGCGGCGGCGGCGTGGTGCAGCCCGGCAGGAGCC TGAGGCTGAGCTGCGTGGCCAGCGGCTTCATCCTGAGCCACTACGGCATGCA CTGGGTGAGGCAGGCCCCCGGCAAGGGCCTGGAGTGGGTGGCCGTGATCTGG TTCGACGGCACCAACAAGTACTACGCCGACAGCGTGAAGGGCAGGTTCACCG TGAGCAGGGACAACAGCAAGAACACCCTGTACATGCAGATGAACAGCCTGAG GGCCGAGGACACCGCCGTGTACTACTGCGCCAGGGACCCCCCCCCCGCCAGG AGGGGCAACTACAACGGCATGGACGTGTGGGGCCAGGGCACCACCGTGACCG TGAGCAGC | H4H33336P HCVR nucleotide sequence |
| 42 | QVQLVESGGGVVQPGRSLRLSCVASGFILSHYGMHWVRQAPGKGLEWVAVIW FDGTNKYYADSVKGRFTVSRDNSKNTLYMQMNSLRAEDTAVYYCARDPPPAR RGNYNGMDVWGQGTTVTVSS | H4H33336P HCVR amino acid sequence |
| 43 | GGCTTCATCCTGAGCCACTACGGC | H4H33336P HCDR1 nucleotide sequence |
| 44 | GFILSHYG | H4H33336P HCDR1 amino acid sequence |
| 45 | ATCTGGTTCGACGGCACCAACAAG | H4H33336P HCDR2 nucleotide sequence |
| 46 | IWFDGTNK | H4H33336P HCDR2 amino acid sequence |
| 47 | GCCAGGGACCCCCCCCCCGCCAGGAGGGGCAACTACAACGGCATGGACGTG | H4H33336P HCDR3 nucleotide sequence |
| 48 | ARDPPPARRGNYNGMDV | H4H33336P HCDR3 amino acid sequence |
| 49 | GACATCCAGATGACCCAGAGCCCCAGCAGCCTGAGCGCCAGCGTGGGCGACA GGGTGACCATCACCTGCAGGGCCAGCCAGGACATCAGGAACGACCTGGGCTG GTACCAGCAGAAGCCCGGCAAGGCCCCCAAGAGGCTGATCTTCGGCGCCAGC AGCCTGCAGAGCGGCGTGCCCCTGAGGTTCAGCGGCAGCGGCAGCGGCACCG AGTTCACCCTGACCATCAACAACCTGCAGCCCGAGGACTTCGCCACCTTCTA CTGCCTGCAGGACAACAGCTACCCCTGGACCTTCGGCCAGGGCACCAAGGTG GAGATCAAG | H4H33336P LCVR nucleotide sequence |
| 50 | DIQMTQSPSSLSASVGDRVTITCRASQDIRNDLGWYQQKPGKAPKRLIFGAS SLQSGVPLRFSGSGSGTEFTLTINNLQPEDFATFYCLQDNSYPWTFGQGTKV EIK | H4H33336P LCVR amino acid sequence |
| 51 | CAGGACATCAGGAACGAC | H4H33336P LCDR1 nucleotide sequence |
| 52 | QDIRND | H4H33336P LCDR1 amino acid sequence |
| 53 | GGCGCCAGC | H4H33336P LCDR2 nucleotide sequence |
| 54 | GAS | H4H33336P LCDR2 amino acid sequence |
| 55 | CTGCAGGACAACAGCTACCCCTGGACC | H4H33336P LCDR3 nucleotide sequence |
| 56 | LQDNSYPWT | H4H33336P LCDR3 amino acid sequence |

TABLE 9-continued

Informal Sequence Listing

| SEQ ID NO | Sequence | Description |
|---|---|---|
| 57 | CAGGTGCAGCTGGTGGAGAGCGGCGGCGGCGTGGTGCAGCCCGGCAGGAGCC TGAGGCTGAGCTGCGTGGCCAGCGGCTTCATCCTGAGCCACTACGGCATGCA CTGGGTGAGGCAGGCCCCCGGCAAGGGCCTGGAGTGGGTGGCCGTGATCTGG TTCGACGGCACCAACAAGTACTACGCCGACAGCGTGAAGGGCAGGTTCACCG TGAGCAGGGACAACAGCAAGAACACCCTGTACATGCAGATGAACAGCCTGAG GGCCGAGGACACCGCCGTGTACTACTGCGCCAGGGACCCCCCCCCCGCCAGG AGGGGCAACTACAACGGCATGGACGTGTGGGGCCAGGGCACCACCGTGACCG TGAGCAGCGCCAGCACCAAGGGCCCCAGCGTGTTCCCCCTGGCCCCCTGCAG CAGGAGCACCAGCGAGAGCACCGCCGCCCTGGGCTGCCTGGTGAAGGACTAC TTCCCCGAGCCCGTGACCGTGAGCTGGAACAGCGGCGCCCTGACCAGCGGCG TGCACACCTTCCCCGCCGTGCTGCAGAGCAGCGGCCTGTACAGCCTGAGCAG CGTGGTGACCGTGCCCAGCAGCAGCCTGGGCACCAAGACCTACACCTGCAAC GTGGACCACAAGCCCAGCAACACCAAGGTGGACAAGAGGGTGGAGAGCAAGT ACGGCCCCCCTGCCCCCCCTGCCCCGCCCCCGAGTTCCTGGGCGGCCCCAG CGTGTTCCTGTTCCCCCCCAAGCCCAAGGACACCCTGATGATCAGCAGGACC CCCGAGGTGACCTGCGTGGTGGTGGACGTGAGCCAGGAGGACCCCGAGGTGC AGTTCAACTGGTACGTGGACGGCGTGGAGGTGCACAACGCCAAGACCAAGCC CAGGGAGGAGCAGTTCAACAGCACCTACAGGGTGGTGAGCGTGCTGACCGTG CTGCACCAGGACTGGCTGAACGGCAAGGAGTACAAGTGCAAGGTGAGCAACA AGGGCCTGCCCAGCAGCATCGAGAAGACCATCAGCAAGGCCAAGGGCCAGCC CAGGGAGCCCCAGGTGTACACCCTGCCCCCCAGCCAGGAGGAGATGACCAAG AACCAGGTGAGCCTGACCTGCCTGGTGAAGGGCTTCTACCCCAGCGACATCG CCGTGGAGTGGGAGAGCAACGGCCAGCCCGAGAACAACTACAAGACCACCCC CCCCGTGCTGGACAGCGACGGCAGCTTCTTCCTGTACAGCAGGCTGACCGTG GACAAGAGCAGGTGGCAGGAGGGCAACGTGTTCAGCTGCAGCGTGATGCACG AGGCCCTGCACAACCACTACACCCAGAAGAGCCTGAGCCTGAGCCTGGGCAA G | H4H33336P heavy chain nucleotide sequence |
| 58 | QVQLVESGGGVVQPGRSLRLSCVASGFILSHYGMHWVRQAPGKGLEWVAVIW FDGTNKYYADSVKGRFTVSRDNSKNTLYMQMNSLRAEDTAVYYCARDPPPAR RGNYNGMDVWGQGTTVTVSSASTKGPSVFPLAPCSRSTSESTAALGCLVKDY FPEPVTVSWNSGALTSGVHTFPAVLQSSGLYSLSSVVTVPSSSLGTKTYTCN VDHKPSNTKVDKRVESKYGPPCPPCPAPEFLGGPSVFLFPPKPKDTLMISRT PEVTCVVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYSRLTV DKSRWQEGNVFSCSVMHEALHNHYTQKSLSLSLGK | H4H33336P heavy chain amino acid sequence |
| 59 | GACATCCAGATGACCCAGAGCCCCAGCAGCCTGAGCGCCAGCGTGGGCGACA GGGTGACCATCACCTGCAGGGCCAGCCAGGACATCAGGAACGACCTGGGCTG GTACCAGCAGAAGCCCGGCAAGGCCCCCAAGAGGCTGATCTTCGGCGCCAGC AGCCTGCAGAGCGGCGTGCCCCTGAGGTTCAGCGGCAGCGGCAGCGGCACCG AGTTCACCCTGACCATCAACAACCTGCAGCCCGAGGACTTCGCCACCTTCTA CTGCCTGCAGGACAACAGCTACCCCTGGACCTTCGGCCAGGGCACCAAGGTG GAGATCAAGAGGACCGTGGCCGCCCCCAGCGTGTTCATCTTCCCCCCCAGCG ACGAGCAGCTGAAGAGCGGCACCGCCAGCGTGGTGTGCCTGCTGAACAACTT CTACCCCAGGGAGGCCAAGGTGCAGTGGAAGGTGGACAACGCCCTGCAGAGC GGCAACAGCCAGGAGAGCGTGACCGAGCAGGACAGCAAGGACAGCACCTACA GCCTGAGCAGCACCCTGACCCTGAGCAAGGCCGACTACGAGAAGCACAAGGT GTACGCCTGCGAGGTGACCCACCAGGGCCTGAGCAGCCCCGTGACCAAGAGC TTCAACAGGGGCGAGTGC | H4H33336P light chain nucleotide sequence |
| 60 | DIQMTQSPSSLSASVGDRVTITCRASQDIRNDLGWYQQKPGKAPKRLIFGAS SLQSGVPLRFSGSGSGTEFTLTINNLQPEDFATFYCLQDNSYPWTFGQGTKV EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC | H4H33336P light chain amino acid sequence |
| 61 | CAGGTGCAGCTGGTGGAGAGCGGCGGCGGCGTGGTGCAGCCCGGCAGGAGCC TGAGGCTGAGCTGCGAGGCCAGCGGCTTCACCTTCAGCGACTACGACCTGCA CTGGGTGAGGCAGGCCCCCGGCAAGGGCCTGGAGTGGGTGGCCTTCATCAGC AACGACGGCAGCAACGAGTACTACCCCAAGAGCGTGAAGGGCAGGTTCAGCA TCAGCAGGGACAACAGCAAGAACACCCTGTACCTGCAGATGAACAGCCTGAG GGCCGAGGACACCGCCGTGTACCACTGCACCAAGGAGAGGGACTACTACTAC GACAGCAGCGGCAGCCTGGACTACTGGGGCCAGGGCACCCTGGTGACCGTGA GCAGC | H4H33349P HCVR nucleotide sequence |
| 62 | QVQLVESGGGVVQPGRSLRLSCEASGFTFSDYDLHWVRQAPGKGLEWVAFIS NDGSNEYYPKSVKGRFSISRDNSKNTLYLQMNSLRAEDTAVYHCTKERDYYY DSSGSLDYWGQGTLVTSS | H4H33349P HCVR amino acid sequence |
| 63 | GGCTTCACCTTCAGCGACTACGAC | H4H33349P HCDR1 nucleotide sequence |

TABLE 9-continued

Informal Sequence Listing

| SEQ ID NO | Sequence | Description |
|---|---|---|
| 64 | GFTFSDYD | H4H33349P HCDR1 amino acid sequence |
| 65 | ATCAGCAACGACGGCAGCAACGAG | H4H33349P HCDR2 nucleotide sequence |
| 66 | ISNDGSNE | H4H33349P HCDR2 amino acid sequence |
| 67 | ACCAAGGAGAGGGACTACTACTACGACAGCAGCGGCAGCCTGGACTAC | H4H33349P HCDR3 nucleotide sequence |
| 68 | TKERDYYYDSSGSLDY | H4H33349P HCDR3 amino acid sequence |
| 69 | GACATCCAGATGACCCAGAGCCCCAGCAGCCTGAGCGCCAGCGTGGGCGACAGGGTGACCATCACCTGCAGGGCCAGCCAGACCATCAACAACTACCTGAACTGGTACCAGCAGAAGCCCGGCAAGGCCCCCAAGCTGCTGATCTACACCACCAGCGGCCTGCAGAGCGGCGTGCCCAGCAGGTTCAGCGGCAGGGGCAGCGGCACCGACTTCACCCTGGCCATCAGCAGCCTGCAGCCCGAGGACTTCGCCACCTACTACTGCCAGCAGAGCTACCACAGCCCCTTCACCTTCGGCCCCGGCACCAAGGTGGACATCAAG | H4H33349P LCVR nucleotide sequence |
| 70 | DIQMTQSPSSLSASVGDRVTITCRASQTINNYLNWYQQKPGKAPKLLIYTTSGLQSGVPSRFSGRGSGTDFTLAISSLQPEDFATYYCQQSYHSPFTFGPGTKVDIK | H4H33349P LCVR amino acid sequence |
| 71 | CAGACCATCAACAACTAC | H4H33349P LCDR1 nucleotide sequence |
| 72 | QTINNY | H4H33349P LCDR1 amino acid sequence |
| 73 | ACCACCAGC | H4H33349P LCDR2 nucleotide sequence |
| 74 | TTS | H4H33349P LCDR2 amino acid sequence |
| 75 | CAGCAGAGCTACCACAGCCCCTTCACC | H4H33349P LCDR3 nucleotide sequence |
| 76 | QQSYHSPFT | H4H33349P LCDR3 amino acid sequence |
| 77 | CAGGTGCAGCTGGTGGAGAGCGGCGGCGGCGTGGTGCAGCCCGGCAGGAGCCTGAGGCTGAGCTGCGAGGCCAGCGGCTTCACCTTCAGCGACTACGACCTGCACTGGGTGAGGCAGGCCCCCGGCAAGGGCCTGGAGTGGGTGGCCTTCATCAGCAACGACGGCAGCAACGAGTACTACCCCAAGAGCGTGAAGGGCAGGTTCAGCATCAGCAGGGACAACAGCAAGAACACCCTGTACCTGCAGATGAACAGCCTGAGGGCCGAGGACACCGCCGTGTACCACTGCACCAAGGAGAGGGACTACTACTACGACAGCAGCGGCAGCCTGGACTACTGGGGCCAGGGCACCCTGGTGACCGTGAGCAGCGCCAGCACCAAGGGCCCCAGCGTGTTCCCCCTGGCCCCCTGCAGCAGGAGCACCAGCGAGAGCACCGCCGCCCTGGGCTGCCTGGTGAAGGACTACTTCCCCGAGCCCGTGACCGTGAGCTGGAACAGCGGCGCCCTGACCAGCGGCGTGCACACCTTCCCCGCCGTGCTGCAGAGCAGCGGCCTGTACAGCCTGAGCAGCGTGGTGACCGTGCCCAGCAGCAGCCTGGGCACCAAGACCTACACCTGCAACGTGGACCACAAGCCCAGCAACACCAAGGTGGACAAGAGGGTGGAGAGCAAGTACGGCCCCCCCTGCCCCCCCTGCCCCGCCCCCGAGTTCCTGGGCGGCCCCAGCGTGTTCCTGTTCCCCCCCAAGCCCAAGGACACCCTGATGATCAGCAGGACCCCCGAGGTGACCTGCGTGGTGGTGGACGTGAGCCAGGAGGACCCCGAGGTGCAGTTCAACTGGTACGTGGACGGCGTGGAGGTGCACAACGCCAAGACCAAGCCCAGGGAGGAGCAGTTCAACAGCACCTACAGGGTGGTGAGCGTGCTGACCGTGCTGCACCAGGACTGGCTGAACGGCAAGGAGTACAAGTGCAAGGTGAGCAACAAGGGCCTGCCCAGCAGCATCGAGAAGACCATCAGCAAGGCCAAGGGCCAGCCCAGGGAGCCCCAGGTGTACACCCTGCCCCCCAGCCAGGAGGAGATGACCAAGAACCAGGTGAGCCTGACCTGCCTGGTGAAGGGCTTCTACCCCAGCGACATCGCCGTGGAGTGGGAGAGCAACGGCCAGCCCGAGAACAACTACAAGACCACCCCCCCCGTGCTGGACAGCGACGGCAGCTTCTTCCTGTACAGCAGGCTGACCGTGGACAAGAGCAGGTGGCAGGAGGGCAACGTGTTCAGCTGCAGCGTGATGCACGAGGCCCTGCACAACCACTACACCCAGAAGAGCCTGAGCCTGAGCCTGGGCAAG | H4H33349P heavy chain nucleotide sequence |

TABLE 9-continued

Informal Sequence Listing

| SEQ ID NO | Sequence | Description |
|---|---|---|
| 78 | QVQLVESGGGVVQPGRSLRLSCEASGFTFSDYDLHWVRQAPGKGLEWVAFIS NDGSNEYYPKSVKGRFSISRDNSKNTLYLQMNSLRAEDTAVYHCTKERDYYY DSSGSLDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCNV DHKPSNTKVDKRVESKYGPPCPPCPAPEFLGGPSVFLFPPKPKDTLMISRTP EVTCVVVDVSQEDPEVQFNWYVDGVEVHNAKTKPREEQFNSTYRVVSVLTVL HQDWLNGKEYKCKVSNKGLPSSIEKTISKAKGQPREPQVYTLPPSQEEMTKN QVSLTCLVKGFYPSDIAVEWESNGQPENNYKTTPPVLDSDGSFFLYSRLTVD KSRWQEGNVFSCSVMHEALHNHYTQKSLSLSLGK | H4H33349P heavy chain amino acid sequence |
| 79 | GACATCCAGATGACCCAGAGCCCCAGCAGCCTGAGCGCCAGCGTGGGCGACA GGGTGACCATCACCTGCAGGGCCAGCCAGACCATCAACAACTACCTGAACTG GTACCAGCAGAAGCCCGGCAAGGCCCCCAAGCTGCTGATCTACACCACCAGC GGCCTGCAGAGCGGCGTGCCCAGCAGGTTCAGCGGCAGGGGCAGCGGCACCG ACTTCACCCTGGCCATCAGCAGCCTGCAGCCCGAGGACTTCGCCACCTACTA CTGCCAGCAGAGCTACCACAGCCCCTTCACCTTCGGCCCCGGCACCAAGGTG GACATCAAGAGGACCGTGGCCGCCCCCAGCGTGTTCATCTTCCCCCCCAGCG ACGAGCAGCTGAAGAGCGGCACCGCCAGCGTGGTGTGCCTGCTGAACAACTT CTACCCCAGGGAGGCCAAGGTGCAGTGGAAGGTGGACAACGCCCTGCAGAGC GGCAACAGCCAGGAGAGCGTGACCGAGCAGGACAGCAAGGACAGCACCTACA GCCTGAGCAGCACCCTGACCCTGAGCAAGGCCGACTACGAGAAGCACAAGGT GTACGCCTGCGAGGTGACCCACCAGGGCCTGAGCAGCCCCGTGACCAAGAGC TTCAACAGGGGCGAGTGC | H4H33349P light chain nucleotide sequence |
| 80 | DIQMTQSPSSLSASVGDRVTITCRASQTINNYLNWYQQKPGKAPKLLIYTTS GLQSGVPSRFSGRGSGTDFTLAISSLQPEDFATYYCQQSYHSPFTFGPGTKV DIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC | H4H33349P light chain amino acid sequence |
| 81 | MELGLGGLSTLSHCPWPRQQPALWPTLAALALLSSVAEASLGSAPRSPAPRE GPPPVLASPAGHLPGGRTARWCSGRARRPPPQPSRPAPPPPAPPSALPRGGR AARAGGPGSRARAAGARGCRLRSQLVPVRALGLGHRSDELVRFRFCSGSCRR ARSPHDLSLASLLGAGALRPPPGSRPVSQPCCRPTRYEAVSFMDVNSTWRTV DRLSATACGCLG | Human ARTN protein (UniProtKB Accession No. Q5T4W7.1) |
| 82 | AGGPGSRARAAGARGCRLRSQINPVRALGLGHRSDELVRERFCSGSCRRARS PHDLSLASLLGAGALRPPPGSRPVSQPCCRPTRYEAVSTMDVNSTVVRTVDR LSATACGCLG<u>EQKLISEEDLGGEQKLISEEDLHHHHHH</u> | hARTN (A108-G220).mmh (mmh tag is underlined) |
| 83 | AGGPGSRPRAAGARGCRLRSQLVPVRALGLGHRSDELVRFRFCSGSCRRARS PHDLSLASLLGAGALRPPPGSRPISQPCCRPTRYEAVSFMDVNSTWRTVDRL SATACGCLG<u>EQKLISEEDLGGEQKLISEEDLHHHHHH</u> | mfARTN (A108-G22).mmh (mmh tag is underlined) |
| 84 | AGTRSSRARTTDARGCRLRSQLVPVSALGLGHSSDELIRFRFCSGSCRRARS QHDLSLASLLGAGALRSPPGSRPISQPCCRPTRYEAVSFMDVNSTWRTVDHL SATACGCLG<u>EQKLISEEDLGGEQKLISEEDLHHHHHH</u> | mARTN (A112-G224).mmh (mmh tag is underlined) |
| 85 | DPLPTESRLMNSCLQARRKCQADPTCSAAYHHLDSCTSSISTPLPSEEPSVP ADCLEAAQQLRNSSLIGCMCHRRMKNQVACLDIYWTVHRARSLGNYELDVSP YEDTVTSKPWKMNLSKLNMLKPDSDLCLKFAMLCTLNDKCDRLRKAYGEACS GPHCQRHVCLRQLLTFFEKAAEPHAQGLLLCPCAPNDRGCGERRRNTIAPNC ALPPVAPNCLELRRLCFSDPLCRSRLVDFQTHCHPMDILGTCATEQSRCLRA YLGLIGTAMTPNFVSNVNTSVALSCTCRGSGNLQEECEMLEGFFSHNPCLTE AIAAKMRFHSQLFSQDWPHPTFAVMAHQNENPAVRPQPWDKTHTCPPCPAPE LLGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSL SLSPGK | hGFRa3.hFc |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. The disclosures of all patents and non-patent literature cited herein are expressly incorporated in their entirety by reference.

What is claimed is:

1. An isolated monoclonal antibody or an antigen-binding fragment thereof that specifically binds to human artemin, wherein the antibody or antigen-binding fragment thereof comprises:
(a) an HCDR1 comprising the amino acid sequence of SEQ ID NO:4, an HCDR2 comprising the amino acid sequence of SEQ ID NO:6, an HCDR3 comprising the amino acid sequence of SEQ ID NO:8, an LCDR1 comprising the amino acid sequence of SEQ ID NO:12, an LCDR2 comprising the amino acid sequence of SEQ ID NO:14, and an LCDR3 comprising the amino acid sequence of SEQ ID NO:16; or
(b) an HCDR1 comprising the amino acid sequence of SEQ ID NO:24, an HCDR2 comprising the amino acid sequence of SEQ ID NO:26, an HCDR3 comprising the amino acid sequence of SEQ ID NO:28, an LCDR1 comprising the amino acid sequence of SEQ ID NO:32, an LCDR2 comprising the amino acid sequence of SEQ ID NO:34, and an LCDR3 comprising the amino acid sequence of SEQ ID NO:36; or
(c) an HCDR1 comprising the amino acid sequence of SEQ ID NO:44, an HCDR2 comprising the amino acid sequence of SEQ ID NO:46, an HCDR3 comprising the amino acid sequence of SEQ ID NO:48, an LCDR1 comprising the amino acid sequence of SEQ ID NO:52, an LCDR2 comprising the amino acid sequence of SEQ ID NO:54, and an LCDR3 comprising the amino acid sequence of SEQ ID NO:56; or (d) an HCDR1 comprising the amino acid sequence of SEQ ID NO:64, an HCDR2 comprising the amino acid sequence of SEQ ID NO:66, an HCDR3 comprising the amino acid sequence of SEQ ID NO:68, an LCDR1 comprising the amino acid sequence of SEQ ID NO:72, an LCDR2 comprising the amino acid sequence of SEQ ID NO:74, and an LCDR3 comprising the amino acid sequence of SEQ ID NO:76.

2. The isolated monoclonal antibody or antigen-binding fragment thereof of claim 1, wherein the antibody or antigen-binding fragment thereof comprises:
an HCDR1 comprising the amino acid sequence of SEQ ID NO:64, an HCDR2 comprising the amino acid sequence of SEQ ID NO:66, an HCDR3 comprising the amino acid sequence of SEQ ID NO:68, an LCDR1 comprising the amino acid sequence of SEQ ID NO:72, an LCDR2 comprising the amino acid sequence of SEQ ID NO:74, and an LCDR3 comprising the amino acid sequence of SEQ ID NO:76.

3. The isolated monoclonal antibody or antigen-binding fragment thereof of claim 1, wherein the antibody or antigen-binding fragment thereof comprises a heavy chain variable region (HCVR) comprising an amino acid sequence that has at least 85% sequence identity to an amino acid sequence selected from the group consisting of SEQ ID NOs:2, 22, 42, and 62.

4. The isolated monoclonal antibody or antigen-binding fragment thereof of claim 1, wherein the antibody or antigen-binding fragment thereof comprises a light chain variable region (LCVR) comprising an amino acid sequence that has at least 85% sequence identity to an amino acid sequence selected from the group consisting of SEQ ID NOs:10, 30, 50, and 70.

5. The isolated monoclonal antibody or antigen-binding fragment thereof of claim 1, wherein the antibody or antigen-binding fragment thereof comprises
an HCVR comprising the amino acid sequence of SEQ ID NO:62 and an LCVR comprising the amino acid sequence of SEQ ID NO:70.

6. The isolated monoclonal antibody or antigen-binding fragment thereof of claim 1, wherein the antibody or antigen-binding fragment thereof comprises:
(a) a heavy chain comprising an amino acid sequence having at least 85% sequence identity to the amino acid sequence of SEQ ID NO:18 and a light chain comprising an amino acid sequence having at least 85% sequence identity to the amino acid sequence of SEQ ID NO:20; or
(b) a heavy chain comprising an amino acid sequence having at least 85% sequence identity to the amino acid sequence of SEQ ID NO:38 and a light chain comprising an amino acid sequence having at least 85% sequence identity to the amino acid sequence of SEQ ID NO:40; or
(c) a heavy chain comprising an amino acid sequence having at least 85% sequence identity to the amino acid sequence of SEQ ID NO:58 and a light chain comprising an amino acid sequence having at least 85% sequence identity to the amino acid sequence of SEQ ID NO:60; or
(d) a heavy chain comprising an amino acid sequence having at least 85% sequence identity to the amino acid sequence of SEQ ID NO:78 and a light chain comprising an amino acid sequence having at least 85% sequence identity to the amino acid sequence of SEQ ID NO:80.

7. The isolated monoclonal antibody or antigen-binding fragment thereof of claim 6, wherein the antibody or antigen-binding fragment thereof comprises
a heavy chain comprising the amino acid sequence of SEQ ID NO:78 and a light chain comprising the amino acid sequence of SEQ ID NO:80.

8. The isolated monoclonal antibody or antigen-binding fragment thereof of claim 1, wherein the antibody or antigen-binding fragment thereof is fully human.

9. A pharmaceutical composition comprising the monoclonal antibody or antigen-binding fragment thereof of claim 1 and a pharmaceutically acceptable carrier.

10. A nucleic acid molecule comprising a nucleotide sequence encoding the monoclonal antibody or antigen-binding fragment thereof of claim 1.

11. An expression vector comprising the nucleic acid molecule of claim 10.

12. A host cell comprising the expression vector of claim 11.

13. A method of producing an anti-human artemin antibody or antigen-binding fragment thereof, the method comprising introducing the expression vector of claim 11 into a host cell, growing the host cell under conditions permitting production of the antibody or antigen-binding fragment thereof, and recovering the antibody or antigen-binding fragment that is produced.

14. A method of inhibiting artemin-activated signaling in a cell, the method comprising contacting the cell with the monoclonal antibody or antigen-binding fragment thereof of claim 1, thereby inhibiting artemin-activated signaling in the cell.

15. The method of claim 14, wherein the cell is within a subject.

16. A method of treating a pain-related disease, disorder, or condition associated with increased artemin expression or activity, the method comprising administering the monoclonal antibody or antigen-binding fragment thereof of claim 1 to a subject in need thereof.

17. The method of claim 16, wherein the pain-related disease, disorder, or condition is acute pain, chronic pain, neuropathic pain, inflammatory pain, trigeminal neuralgia, postherpetic neuralgia, general neuralgia, visceral pain, osteoarthritis pain, gout, radicular pain, sciatica, back pain, head or neck pain, breakthrough pain, post-surgical pain, chemotherapy induced neuropathic pain, radiotherapy-induced neuropathic pain, radiation-associated pain, or cancer pain.

18. The method of claim 16, wherein the pain-related disease, disorder, or condition is migraine, cluster headache, chronic headache, or tension headache.

19. The isolated monoclonal antibody or antigen-binding fragment thereof of claim 1, wherein the antibody or antigen-binding fragment thereof comprises:
an HCDR1 comprising the amino acid sequence of SEQ ID NO:4, an HCDR2 comprising the amino acid sequence of SEQ ID NO:6, an HCDR3 comprising the amino acid sequence of SEQ ID NO:8, an LCDR1 comprising the amino acid sequence of SEQ ID NO:12, an LCDR2 comprising the amino acid sequence of SEQ ID NO:14, and an LCDR3 comprising the amino acid sequence of SEQ ID NO:16.

20. The isolated monoclonal antibody or antigen-binding fragment thereof of claim 1, wherein the antibody or antigen-binding fragment thereof comprises:
an HCDR1 comprising the amino acid sequence of SEQ ID NO:24, an HCDR2 comprising the amino acid sequence of SEQ ID NO:26, an HCDR3 comprising the amino acid sequence of SEQ ID NO:28, an LCDR1 comprising the amino acid sequence of SEQ ID NO:32, an LCDR2 comprising the amino acid sequence of SEQ ID NO:34, and an LCDR3 comprising the amino acid sequence of SEQ ID NO:36.

21. The isolated monoclonal antibody or antigen-binding fragment thereof of claim 1, wherein the antibody or antigen-binding fragment thereof comprises:
an HCDR1 comprising the amino acid sequence of SEQ ID NO:44, an HCDR2 comprising the amino acid sequence of SEQ ID NO:46, an HCDR3 comprising the amino acid sequence of SEQ ID NO:48, an LCDR1 comprising the amino acid sequence of SEQ ID NO:52, an LCDR2 comprising the amino acid sequence of SEQ ID NO:54, and an LCDR3 comprising the amino acid sequence of SEQ ID NO:56.

22. The isolated monoclonal antibody or antigen-binding fragment thereof of claim 1, wherein the antibody or antigen-binding fragment thereof comprises an HCVR comprising the amino acid sequence of SEQ ID NO:2 and an LCVR comprising the amino acid sequence of SEQ ID NO:10.

23. The isolated monoclonal antibody or antigen-binding fragment thereof of claim 1, wherein the antibody or antigen-binding fragment thereof comprises an HCVR comprising the amino acid sequence of SEQ ID NO:22 and an LCVR comprising the amino acid sequence of SEQ ID NO:30.

24. The isolated monoclonal antibody or antigen-binding fragment thereof of claim 1, wherein the antibody or antigen-binding fragment thereof comprises an HCVR comprising the amino acid sequence of SEQ ID NO:42 and an LCVR comprising the amino acid sequence of SEQ ID NO:50.

25. The isolated monoclonal antibody or antigen-binding fragment thereof of claim 1, wherein the antibody or antigen-binding fragment thereof comprises a heavy chain comprising the amino acid sequence of SEQ ID NO:18 and a light chain comprising the amino acid sequence of SEQ ID NO:20.

26. The isolated monoclonal antibody or antigen-binding fragment thereof of claim 1, wherein the antibody or antigen-binding fragment thereof comprises a heavy chain comprising the amino acid sequence of SEQ ID NO:38 and a light chain comprising the amino acid sequence of SEQ ID NO:40.

27. The isolated monoclonal antibody or antigen-binding fragment thereof of claim 1, wherein the antibody or antigen-binding fragment thereof comprises a heavy chain comprising the amino acid sequence of SEQ ID NO:58 and a light chain comprising the amino acid sequence of SEQ ID NO:60.

* * * * *